(12) United States Patent
Divino et al.

(10) Patent No.: US 11,786,253 B2
(45) Date of Patent: Oct. 17, 2023

(54) OCCLUSIVE DEVICES

(71) Applicant: Covidien LP, Mansfield, MA (US)

(72) Inventors: Vincent Divino, Mission Viejo, CA (US); Earl Frederick Bardsley, San Clemente, CA (US); Richard Rhee, Anaheim, CA (US); Madhur Arunrao Kadam, Lake Forest, CA (US); Julie Kulak, Trabuco Canyon, CA (US)

(73) Assignee: COVIDIEN LP, Mansfield, MA (US)

( * ) Notice: Subject to any disclaimer, the term of this patent is extended or adjusted under 35 U.S.C. 154(b) by 762 days.

(21) Appl. No.: 16/424,095

(22) Filed: May 28, 2019

(65) Prior Publication Data
US 2019/0290286 A1    Sep. 26, 2019

Related U.S. Application Data

(63) Continuation of application No. 16/412,967, filed on May 15, 2019, which is a continuation of application
(Continued)

(51) Int. Cl.
*A61B 17/12* (2006.01)
*A61F 2/95* (2013.01)

(52) U.S. Cl.
CPC .... *A61B 17/12113* (2013.01); *A61B 17/1219* (2013.01); *A61B 17/12022* (2013.01);
(Continued)

(58) Field of Classification Search
CPC ........ A61B 17/12113; A61B 17/12022; A61B 17/12027; A61B 17/12031;
(Continued)

(56) References Cited

U.S. PATENT DOCUMENTS

| | | | |
|---|---|---|---|
| 5,041,090 | A | 8/1991 | Scheglov et al. |
| 5,250,071 | A | 10/1993 | Palermo |

(Continued)

FOREIGN PATENT DOCUMENTS

| | | |
|---|---|---|
| CN | 101460102 A | 6/2009 |
| CN | 102083493 A | 6/2011 |

(Continued)

OTHER PUBLICATIONS

International Search Report and Written Opinion dated Feb. 23, 2021, International Application No. PCT/US20/70743, 14 pages.

*Primary Examiner* — Dianne Dornbusch
(74) *Attorney, Agent, or Firm* — FORTEM IP LLP; Mary Fox

(57) ABSTRACT

A system for treatment of an aneurysm includes an intrasaccular device that can be delivered using a catheter. The device can include at least one expandable structure adapted to transition from a compressed configuration to an expanded configuration when released into the aneurysm. The expandable structure can have a specific shape or porosity. Multiple expandable structures can also be used, in which case each of the expandable structures can have a unique shape or porosity profile. The morphology of the aneurysm and orientation of any connecting arteries can determine the type, size, shape, number, and porosity profile of the expandable structure used in treating the aneurysm.

22 Claims, 29 Drawing Sheets

Related U.S. Application Data

No. 14/079,591, filed on Nov. 13, 2013, now Pat. No. 10,327,781.

(60) Provisional application No. 61/725,768, filed on Nov. 13, 2012.

(52) U.S. Cl.
CPC .. *A61B 17/12118* (2013.01); *A61B 17/12159* (2013.01); *A61B 17/12163* (2013.01); *A61B 17/12186* (2013.01); *A61F 2/95* (2013.01); *A61B 17/1214* (2013.01); *A61B 2017/1205* (2013.01)

(58) Field of Classification Search
CPC .......... A61B 17/12036; A61B 17/1204; A61B 17/12045; A61B 17/12109; A61B 17/12122; A61B 17/12131; A61B 17/12136; A61B 17/12159; A61B 17/12163; A61B 17/12172; A61B 17/12181; A61B 17/12186; A61B 17/1219; A61B 17/0057; A61B 2017/12054; A61B 2017/12127; A61B 2017/00575; A61B 2017/00601; A61B 2017/0061; A61B 2017/0606; A61B 2017/00632; A61B 2017/00637; A61B 2017/00641

See application file for complete search history.

(56) References Cited

U.S. PATENT DOCUMENTS

| | | | |
|---|---|---|---|
| 5,284,488 | A | 2/1994 | Sideris |
| 5,326,350 | A | 7/1994 | Li |
| 5,354,295 | A | 10/1994 | Guglielmi et al. |
| 5,405,379 | A | 4/1995 | Lane |
| 5,417,708 | A | 5/1995 | Hall et al. |
| 5,645,558 | A | 7/1997 | Horton |
| 5,669,931 | A | 9/1997 | Kupiecki et al. |
| 5,725,552 | A | 3/1998 | Kotula et al. |
| 5,733,294 | A | 3/1998 | Forber et al. |
| 5,741,333 | A | 4/1998 | Frid |
| 5,749,891 | A | 5/1998 | Ken et al. |
| 5,749,894 | A | 5/1998 | Engelson |
| 5,749,895 | A | 5/1998 | Sawyer et al. |
| 5,749,919 | A | 5/1998 | Blanc |
| 5,814,062 | A | 9/1998 | Sepetka et al. |
| 5,823,198 | A | 10/1998 | Jones et al. |
| 5,846,261 | A | 12/1998 | Kotula et al. |
| 5,911,731 | A | 6/1999 | Pham et al. |
| 5,916,235 | A | 6/1999 | Guglielmi |
| 5,925,060 | A | 7/1999 | Forber |
| 5,928,260 | A | 7/1999 | Chin et al. |
| 5,935,148 | A | 8/1999 | Villar et al. |
| 5,941,249 | A | 8/1999 | Maynard |
| 5,944,738 | A | 8/1999 | Amplatz et al. |
| 5,951,599 | A | 9/1999 | McCrory |
| 5,964,797 | A | 10/1999 | Ho |
| 5,976,169 | A | 11/1999 | Imran |
| 5,980,554 | A | 11/1999 | Lenker et al. |
| 6,022,374 | A | 2/2000 | Imran |
| 6,033,423 | A | 3/2000 | Ken et al. |
| 6,036,720 | A | 3/2000 | Abrams et al. |
| 6,063,070 | A | 5/2000 | Eder |
| 6,063,104 | A | 5/2000 | Villar et al. |
| 6,086,577 | A | 7/2000 | Ken et al. |
| 6,090,125 | A | 7/2000 | Horton |
| 6,093,199 | A | 7/2000 | Brown et al. |
| 6,096,021 | A | 8/2000 | Helm et al. |
| 6,123,715 | A | 9/2000 | Amplatz |
| 6,139,564 | A | 10/2000 | Teoh |
| 6,152,144 | A | 11/2000 | Lesh et al. |
| 6,159,531 | A | 12/2000 | Dang et al. |
| 6,165,193 | A | 12/2000 | Greene et al. |
| 6,168,615 | B1 | 1/2001 | Ken et al. |
| 6,168,622 | B1 | 1/2001 | Mazzocchi |
| 6,238,403 | B1 | 5/2001 | Greene et al. |
| 6,299,619 | B1 | 10/2001 | Greene et al. |
| 6,309,367 | B1 | 10/2001 | Boock |
| 6,322,576 | B1 | 11/2001 | Wallace et al. |
| 6,344,048 | B1 | 2/2002 | Chin et al. |
| 6,346,117 | B1 | 2/2002 | Greenhalgh |
| 6,350,270 | B1 | 2/2002 | Roue |
| 6,368,339 | B1 | 4/2002 | Amplatz |
| 6,371,980 | B1 | 4/2002 | Rudakov et al. |
| 6,375,668 | B1 * | 4/2002 | Gifford ............ A61B 17/12022 606/200 |
| 6,379,329 | B1 | 4/2002 | Naglreiter et al. |
| 6,383,174 | B1 | 5/2002 | Eder |
| 6,391,037 | B1 | 5/2002 | Greenhalgh |
| 6,428,558 | B1 | 8/2002 | Jones et al. |
| 6,447,531 | B1 | 9/2002 | Amplatz |
| 6,451,050 | B1 | 9/2002 | Rudakov et al. |
| 6,454,780 | B1 | 9/2002 | Wallace |
| 6,494,884 | B2 | 12/2002 | Gifford et al. |
| 6,506,204 | B2 | 1/2003 | Mazzocchi |
| 6,511,468 | B1 | 1/2003 | Cragg et al. |
| 6,547,804 | B2 | 4/2003 | Porter et al. |
| 6,551,303 | B1 | 4/2003 | Van et al. |
| 6,569,179 | B2 | 5/2003 | Teoh et al. |
| 6,579,303 | B2 | 6/2003 | Amplatz |
| 6,585,748 | B1 | 7/2003 | Jeffree |
| 6,589,256 | B2 | 7/2003 | Forber |
| 6,589,265 | B1 | 7/2003 | Palmer et al. |
| 6,591,472 | B1 | 7/2003 | Noone et al. |
| 6,592,605 | B2 | 7/2003 | Lenker et al. |
| 6,599,308 | B2 | 7/2003 | Amplatz |
| 6,602,261 | B2 | 8/2003 | Greene et al. |
| 6,605,101 | B1 | 8/2003 | Schaefer et al. |
| 6,605,102 | B1 | 8/2003 | Mazzocchi et al. |
| 6,605,111 | B2 | 8/2003 | Bose et al. |
| 6,613,074 | B1 | 9/2003 | Mitelberg et al. |
| 6,626,939 | B1 | 9/2003 | Burnside et al. |
| 6,635,068 | B1 | 10/2003 | Dubrul et al. |
| 6,652,555 | B1 | 11/2003 | Vantassel et al. |
| 6,652,556 | B1 | 11/2003 | Vantassel et al. |
| 6,666,882 | B1 | 12/2003 | Bose et al. |
| 6,669,717 | B2 | 12/2003 | Marotta et al. |
| 6,669,721 | B1 | 12/2003 | Bose et al. |
| 6,682,546 | B2 | 1/2004 | Amplatz |
| 6,689,150 | B1 | 2/2004 | Vantassel et al. |
| 6,689,486 | B2 | 2/2004 | Ho et al. |
| 6,723,112 | B2 | 4/2004 | Ho et al. |
| 6,723,116 | B2 | 4/2004 | Taheri |
| 6,730,108 | B2 | 5/2004 | Van et al. |
| 6,746,468 | B1 | 6/2004 | Sepetka et al. |
| 6,746,890 | B2 | 6/2004 | Gupta et al. |
| 6,780,196 | B2 | 8/2004 | Chin et al. |
| 6,802,851 | B2 | 10/2004 | Jones et al. |
| 6,811,560 | B2 | 11/2004 | Jones et al. |
| 6,855,153 | B2 | 2/2005 | Saadat |
| 6,855,154 | B2 | 2/2005 | Abdel-Gawwad |
| 6,878,384 | B2 | 4/2005 | Cruise et al. |
| 6,905,503 | B2 | 6/2005 | Gifford et al. |
| 6,936,055 | B1 | 8/2005 | Ken et al. |
| 6,949,113 | B2 | 9/2005 | Van et al. |
| 6,991,617 | B2 | 1/2006 | Hektner et al. |
| 6,994,092 | B2 | 2/2006 | Van et al. |
| 6,994,717 | B2 | 2/2006 | Konya et al. |
| 7,011,671 | B2 | 3/2006 | Welch |
| 7,014,645 | B2 | 3/2006 | Greene et al. |
| 7,029,487 | B2 | 4/2006 | Greene et al. |
| 7,029,949 | B2 | 4/2006 | Farnworth et al. |
| 7,070,609 | B2 | 7/2006 | West |
| 7,083,632 | B2 | 8/2006 | Avellanet et al. |
| 7,128,073 | B1 | 10/2006 | Van et al. |
| 7,128,736 | B1 * | 10/2006 | Abrams ............ A61B 17/0057 606/1 |
| 7,153,323 | B1 | 12/2006 | Teoh et al. |
| 7,169,177 | B2 | 1/2007 | Obara |
| 7,195,636 | B2 | 3/2007 | Avellanet et al. |
| 7,229,461 | B2 | 6/2007 | Chin et al. |

(56) References Cited

U.S. PATENT DOCUMENTS

| | | |
|---|---|---|
| 7,232,461 B2 | 6/2007 | Ramer |
| 7,306,622 B2 | 12/2007 | Jones et al. |
| 7,326,225 B2 | 2/2008 | Ferrera et al. |
| 7,331,980 B2 | 2/2008 | Dubrul et al. |
| 7,367,986 B2 | 5/2008 | Mazzocchi et al. |
| 7,410,482 B2 | 8/2008 | Murphy et al. |
| 7,419,503 B2 | 9/2008 | Pulnev et al. |
| 7,481,821 B2 | 1/2009 | Fogarty et al. |
| 7,491,214 B2 | 2/2009 | Greene et al. |
| 7,569,066 B2 | 8/2009 | Gerberding et al. |
| 7,572,288 B2 | 8/2009 | Cox |
| 7,597,704 B2 | 10/2009 | Frazier et al. |
| 7,601,160 B2 | 10/2009 | Richter |
| 7,608,088 B2 | 10/2009 | Jones et al. |
| 7,695,488 B2 | 4/2010 | Berenstein et al. |
| 7,699,056 B2 | 4/2010 | Tran et al. |
| 7,708,754 B2 | 5/2010 | Balgobin et al. |
| 7,727,189 B2 | 6/2010 | Vantassel et al. |
| 7,744,583 B2 | 6/2010 | Seifert et al. |
| 7,744,652 B2 | 6/2010 | Morsi |
| 7,976,527 B2 | 7/2011 | Cragg et al. |
| RE42,625 E | 8/2011 | Guglielmi |
| 7,993,364 B2 | 8/2011 | Morsi |
| RE42,758 E | 9/2011 | Ken et al. |
| 3,012,210 A1 | 9/2011 | Lin et al. |
| 8,043,326 B2 | 10/2011 | Hancock et al. |
| 8,062,379 B2 | 11/2011 | Morsi |
| 8,075,585 B2 | 12/2011 | Lee et al. |
| 8,137,293 B2 | 3/2012 | Zhou et al. |
| 8,142,456 B2 | 3/2012 | Rosqueta et al. |
| 8,202,280 B2 | 6/2012 | Richter |
| 8,211,160 B2 | 7/2012 | Garrison et al. |
| 8,221,445 B2 | 7/2012 | Van et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,372,062 B2 | 2/2013 | Murphy et al. |
| 8,398,670 B2 | 3/2013 | Amplatz et al. |
| 8,425,541 B2 | 4/2013 | Masters et al. |
| 8,470,013 B2 | 6/2013 | Duggal et al. |
| 8,597,320 B2 | 12/2013 | Sepetka et al. |
| 8,603,128 B2 | 12/2013 | Greene et al. |
| 8,715,317 B1 | 5/2014 | Janardhan et al. |
| 8,834,515 B2 | 9/2014 | Win et al. |
| 8,906,057 B2 | 12/2014 | Connor et al. |
| 8,974,512 B2 | 3/2015 | Aboytes et al. |
| 8,998,947 B2 | 4/2015 | Aboytes et al. |
| 9,211,202 B2 | 12/2015 | Strother et al. |
| 9,301,769 B2 | 4/2016 | Brady et al. |
| 9,314,248 B2 | 4/2016 | Molaei |
| 9,486,224 B2 | 11/2016 | Riina et al. |
| 9,629,636 B2 | 4/2017 | Fogarty et al. |
| 9,681,861 B2 | 6/2017 | Heisel et al. |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,028,745 B2 | 7/2018 | Morsi |
| 10,130,372 B2 | 11/2018 | Griffin |
| 11,179,159 B2 | 11/2021 | Cox et al. |
| 11,389,309 B2 | 7/2022 | Ruvalcaba et al. |
| 2001/0000797 A1 | 5/2001 | Mazzocchi |
| 2001/0001835 A1 | 5/2001 | Greene et al. |
| 2002/0026210 A1 | 2/2002 | Abdel-Gawwad |
| 2002/0042628 A1 | 4/2002 | Chin et al. |
| 2002/0062145 A1 | 5/2002 | Rudakov et al. |
| 2002/0119177 A1 | 8/2002 | Bowman et al. |
| 2002/0147462 A1 | 10/2002 | Mair et al. |
| 2002/0165572 A1 | 11/2002 | Saadat |
| 2002/0169473 A1* | 11/2002 | Sepetka ............ A61B 17/12022 606/200 |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1* | 2/2003 | Teoh ............... A61B 17/12022 606/191 |
| 2003/0040772 A1 | 2/2003 | Hyodoh et al. |
| 2003/0055440 A1 | 3/2003 | Jones et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2003/0149490 A1 | 8/2003 | Ashman |
| 2003/0171739 A1 | 9/2003 | Murphy et al. |
| 2003/0187473 A1 | 10/2003 | Berenstein et al. |
| 2003/0195553 A1* | 10/2003 | Wallace ........... A61B 17/12172 606/200 |
| 2003/0212419 A1 | 11/2003 | West |
| 2004/0034386 A1 | 2/2004 | Fulton et al. |
| 2004/0044361 A1 | 3/2004 | Frazier et al. |
| 2004/0044391 A1 | 3/2004 | Porter |
| 2004/0064093 A1 | 4/2004 | Hektner et al. |
| 2004/0098027 A1 | 5/2004 | Teoh et al. |
| 2004/0106945 A1 | 6/2004 | Thramann et al. |
| 2004/0115164 A1 | 6/2004 | Pierce et al. |
| 2004/0122467 A1 | 6/2004 | Vantassel et al. |
| 2004/0133222 A1* | 7/2004 | Tran ................. A61B 17/12022 606/157 |
| 2004/0138758 A1 | 7/2004 | Kronengold et al. |
| 2004/0161451 A1 | 8/2004 | Pierce et al. |
| 2004/0181253 A1 | 9/2004 | Sepetka et al. |
| 2005/0021077 A1 | 1/2005 | Chin et al. |
| 2005/0049625 A1 | 3/2005 | Shaya et al. |
| 2005/0131443 A1 | 6/2005 | Abdel-Gawwad |
| 2005/0222580 A1 | 10/2005 | Gifford et al. |
| 2005/0267510 A1 | 12/2005 | Razack |
| 2005/0267511 A1 | 12/2005 | Marks et al. |
| 2005/0267527 A1 | 12/2005 | Sandoval et al. |
| 2005/0277978 A1 | 12/2005 | Greenhalgh |
| 2005/0278023 A1 | 12/2005 | Zwirkoski |
| 2006/0028209 A1 | 2/2006 | Walker |
| 2006/0034883 A1 | 2/2006 | Dang et al. |
| 2006/0052816 A1 | 3/2006 | Bates et al. |
| 2006/0064151 A1* | 3/2006 | Guterman ........ A61B 17/12022 623/1.3 |
| 2006/0106421 A1 | 5/2006 | Teoh |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0122548 A1 | 6/2006 | Abrams |
| 2006/0155323 A1 | 7/2006 | Porter et al. |
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2007/0003594 A1 | 1/2007 | Brady et al. |
| 2007/0010850 A1 | 1/2007 | Balgobin et al. |
| 2007/0014831 A1 | 1/2007 | Sung et al. |
| 2007/0083226 A1 | 4/2007 | Buiser et al. |
| 2007/0100426 A1 | 5/2007 | Rudakov et al. |
| 2007/0135907 A1 | 6/2007 | Wilson et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179507 A1 | 8/2007 | Shah |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0191924 A1 | 8/2007 | Rudakov |
| 2007/0198059 A1 | 8/2007 | Patel et al. |
| 2007/0198075 A1* | 8/2007 | Levy ............... A61B 17/1214 623/1.36 |
| 2007/0219619 A1 | 9/2007 | Dieck et al. |

(56) References Cited

U.S. PATENT DOCUMENTS

| | | | |
|---|---|---|---|
| 2007/0265656 A1* | 11/2007 | Amplatz | A61B 17/12172 606/200 |
| 2007/0270902 A1 | 11/2007 | Slazas et al. | |
| 2007/0276426 A1 | 11/2007 | Euteneuer | |
| 2007/0276427 A1 | 11/2007 | Euteneuer | |
| 2007/0282373 A1 | 12/2007 | Ashby et al. | |
| 2007/0288083 A1 | 12/2007 | Hines | |
| 2008/0033366 A1 | 2/2008 | Matson et al. | |
| 2008/0065145 A1 | 3/2008 | Carpenter | |
| 2008/0081763 A1 | 4/2008 | Swetlin et al. | |
| 2008/0082176 A1 | 4/2008 | Slazas | |
| 2008/0086196 A1 | 4/2008 | Truckai et al. | |
| 2008/0109057 A1 | 5/2008 | Calabria et al. | |
| 2008/0114391 A1 | 5/2008 | Dieck et al. | |
| 2008/0114436 A1 | 5/2008 | Dieck et al. | |
| 2008/0125852 A1 | 5/2008 | Garrison et al. | |
| 2008/0132820 A1 | 6/2008 | Buckman et al. | |
| 2008/0140177 A1* | 6/2008 | Hines | A61M 29/02 606/108 |
| 2008/0195137 A1 | 8/2008 | Alleyne et al. | |
| 2008/0200945 A1 | 8/2008 | Amplatz et al. | |
| 2008/0200979 A1 | 8/2008 | Dieck et al. | |
| 2008/0221600 A1 | 9/2008 | Dieck et al. | |
| 2008/0281350 A1* | 11/2008 | Sepetka | A61B 17/12172 606/200 |
| 2009/0018637 A1 | 1/2009 | Paul et al. | |
| 2009/0024224 A1 | 1/2009 | Chen et al. | |
| 2009/0025820 A1 | 1/2009 | Adams | |
| 2009/0043375 A1 | 2/2009 | Rudakov et al. | |
| 2009/0056722 A1 | 3/2009 | Swann | |
| 2009/0062899 A1 | 3/2009 | Dang et al. | |
| 2009/0076540 A1 | 3/2009 | Marks et al. | |
| 2009/0112249 A1 | 4/2009 | Miles et al. | |
| 2009/0112251 A1 | 4/2009 | Qian et al. | |
| 2009/0125119 A1 | 5/2009 | Obermiller et al. | |
| 2009/0148492 A1 | 6/2009 | Dave et al. | |
| 2009/0155367 A1 | 6/2009 | Neuwirth et al. | |
| 2009/0187214 A1 | 7/2009 | Amplatz et al. | |
| 2009/0264978 A1 | 10/2009 | Dieck et al. | |
| 2009/0270974 A1 | 10/2009 | Berez et al. | |
| 2009/0275974 A1 | 11/2009 | Marchand et al. | |
| 2009/0287291 A1 | 11/2009 | Becking et al. | |
| 2009/0287292 A1 | 11/2009 | Becking et al. | |
| 2009/0287294 A1 | 11/2009 | Rosqueta et al. | |
| 2009/0287297 A1 | 11/2009 | Cox | |
| 2009/0297582 A1 | 12/2009 | Meyer et al. | |
| 2009/0306702 A1 | 12/2009 | Miloslavski et al. | |
| 2009/0318892 A1 | 12/2009 | Aboytes et al. | |
| 2009/0318941 A1 | 12/2009 | Sepetka et al. | |
| 2009/0319023 A1 | 12/2009 | Hildebrand et al. | |
| 2010/0023048 A1 | 1/2010 | Mach | |
| 2010/0030200 A1 | 2/2010 | Strauss et al. | |
| 2010/0036410 A1 | 2/2010 | Krolik et al. | |
| 2010/0106178 A1 | 4/2010 | Obermiller et al. | |
| 2010/0131002 A1 | 5/2010 | Connor et al. | |
| 2010/0139465 A1 | 6/2010 | Christian et al. | |
| 2010/0144895 A1 | 6/2010 | Porter | |
| 2010/0160949 A1* | 6/2010 | Takuma | A61B 17/12136 606/195 |
| 2010/0174269 A1 | 7/2010 | Tompkins et al. | |
| 2010/0185271 A1 | 7/2010 | Zhang | |
| 2010/0228184 A1 | 9/2010 | Mavani et al. | |
| 2010/0249830 A1 | 9/2010 | Nelson | |
| 2010/0256527 A1 | 10/2010 | Lippert et al. | |
| 2010/0256528 A1 | 10/2010 | Lippert et al. | |
| 2010/0256601 A1 | 10/2010 | Lippert et al. | |
| 2010/0256602 A1 | 10/2010 | Lippert et al. | |
| 2010/0256603 A1 | 10/2010 | Lippert et al. | |
| 2010/0256604 A1 | 10/2010 | Lippert et al. | |
| 2010/0256605 A1 | 10/2010 | Lippert et al. | |
| 2010/0256606 A1 | 10/2010 | Lippert et al. | |
| 2010/0262014 A1 | 10/2010 | Huang | |
| 2010/0268201 A1 | 10/2010 | Tieu et al. | |
| 2010/0274276 A1 | 10/2010 | Chow et al. | |
| 2010/0298791 A1 | 11/2010 | Jones et al. | |
| 2010/0312061 A1 | 12/2010 | Hess et al. | |
| 2011/0022149 A1 | 1/2011 | Cox et al. | |
| 2011/0046658 A1 | 2/2011 | Connor et al. | |
| 2011/0077620 A1 | 3/2011 | Debeer | |
| 2011/0125110 A1 | 5/2011 | Cotton | |
| 2011/0137332 A1 | 6/2011 | Sepetka et al. | |
| 2011/0137405 A1 | 6/2011 | Wilson et al. | |
| 2011/0144669 A1 | 6/2011 | Becking et al. | |
| 2011/0152993 A1 | 6/2011 | Marchand et al. | |
| 2011/0166588 A1 | 7/2011 | Connor et al. | |
| 2011/0196415 A1 | 8/2011 | Ujiie et al. | |
| 2011/0202085 A1 | 8/2011 | Loganathan et al. | |
| 2011/0208227 A1 | 8/2011 | Becking | |
| 2011/0224776 A1 | 9/2011 | Sepetka et al. | |
| 2011/0245862 A1 | 10/2011 | Dieck et al. | |
| 2011/0251699 A1 | 10/2011 | Ladet | |
| 2011/0265943 A1 | 11/2011 | Rosqueta et al. | |
| 2011/0319926 A1 | 12/2011 | Becking et al. | |
| 2012/0010644 A1 | 1/2012 | Sideris et al. | |
| 2012/0022572 A1 | 1/2012 | Braun et al. | |
| 2012/0041472 A1 | 2/2012 | Tan et al. | |
| 2012/0101510 A1 | 4/2012 | Lenker et al. | |
| 2012/0116350 A1 | 5/2012 | Strauss et al. | |
| 2012/0143237 A1 | 6/2012 | Cam et al. | |
| 2012/0143243 A1 | 6/2012 | Hill et al. | |
| 2012/0165919 A1 | 6/2012 | Cox et al. | |
| 2012/0197283 A1 | 8/2012 | Marchand et al. | |
| 2012/0239074 A1 | 9/2012 | Aboytes et al. | |
| 2012/0283768 A1 | 11/2012 | Cox et al. | |
| 2012/0283769 A1 | 11/2012 | Cruise et al. | |
| 2012/0310269 A1 | 12/2012 | Fearnot et al. | |
| 2012/0316598 A1 | 12/2012 | Becking et al. | |
| 2012/0316632 A1 | 12/2012 | Gao | |
| 2012/0323271 A1 | 12/2012 | Obermiller et al. | |
| 2012/0330341 A1 | 12/2012 | Becking et al. | |
| 2012/0330347 A1 | 12/2012 | Becking et al. | |
| 2012/0330348 A1 | 12/2012 | Strauss et al. | |
| 2013/0066357 A1 | 3/2013 | Aboytes et al. | |
| 2013/0066360 A1 | 3/2013 | Becking et al. | |
| 2013/0073026 A1 | 3/2013 | Russo et al. | |
| 2013/0085522 A1 | 4/2013 | Becking et al. | |
| 2013/0116722 A1 | 5/2013 | Aboytes et al. | |
| 2013/0274866 A1 | 10/2013 | Cox et al. | |
| 2014/0012307 A1 | 1/2014 | Franano et al. | |
| 2014/0058420 A1 | 2/2014 | Hannes et al. | |
| 2014/0135810 A1 | 5/2014 | Divino et al. | |
| 2014/0135811 A1 | 5/2014 | Divino et al. | |
| 2014/0135812 A1 | 5/2014 | Divino et al. | |
| 2014/0257360 A1 | 9/2014 | Keillor | |
| 2014/0257374 A1 | 9/2014 | Heisel et al. | |
| 2014/0316012 A1 | 10/2014 | Freyman et al. | |
| 2014/0371734 A1 | 12/2014 | Truckai | |
| 2015/0216684 A1 | 8/2015 | Enzmann et al. | |
| 2015/0250628 A1 | 9/2015 | Monstadt et al. | |
| 2015/0272589 A1 | 10/2015 | Lorenzo | |
| 2015/0272590 A1 | 10/2015 | Aboytes et al. | |
| 2015/0313605 A1 | 11/2015 | Griffin | |
| 2015/0313737 A1 | 11/2015 | Tippett et al. | |
| 2015/0327843 A1 | 11/2015 | Garrison | |
| 2015/0342613 A1 | 12/2015 | Aboytes et al. | |
| 2016/0022445 A1 | 1/2016 | Ruvalcaba et al. | |
| 2016/0030050 A1 | 2/2016 | Franano et al. | |
| 2016/0066921 A1 | 3/2016 | Seifert et al. | |
| 2016/0135984 A1 | 5/2016 | Rudakov et al. | |
| 2016/0206320 A1 | 7/2016 | Connor | |
| 2016/0206321 A1 | 7/2016 | Connor | |
| 2017/0150971 A1 | 6/2017 | Hines | |
| 2017/0156734 A1 | 6/2017 | Griffin | |
| 2017/0156903 A1 | 6/2017 | Shobayashi | |
| 2017/0189035 A1 | 7/2017 | Porter | |
| 2017/0224355 A1 | 8/2017 | Bowman et al. | |
| 2017/0266023 A1 | 9/2017 | Thomas | |
| 2017/0340333 A1 | 11/2017 | Badruddin et al. | |
| 2017/0354421 A1 | 12/2017 | Maguire et al. | |
| 2017/0367708 A1 | 12/2017 | Mayer et al. | |
| 2018/0049859 A1 | 2/2018 | Stoppenhagen et al. | |
| 2018/0125686 A1 | 5/2018 | Lu | |
| 2018/0140305 A1 | 5/2018 | Connor | |
| 2018/0161185 A1 | 6/2018 | Kresslein et al. | |

(56) References Cited

U.S. PATENT DOCUMENTS

| | | | |
|---|---|---|---|
| 2018/0193025 | A1 | 7/2018 | Walzman |
| 2018/0193026 | A1 | 7/2018 | Yang et al. |
| 2018/0206852 | A1 | 7/2018 | Moeller |
| 2019/0053811 | A1 | 2/2019 | Garza et al. |
| 2019/0223876 | A1 | 7/2019 | Badruddin et al. |
| 2019/0223881 | A1 | 7/2019 | Hewitt et al. |
| 2019/0282242 | A1 | 9/2019 | Divino et al. |
| 2019/0343532 | A1 | 11/2019 | Divino et al. |
| 2020/0061099 | A1 | 2/2020 | Li et al. |
| 2020/0113576 | A1 | 4/2020 | Gorochow et al. |
| 2021/0128162 | A1 | 5/2021 | Rhee et al. |
| 2021/0128169 | A1 | 5/2021 | Li et al. |
| 2021/0129275 | A1 | 5/2021 | Nguyen et al. |
| 2021/0153872 | A1 | 5/2021 | Nguyen et al. |
| 2021/0196284 | A1 | 7/2021 | Gorochow et al. |
| 2021/0212698 | A1 | 7/2021 | Connor |

FOREIGN PATENT DOCUMENTS

| | | |
|---|---|---|
| CN | 102202585 A | 9/2011 |
| CN | 202313544 U | 7/2012 |
| CN | 102740799 A | 10/2012 |
| CN | 105105812 A | 12/2015 |
| DE | 102011102933 A1 | 12/2012 |
| EP | 0717969 A2 | 6/1996 |
| EP | 1188414 A1 | 3/2002 |
| EP | 1813213 A2 | 8/2007 |
| EP | 2208483 A1 | 7/2010 |
| EP | 2468348 B1 | 10/2016 |
| JP | 2005261951 A | 9/2005 |
| JP | 2008521492 A | 6/2008 |
| WO | 9406502 A2 | 3/1994 |
| WO | 9905977 A1 | 2/1999 |
| WO | 03011151 A1 | 2/2003 |
| WO | 2006034149 A2 | 3/2006 |
| WO | 2007006139 A1 | 1/2007 |
| WO | 2007079402 A2 | 7/2007 |
| WO | 2007121405 A2 | 10/2007 |
| WO | 2008074027 A1 | 6/2008 |
| WO | 2009014528 A1 | 1/2009 |
| WO | 2009134337 A1 | 11/2009 |
| WO | 2010009019 A1 | 1/2010 |
| WO | 2010027363 A1 | 3/2010 |
| WO | 2010028300 A1 | 3/2010 |
| WO | 2010077599 A1 | 7/2010 |
| WO | 2011066962 A1 | 6/2011 |
| WO | 2011095966 A1 | 8/2011 |
| WO | 2012034135 A1 | 3/2012 |
| WO | 2013112944 A1 | 8/2013 |
| WO | 2013138615 A2 | 9/2013 |
| WO | 2013138615 A3 | 9/2014 |
| WO | 2015160721 A1 | 10/2015 |
| WO | 2017074411 A1 | 5/2017 |
| WO | 2018051187 A1 | 3/2018 |

\* cited by examiner

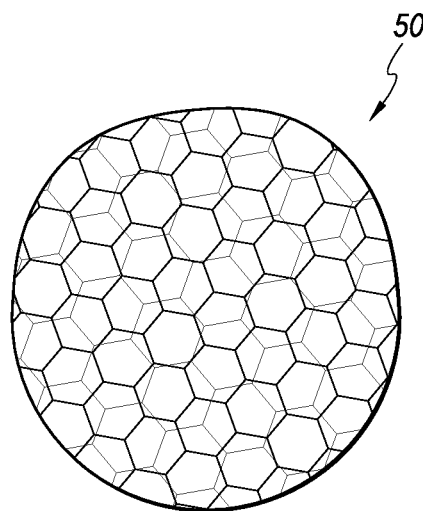
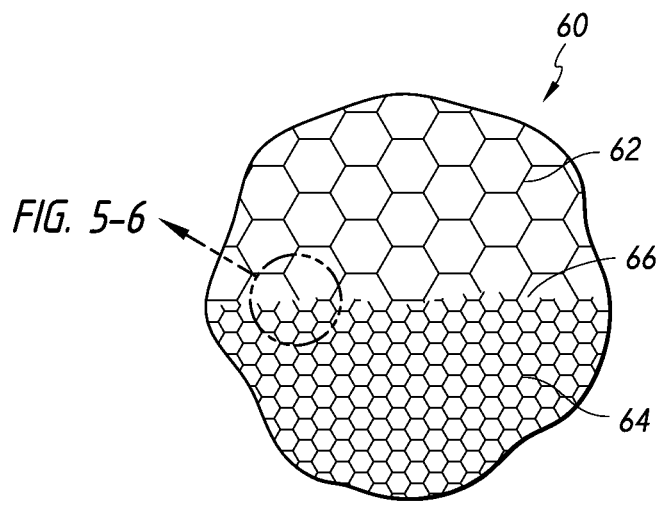
FIG. 3
FIG. 4
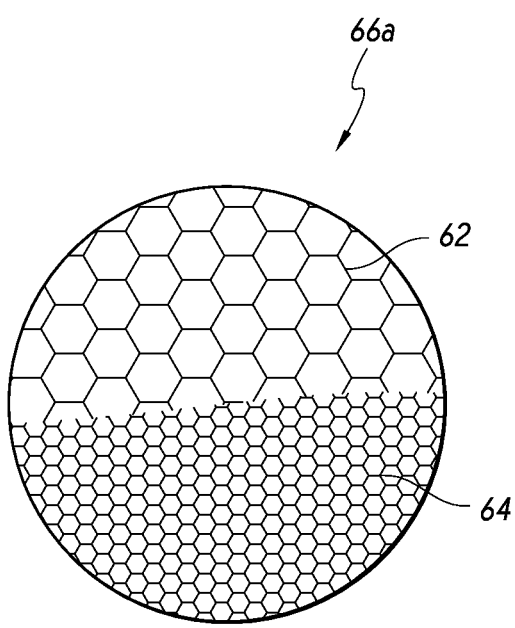
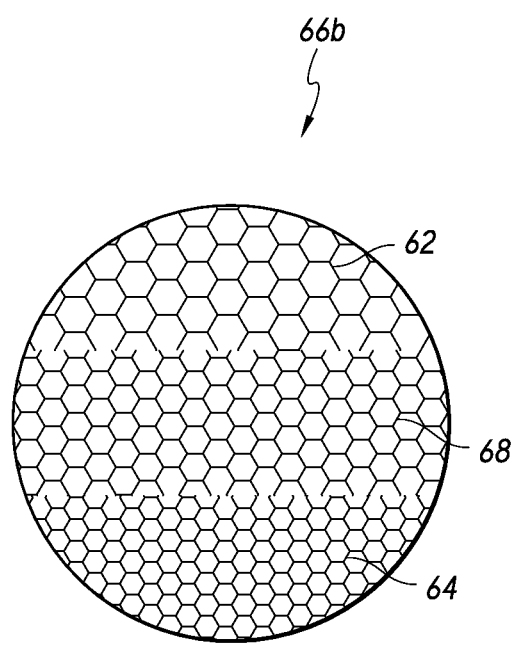
FIG. 5
FIG. 6

OCCLUSIVE DEVICES

CROSS-REFERENCE TO RELATED APPLICATIONS

This application is a continuation of U.S. application Ser. No. 16/412,967, filed May 15, 2019, which is a continuation of U.S. application Ser. No. 14/079,591, filed Nov. 13, 2013, which claims the benefit of U.S. Provisional Application No. 61/725,768, filed Nov. 13, 2012, all of which are incorporated herein by reference in their entireties.

BACKGROUND

1. Field of the Inventions

The present disclosure generally relates to a system and method for delivering and deploying a medical device within a vessel, more particularly, it relates to a system and method for delivering and deploying an endoluminal therapeutic device within the vasculature of a patient to embolize and occlude aneurysms, particularly, cerebral aneurysms.

2. Description of the Related Art

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury or a congenital abnormality. Aneurysms could be found in different parts of the body with the most common being abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" or "pack" an aneurysm; (iv) using detachable balloons or coils to occlude the parent vessel that supplies the aneurysm; and (v) intravascular stenting.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

SUMMARY

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

Systems and procedures for treating aneurysms can include an intrasaccular device having one or more expandable components that can be inserted into an aneurysm to facilitate a thrombotic, healing effect. The components can have a specific characteristics, including porosity, composition, material, shape, size, interconnectedness, inter-engagement, coating, etc. These characteristics can be selected in order to achieve a desired treatment or placement of the intrasaccular device.

The intrasaccular device can comprise a single component having two or more sections that have an average porosity that is different from each other. In some embodiments, the intrasaccular device can comprise multiple components that each have an average porosity. In either embodiment, the intrasaccular device can be arranged within an aneurysm according to a desired porosity profile. The intrasaccular device can be repositioned as necessary within the aneurysm during expansion.

The intrasaccular device can optionally comprise one or more components having a desired shape, which can allow a clinician to implant an intrasaccular device tailored to the aneurysm. A plurality of individual, independent components can operate collectively to form a composite unit having one or more desired characteristics. Such components can have an interlocking structure, which can include a framing component, according to some embodiments.

The intrasaccular device, when used with a framing component, can enable expandable components to be securely retained within an aneurysm. A framing component can comprise a foam or braided structure. Further, one or more expandable components can be inserted into a cavity of or formed by the framing component.

Additionally, the intrasaccular device can also be configured to provide a plurality of interconnected expandable components, extending in linear, planar, or three-dimensional arrays or matrices. These arrays or matrices can be deployed in whole or in part into a target aneurysm, allowing a clinician to select portions of the array or matrix for implantation.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination with each other or one or more other independent embodiments, to form an independent embodiment. The other embodiments can be presented in a similar manner. The following is a non-limiting summary of some embodiments presented herein:

Embodiment 1

A device for treatment of an aneurysm, comprising a foam component having first and second sections, the first section having an average porosity different from an average porosity of the second section, the component being expandable from a compressed configuration to an expanded configuration when released into an aneurysm from a catheter.

Embodiment 2

The device of Embodiment 1, wherein the component is self-expanding to assume the expanded configuration thereof.

Embodiment 3

The device of Embodiment 1, wherein the component is adapted to expand upon exposure to a thermal agent.

Embodiment 4

The device of Embodiment 1, wherein the component is adapted to expand upon exposure to a chemical agent.

Embodiment 5

The device of Embodiment 1, wherein the first section comprises a first material and the second section comprises a second material different from the first material, the first and second sections being coupled to each other.

Embodiment 6

The device of Embodiment 5, wherein the first section is coupled to the second section by chemical bonding, by thermal bonding, or by mechanical crimping.

Embodiment 7

The device of Embodiment 1, wherein the component further comprises a third section coupled to the second section, the third section having an average porosity different from the porosity of the second section.

Embodiment 8

The device of Embodiment 7, wherein the third material is different from the first material.

Embodiment 9

The device of Embodiment 7, wherein the second section is coupled to the third section using an adhesive.

Embodiment 10

The device of Embodiment 7, wherein the second section comprises a second material and the third section comprises a third material different from the second material.

Embodiment 11

The device of Embodiment 7, wherein the third section porosity is different from the first section porosity.

Embodiment 12

The device of Embodiment 11, wherein the first section comprises an average porosity of between about 1 μm and about 150 μm, and the third section comprises an average porosity of between 150 μm and about 300 μm.

Embodiment 13

The device of Embodiment 1, further comprising a transition zone between the first and second sections, the transition zone having an average porosity intermediate the porosities of the first and second sections.

Embodiment 14

The device of Embodiment 13, wherein the transition zone porosity varies spatially from about that of the first section to about that of the second section.

Embodiment 15

The device of Embodiment 13, wherein the porosity in the first and second sections each spatially varies progressively from an end of the first section to an opposite end of the second section.

Embodiment 16

The device of Embodiment 13, wherein the transition zone porosity decreases from the porosity of the first section to the porosity of the second section.

Embodiment 17

The device of Embodiment 1, wherein in the expanded configuration, the component comprises a substantially spherical shape that is divided crosswise into the first and second sections.

Embodiment 18

The device of Embodiment 17, wherein the first and second sections correspond to first and second hemispheres of the substantially spherical shape.

Embodiment 19

The device of Embodiment 17, further comprising a third section coupled to the second section, the first, second, and third sections collectively forming the substantially spherical shape.

Embodiment 20

The device of Embodiment 1, wherein the component further comprises a bioactive coating.

Embodiment 21

The device of Embodiment 20, wherein the bioactive coating comprises a thrombogenic drug.

Embodiment 22

The device of Embodiment 1, wherein the component further comprises an expansion-limiting coating configured to control an expansion rate of the component.

Embodiment 23

The device of Embodiment 1, wherein the first section comprises an average porosity of between about 1 μm and about 100 μm, and the second section comprises an average porosity of between about 100 μm and about 200 μm.

Embodiment 24

The device of Embodiment 1, wherein a shape of the component is selected from the group consisting of cylinders, hemispheres, polyhedrons, prolate spheroids, oblate spheroids, plates, bowls, hollow structures, clover shapes, non-spherical surface of revolution, and combinations thereof.

Embodiment 25

The device of Embodiment 24, further comprising a second foam component having a shape selected from the group consisting of spheres, cylinders, hemispheres, polyhedrons, prolate spheroids, oblate spheroids, plates, bowls, hollow structures, clover shapes, non-spherical surface of revolution, and combinations thereof.

Embodiment 26

The device of Embodiment 25, wherein the foam component and the second foam component are different sizes from each other.

Embodiment 27

The device of Embodiment 25, wherein the foam component and the second foam component are different shapes from each other.

Embodiment 28

The device of Embodiment 25, wherein the foam component and the second foam component have mating structures configured to abut each other in a complementary configuration and restrict at least degrees of freedom of motion of each of the foam component and the second foam component.

Embodiment 29

The device of Embodiment 25, further comprising a plurality of additional foam components having substantially spherical shapes.

Embodiment 30

A system for treatment of an aneurysm, comprising a plurality of foam components being expandable from a compressed configuration to an expanded configuration when released into an aneurysm from a catheter, each of the plurality of components having an average porosity that is different from an average porosity of another of the plurality of components, the plurality of components being positionable within the aneurysm to form a composite foam component having a composite porosity configured to provide a therapeutic effect.

Embodiment 31

The system of Embodiment 30, wherein each of a first group of the plurality of components comprises a first average porosity, and each of a second group of the plurality of components comprises a second average porosity different from the first average porosity.

Embodiment 32

The system of Embodiment 31, wherein the first average porosity is between about 1 µm and about 100 µm, and the second average porosity is between about 100 µm and about 200 µm.

Embodiment 33

The system of Embodiment 30, wherein a shape of at least one of the plurality of components is substantially spherical.

Embodiment 34

The system of Embodiment 30, wherein a shape of at least one of the plurality of components is selected from the group consisting of spheres, cylinders, hemispheres, polyhedrons, prolate spheroids, oblate spheroids, plates, bowls, hollow structures, clover shapes, non-spherical surface of revolution, and combinations thereof.

Embodiment 35

The system of Embodiment 30, wherein each of the plurality of components is interconnected to another of the plurality of components via a filament.

Embodiment 36

The system of Embodiment 35, wherein each of the plurality of components is interconnected to at least two others of the plurality of components.

Embodiment 37

The system of Embodiment 30, wherein the plurality of components is self-expanding to assume the expanded configuration thereof.

Embodiment 38

The system of Embodiment 30, wherein the plurality of components is adapted to expand upon exposure to a thermal agent.

Embodiment 39

The system of Embodiment 30, wherein the plurality of components is adapted to expand upon exposure to a chemical agent.

Embodiment 40

The system of Embodiment 30, wherein at least one of the plurality of components comprises a bioactive coating.

Embodiment 41

The system of Embodiment 30, wherein at least one of the plurality of components comprises a thrombogenic drug.

Embodiment 42

The system of Embodiment 30, wherein at least one of the plurality of components comprises an expansion-limiting coating configured to control an expansion rate of the component.

Embodiment 43

The system of Embodiment 30, wherein each of the plurality of components is different sizes from another of the plurality.

Embodiment 44

The system of Embodiment 30, wherein each of the plurality of components is different shapes from another of the plurality.

Embodiment 45

The system of Embodiment 30, wherein a first of the plurality of components and a second of the plurality of components have mating structures configured to abut each other in a complementary configuration and restrict at least degrees of freedom of motion of each of the first and second of the plurality of components.

Embodiment 46

A device for treatment of an aneurysm, comprising a foam component having a region of variable average porosity and a radiopaque marker, the marker being visible under imaging and positionable relative to the region so as to facilitate identification and orientation of the component when implanted into the aneurysm from a catheter, the component being expandable from a compressed configuration to an expanded configuration when released into the aneurysm.

Embodiment 47

The device of Embodiment 46, wherein the region comprises a first section and a second section having an average porosity different from an average porosity of the first material.

Embodiment 48

The device of Embodiment 47, wherein the region further comprises a third section adjacent to the second section, the third section having an average porosity different from the porosity of the second section.

Embodiment 49

The device of Embodiment 48, wherein the second section is coupled to the third section by chemical bonding, by thermal bonding, or by mechanical crimping.

Embodiment 50

The device of Embodiment 48, wherein the third section porosity is different from the first section porosity.

Embodiment 51

The device of Embodiment 46, wherein the region comprises a first material and a second material different from the first material, the first and second materials being coupled to each other.

Embodiment 52

The device of Embodiment 51, wherein the region further comprises a third material different from the first material.

Embodiment 53

The device of Embodiment 46, wherein the marker comprises a material blended into the component such that the component is visible under imaging.

Embodiment 54

The device of Embodiment 53, wherein the marker comprises bismuth or tantalum blended with a foam material to form the component.

Embodiment 55

The device of Embodiment 46, wherein the marker is coupled to an exterior of the component.

Embodiment 56

The device of Embodiment 55, wherein the marker comprises a coating or a material that is bonded or mechanically coupled to the component.

Embodiment 57

The device of Embodiment 46, wherein a shape of the component is selected from the group consisting of cylinders, hemispheres, polyhedrons, prolate spheroids, oblate spheroids, plates, bowls, hollow structures, clover shapes, non-spherical surface of revolution, and combinations thereof.

Embodiment 58

The device of Embodiment 57, further comprising a second foam component having a shape selected from the group consisting of spheres, cylinders, hemispheres, polyhedrons, prolate spheroids, oblate spheroids, plates, bowls, hollow structures, clover shapes, non-spherical surface of revolution, and combinations thereof.

Embodiment 59

The device of Embodiment 58, wherein the foam component and the second foam component are different sizes from each other.

Embodiment 60

The device of Embodiment 58, wherein the foam component and the second foam component are different shapes from each other.

Embodiment 61

The device of Embodiment 58, wherein the foam component and the second foam component have mating structures configured to abut each other in a complementary configuration and restrict at least degrees of freedom of motion of each of the foam component and the second foam component.

Embodiment 62

The device of Embodiment 58, further comprising a plurality of additional foam components having substantially spherical shapes.

Embodiment 63

A method for treatment of an aneurysm, comprising: advancing a foam component through a catheter lumen, the component comprising a first section having a different average porosity than an average porosity of a second section; releasing the component into the aneurysm; allowing the component to expand from a compressed configuration to an expanded configuration within the aneurysm; and positioning the component within the aneurysm such that the first section is positioned away from the aneurysm neck and the second section is positioned adjacent to a neck of the aneurysm.

Embodiment 64

The method of Embodiment 63, wherein the positioning comprises rotating the component.

Embodiment 65

The method of Embodiment 63, wherein the positioning comprises maintaining a position of the component relative to the aneurysm neck during expansion to the expanded configuration.

Embodiment 66

The method of Embodiment 63, wherein the aneurysm is disposed adjacent at bifurcation of a parent vessel into two efferent vessels, and wherein the positioning further comprises positioning the second section adjacent to the bifurcation and permitting flow through the bifurcation and into at least one of the first or second efferent vessels.

Embodiment 67

The method of Embodiment 66, wherein the first section comprises an average porosity of between about 1 µm and about 150 µm.

Embodiment 68

The method of Embodiment 66, wherein the second section comprises an average porosity of between about 100 µm and about 200 µm.

Embodiment 69

The method of Embodiment 63, wherein the component further comprises a third section disposed between the first and second sections, the third section having an average porosity different than the porosity of the second section, wherein the positioning comprises positioning the component such that the first section is positioned at a fundus of the aneurysm and the third section is positioned between the fundus and the aneurysm neck.

Embodiment 70

The method of Embodiment 63, wherein the positioning comprises aligning a radiopaque marker relative to the aneurysm to position the second section adjacent to the aneurysm neck.

Embodiment 71

The method of Embodiment 70, wherein the aligning comprises aligning the marker with a fundus of the aneurysm.

Embodiment 72

The method of Embodiment 63, further comprising injecting a liquid embolic material into the aneurysm after positioning the component.

Embodiment 73

The method of Embodiment 63, further comprising implanting a support structure into the aneurysm before releasing the component into the aneurysm, and wherein the releasing comprises releasing the component through a wall of the support structure into the aneurysm.

Embodiment 74

The method of Embodiment 73, wherein the support structure comprises a substantially enclosed interior cavity, and the releasing further comprises releasing the component into the interior cavity.

Embodiment 75

A system for treatment of an aneurysm, comprising: a first foam component being expandable from a compressed configuration to an expanded configuration when released into the aneurysm, the first component having a first shape when in the expanded configuration; and a second foam component, separate from and freely movable relative to the first component, being expandable from a compressed configuration to an expanded configuration when released into the aneurysm, the second component having a second shape when in the expanded configuration; wherein at least one of the first and second shapes is selected from the group consisting of cylinders, hemispheres, polyhedrons, prolate spheroids, oblate spheroids, plates, bowls, hollow structures, clover shapes, non-spherical surface of revolution, and combinations thereof.

Embodiment 76

The system of Embodiment 75, wherein the first and second shapes are different from each other.

Embodiment 77

The system of Embodiment 75, wherein the first and second components are different sizes from each other.

Embodiment 78

The system of Embodiment 75, further comprising a third foam component, the third component having a third shape different from the first shape.

Embodiment 79

The system of Embodiment 78, wherein the third shape is substantially spherical.

Embodiment 80

The system of Embodiment 78, wherein the first, second, and third components are different sizes from each other.

Embodiment 81

The system of Embodiment 78, wherein the first, second, and third components have different shapes from each other.

Embodiment 82

The system of Embodiment 75, further comprising third, fourth, and fifth foam components, each of the third, fourth, and fifth components having shapes different from those of the first and second shapes.

Embodiment 83

The system of Embodiment 75, further comprising third, fourth, and fifth foam components, each of the third, fourth, and fifth components having sizes different from those of the first and second components.

Embodiment 84

The system of Embodiment 75, wherein the first and second components have first and second mating structures configured to abut each other in a complementary configuration.

Embodiment 85

The system of Embodiment 84, wherein the mating structures can operate to restrict at least two degrees of freedom of motion of the other component.

Embodiment 86

The system of Embodiment 84, wherein in the complementary configuration, the first component restricts at least two degrees of freedom of motion of the second component.

Embodiment 87

The system of Embodiment 84, wherein in the complementary configuration, the first component restricts at least three degrees of freedom of motion of the second component.

Embodiment 88

The system of Embodiment 87, wherein the first component restricts four, five, or six degrees of freedom of motion of the second component.

Embodiment 89

The system of Embodiment 84, wherein in the complementary configuration, the first and second components are interconnected to form a composite structure.

Embodiment 90

The system of Embodiment 84, wherein in the complementary configuration, the first and second components are interconnected to form a composite structure, and wherein the first and second components have different average porosities from each other.

Embodiment 91

The system of Embodiment 84, further comprising a third foam component having a third mating structure configured to abut at least the first mating structure, wherein in the complementary configuration, the first component restricts at least two degrees of freedom of motion of the third component.

Embodiment 92

The system of Embodiment 91, wherein the first component restricts four, five, or six degrees of freedom of motion of the third component.

Embodiment 93

The system of Embodiment 75, wherein the first and second components have different average porosities from each other.

Embodiment 94

The system of Embodiment 75, wherein the first component comprises a first coating and the second component is substantially free of the first coating.

Embodiment 95

The system of Embodiment 75, wherein the component further comprises a bioactive coating.

Embodiment 96

The system of Embodiment 95, wherein the bioactive coating comprises a thrombogenic drug.

Embodiment 97

The system of Embodiment 75, wherein the component further comprises an expansion-limiting coating configured to control an expansion rate of the component.

Embodiment 98

A system for treatment of an aneurysm, comprising a plurality of separate and independently expandable components each being expandable from a compressed configuration to an expanded configuration when released into the aneurysm, each of the components having shapes different from each other, wherein the shapes are selected from the group consisting of cylinders, hemispheres, polyhedrons, prolate spheroids, oblate spheroids, plates, bowls, hollow structures, clover shapes, non-spherical surface of revolution, and combinations thereof.

Embodiment 99

The system of Embodiment 98, wherein the components are different sizes from each other.

Embodiment 100

The system of Embodiment 98, further comprising at least one additional component that is substantially spherical.

Embodiment 101

The system of Embodiment 98, further comprising a plurality of additional components that are substantially spherical.

Embodiment 102

The system of Embodiment 101, wherein the plurality of additional components are different sizes from each other.

Embodiment 103

The system of Embodiment 98, wherein at least two of the components have mating structures configured to abut each other in a complementary configuration for restricting freedom of motion of the components.

Embodiment 104

The system of Embodiment 103, wherein the components each have mating structures configured to abut each other in a complementary configuration.

Embodiment 105

The system of Embodiment 104, wherein in the complementary configuration, the components are interconnected to form a composite structure.

Embodiment 106

The system of Embodiment 103, wherein in the complementary configuration, the components are interconnected to form a composite structure, and wherein the components have different porosities from each other.

Embodiment 107

A method for treatment of an aneurysm, comprising: positioning a distal opening of a catheter adjacent to an aneurysm; and releasing a plurality of separate and independently foam components into the aneurysm; wherein shapes of the plurality of components are selected from the group consisting of cylinders, hemispheres, polyhedrons, prolate spheroids, oblate spheroids, plates, bowls, hollow structures, clover shapes, non-spherical surface of revolution, and combinations thereof.

Embodiment 108

The method of Embodiment 107, wherein the releasing comprises releasing the plurality of components based on a shape of the aneurysm.

Embodiment 109

The method of Embodiment 108, further comprising selecting the plurality of components based on the shape of the aneurysm.

Embodiment 110

The method of Embodiment 107, wherein the releasing comprises interconnecting at least two components to create a composite structure.

Embodiment 111

The method of Embodiment 107, wherein the releasing comprises releasing the plurality of components into the aneurysm to fill the aneurysm such that as a composite, the plurality of components provides a lower porosity adjacent to a neck of the aneurysm relative to a fundus of the aneurysm.

Embodiment 112

The method of Embodiment 107, further comprising imaging the aneurysm.

Embodiment 113

The method of Embodiment 112, wherein the imaging comprises determining a shape of the aneurysm to select the plurality of components.

Embodiment 114

The method of Embodiment 112, further comprising repositioning a first of the plurality of components within the aneurysm after the first component has been released into the aneurysm.

Embodiment 115

The method of Embodiment 114, wherein the repositioning comprises repositioning the first component such that the plurality of components, as a composite, is arranged within the aneurysm to provide a lower porosity adjacent to a neck of the aneurysm relative to a fundus of the aneurysm.

Embodiment 116

The method of Embodiment 107, further comprising, prior to releasing the plurality of components into the aneurysm, implanting a framing device into the aneurysm.

Embodiment 117

The method of Embodiment 116, wherein the releasing comprises releasing the plurality of components into a cavity of the framing device.

Embodiment 118

A method for treatment of an aneurysm, comprising: positioning a distal opening of a catheter adjacent to the aneurysm; and advancing a framing device into the aneurysm, the framing device having an interior cavity and an exterior surface for contacting a wall of the aneurysm; and while at least a portion of the device exterior surface is in contact with the aneurysm wall, releasing at least one expandable component into the device cavity; wherein the framing device comprises at least one of a foam or a braided structure.

Embodiment 119

The method of Embodiment 118, wherein the aneurysm is a saccular aneurysm and before releasing the at least one expandable component, the device is expanded such that the exterior surface contacts an inner surface of the aneurysm having a cross-sectional profile greater than a passing profile of a neck of the aneurysm.

Embodiment 120

The method of Embodiment 118, wherein the releasing comprises causing the device to expand into contact with the aneurysm wall.

Embodiment 121

The method of Embodiment 118, wherein the device comprises a substantially closed three-dimensional expanded shape.

Embodiment 122

The method of Embodiment 118, wherein the component comprises at least one of a foam, a coil, or a braided structure.

Embodiment 123

The method of Embodiment 121, wherein the three-dimensional shape is selected from the group consisting of spheres, cylinders, hemispheres, polyhedrons, prolate spheroids, oblate spheroids, non-spherical surface of revolution, and combinations thereof.

Embodiment 124

The method of Embodiment 118, wherein the device comprises for quadrants, and the releasing comprises causing at least a portion of each quadrant to contact the aneurysm wall.

Embodiment 125

The method of Embodiment 124, wherein the device comprises a substantially spherical expanded shape.

Embodiment 126

The method of Embodiment 118, wherein the device comprises an opening to the device cavity, and the releasing comprises injecting the at least one expandable component into the device cavity through the device aperture.

Embodiment 127

The method of Embodiment 126, wherein the device comprises a braided material and the opening is an opening formed between filaments of the braided material.

Embodiment 128

The method of Embodiment 126, wherein the framing device has a closed end and an open end opposite the closed end, the open end forming the opening, and wherein the releasing advancing comprises aligning the opening with a neck of the aneurysm.

Embodiment 129

The method of Embodiment 128, wherein the open end comprises a plurality of filament ends extending into the device cavity and forming the opening, the plurality of filament ends collectively forming a tubular portion extending into the device cavity, wherein the releasing comprises permitting the at least one expandable component to expand within the device cavity such that the tubular portion is deflected into contact with an inner wall of the device, thereby closing the opening.

Embodiment 130

The method of Embodiment 118, wherein the releasing comprises releasing a plurality of expandable components into the aneurysm such that as a composite, the plurality of expandable components provides a lower average porosity adjacent to a neck of the aneurysm relative to an average porosity at a fundus of the aneurysm.

Embodiment 131

The method of Embodiment 118, wherein the at least one expandable component comprises a shape selected from the group consisting of cylinders, hemispheres, polyhedrons, prolate spheroids, oblate spheroids, plates, bowls, hollow structures, clover shapes, non-spherical surface of revolution, and combinations thereof.

Embodiment 132

The method of Embodiment 118, wherein the releasing comprises releasing at least one coil into the device cavity.

Embodiment 133

The method of Embodiment 118, wherein the releasing comprises releasing at least one expandable component into the device cavity.

Embodiment 134

The method of Embodiment 133, wherein the at least one expandable component comprises an expandable composite comprising first and second portions having different porosities from each other.

Embodiment 135

A method for treatment of an aneurysm, comprising: implanting a stent into a lumen of a parent vessel from which an aneurysm arises such that the stent extends across at least a portion of the aneurysm; and releasing at least one expandable component into an inner volume of the aneurysm between a wall of the aneurysm and an outer surface of the stent; wherein the expandable component comprises at least one of a foam or a braided structure.

Embodiment 136

The method of Embodiment 135, wherein the aneurysm comprises a fusiform aneurysm.

Embodiment 137

The method of Embodiment 135, wherein the aneurysm comprises a wide-neck aneurysm.

Embodiment 138

The method of Embodiment 135, wherein the portion comprises a neck.

Embodiment 139

The method of Embodiment 135, wherein the at least one expandable component comprises a plurality of expandable components, and the releasing comprises releasing the plurality based on relative sizes of the expandable components.

Embodiment 140

The method of Embodiment 139, further comprising selecting the at least one expandable component based on the shape of the inner volume.

Embodiment 141

The method of Embodiment 140, wherein the at least one expandable component comprises a shape selected from the group consisting of cylinders, hemispheres, polyhedrons, prolate spheroids, oblate spheroids, plates, bowls, hollow structures, clover shapes, non-spherical surface of revolution, and combinations thereof.

Embodiment 142

The method of Embodiment 135, wherein the at least one expandable component comprises a first portion having an average porosity greater than that of a second portion thereof, and the releasing comprises positioning the at least one expandable component such that the first portion abuts an outer surface of the stent device and the second portion extends along an inner wall of the aneurysm.

Embodiment 143

The method of Embodiment 135, wherein the releasing comprises releasing a plurality of expandable components into the inner volume.

Embodiment 144

The method of Embodiment 135, wherein the aneurysm inner volume extends around a circumference of the stent device, and the releasing comprises depositing a plurality of expandable components into the inner volume around the circumference of the stent device.

Embodiment 145

The method of Embodiment 144, wherein at least one of the plurality of expandable components comprises a flat or cylindrically shaped surface, and the releasing comprises positioning the at least one of the plurality of expandable components such that the flat or cylindrically shaped surface substantially conforms to an outer surface of the stent device.

Embodiment 146

A system for treatment of an aneurysm, comprising: an intrasaccular device comprising first and second expandable components adapted to transition from a compressed configuration to an expanded configuration when deployed into the aneurysm, the first and second components being interconnected by a non-helical coupling such that the first and second components can be advanced as an interconnected unit, into the aneurysm; wherein the first component comprises at least one of a shape or an average porosity different from a shape or an average porosity of the second component.

Embodiment 147

The system of Embodiment 146, wherein the first component shape is selected from the group consisting of cylinders, hemispheres, polyhedrons, prolate spheroids, oblate spheroids, plates, bowls, hollow structures, clover shapes, non-spherical surface of revolution, and combinations thereof.

Embodiment 148

The system of Embodiment 146, wherein the second component comprises a substantially spherical shape.

Embodiment 149

The system of Embodiment 146, wherein at least one of the first or second components comprises a foam or a braided structure.

Embodiment 150

The system of Embodiment 146, wherein at least one of the first or second components comprises a coil.

Embodiment 151

The system of Embodiment 146, wherein the first component comprises an average porosity of between about 1 µm and about 100 µm and the second component comprises an average porosity of between about 100 µm and about 200 µm

Embodiment 152

The system of Embodiment 146, further comprising a third component interconnected with the second component such that the first, second, and third components are interconnected in series.

Embodiment 153

The system of Embodiment 146, wherein the coupling interconnecting the first and second components comprises a filament.

Embodiment 154

The system of Embodiment 146, wherein the coupling has a preset shape such that in an expanded position, the first and second components are spaced relative to each other at a preset orientation.

Embodiment 155

The system of Embodiment 146, further comprising an introducer sheath configured to receive the device therein such that the device can be loaded into the guide catheter for delivery to the aneurysm.

Embodiment 156

A system for treatment of an aneurysm, comprising: an intrasaccular device comprising at least three expandable components adapted to transition from a compressed configuration to an expanded configuration when deployed into the aneurysm, each of the at least three components being interconnected to at least two of the at least three components such that at least three expandable components can be advanced as an interconnected unit, into the aneurysm.

Embodiment 157

The system of Embodiment 156, wherein the at least three expandable components comprises at least four expandable components.

Embodiment 158

The system of Embodiment 157, wherein at least two of the at least four expandable components is interconnected with at least three of the at least four expandable components such that the device comprises a multi-planar shape.

Embodiment 159

The system of Embodiment 156, wherein the at least three components are interconnected by filaments.

Embodiment 160

The system of Embodiment 156, wherein at least three components are interconnected by filaments having preset shapes such that in an expanded position, the at least three components are spaced relative to each other at a preset orientation.

Embodiment 161

The system of Embodiment 156, wherein the device comprises at least one central expandable component positioned such that, when the device is in an expanded configuration, the central expandable component is centrally interconnected with a plurality of the expandable components.

Embodiment 162

The system of Embodiment 161, wherein the at least one central expandable component has an expanded size greater than an expanded size of each remaining one of the plurality of components.

Embodiment 163

The system of Embodiment 161, wherein the at least one central expandable component has an average porosity greater than an average porosity of each remaining one of the plurality of the components.

Embodiment 164

The system of Embodiment 158, wherein the multi-planar shape comprises a polyhedron.

Embodiment 165

The system of Embodiment 164, wherein the multi-planar shape comprises a pyramid.

Embodiment 166

The system of Embodiment 164, wherein the multi-planar shape comprises a prism.

Embodiment 167

The system of Embodiment 156, wherein a first component of the at least three components comprises a shape or an average porosity different than that of a second component of the at least three components.

Embodiment 168

The system of Embodiment 156, wherein the first component shape is selected from the group consisting of cylinders, hemispheres, polyhedrons, prolate spheroids, oblate spheroids, plates, bowls, hollow structures, clover shapes, non-spherical surface of revolution, and combinations thereof.

Embodiment 169

The system of Embodiment 156, wherein the second component comprises a substantially spherical shape.

Embodiment 170

The system of Embodiment 156, wherein the first component comprises an average porosity of between about 1 μm and about 100 μm, and the second component comprises an average porosity of between about 100 μm and about 200 μm.

Embodiment 171

The system of Embodiment 156, further comprising an introducer sheath configured to receive the device therein such that the device can be loaded into the guide catheter for delivery to the aneurysm.

Embodiment 172

A method for treatment of an aneurysm, comprising: advancing an intrasaccular device toward the aneurysm through a lumen of a catheter, the device comprising a plurality of expandable components each adapted to transition from a compressed configuration to an expanded configuration when deployed into the aneurysm from the catheter, each of the plurality of components being interconnected by a coupling.

Embodiment 173

The method of Embodiment 172, further comprising: advancing the device into the aneurysm such that a first component is disposed within the aneurysm and a second component, interconnected with the first component by the coupling, is disposed within the catheter lumen; severing the coupling between the first and second components to release the first component into the aneurysm; retaining the second component within the lumen; and withdrawing the catheter.

Embodiment 174

The method of Embodiment 172, further comprising advancing a plurality of expandable components into the aneurysm prior to the severing.

Embodiment 175

The method of Embodiment 172, wherein each of the plurality of components is interconnected in series by the coupling.

Embodiment 176

The method of Embodiment 172, wherein the severing comprises proximally withdrawing the catheter relative to a second catheter such that the coupling between the first and second components is pinched between a distal end of the catheter and a rim of the second catheter.

Embodiment 177

The method of Embodiment 172, wherein the plurality of expandable components is arranged in descending size, and the advancing comprises allowing an initial expandable component deployed into the aneurysm to expand prior to advancing a subsequent expandable component into the aneurysm.

Embodiment 178

The method of Embodiment 177, wherein the advancing comprises observing a fit of expanded components within the aneurysm to determine whether to advance additional components into the aneurysm.

Embodiment 179

The method of Embodiment 178, wherein the device comprises a radiopaque material.

Embodiment 180

The method of Embodiment 178, wherein the couplings between the plurality of expandable components comprise a radiopaque material.

Embodiment 181

The method of Embodiment 178, wherein each of the plurality of expandable components of the device comprises a radiopaque material.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 3 is a schematic view an intrasaccular device having a specific porosity, according to some embodiments.

FIG. 4 is a schematic view of an intrasaccular device comprising two portions having different porosities, according to some embodiments.

FIG. 5 is an enlarged view of a transition zone of the intrasaccular device shown in FIG. 4, wherein the transition zone comprises an immediate transition between different porosities, according to some embodiments.

FIG. 6 is an enlarged view of the transition zone of the intrasaccular device shown in FIG. 4, wherein the transition zone comprises a gradual transition between different porosities, according to some embodiments.

DETAILED DESCRIPTION

Figure 1:
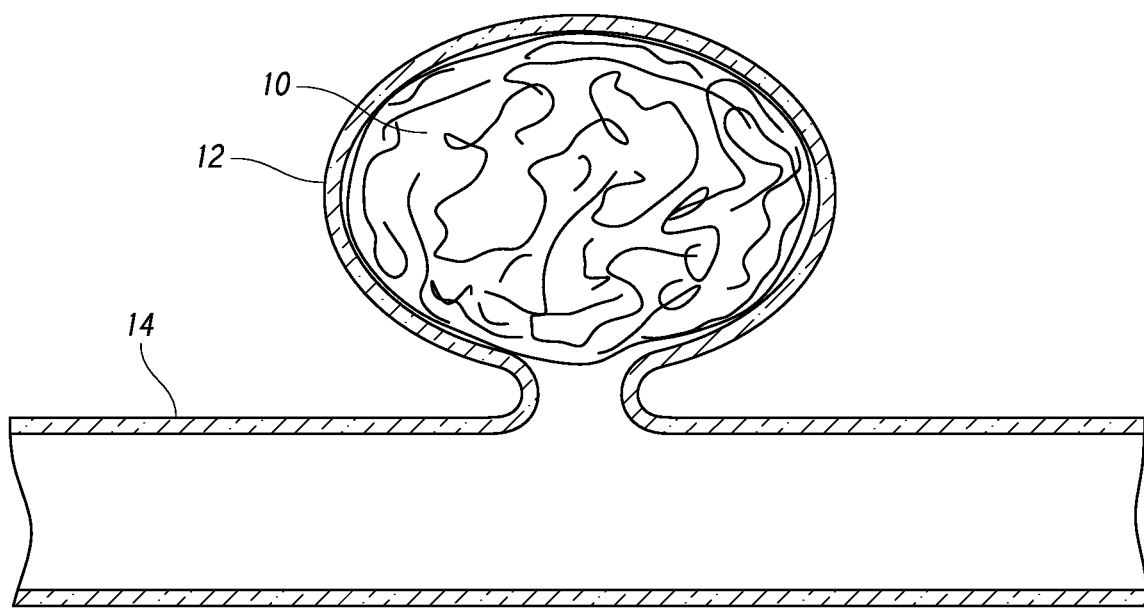
FIG. 1 is a schematic illustration depicting an aneurysm within a blood vessel, into which an intrasaccular device has been implanted, according to some embodiments.

In the following detailed description, numerous specific details are set forth to provide a full understanding of the subject technology. It should be understood that the subject technology may be practiced without some of these specific details. In other instances, well-structures and techniques have not been shown in detail so as not to obscure the subject technology.

Intrasaccular implant devices and procedures for treating aneurysms can be improved by manipulating one or more physical characteristics of the implant material. Such characteristics can include the porosity, composition, material, shape, size, interconnectedness, inter-engagement, coating, etc. By modifying one or more such characteristics, the morphology or attributes of a target aneurysm and orientation of any connecting arteries can be specifically considered and addressed to achieve superior treatment.

According to some embodiments, the porosity, composition, or material of the intrasaccular device can facilitate in the treatment of an aneurysm. The intrasaccular device can comprise an expandable component. The intrasaccular device can expand from a first, compressed configuration to a second, expanded configuration when released into the aneurysm.

Optionally, the intrasaccular device can comprise an expandable component having an average porosity that changes from a first end of the component to a second end opposite the first end. Optionally, the intrasaccular device can comprise a composite structure having first and second sections or materials having different porosities. For example, the first and second sections can be separated by a transition zone. The transition zone can comprise an immediate change in porosity or a gradual transition in which the porosity spatially varies between a first porosity and a second porosity from one end of the transition zone to another, opposite end of the transition zone.

As used herein, "porosity" can generally refer to an average porosity, which can be sampled across a given portion or section of an expandable component. "Porosity" can be defined as the ratio of the volume of the pores of in a component to the volume of the component as a whole. Porosity can be measured by a fluid displacement test. For example, liquid or gas testing can be used, as necessary or desirable, according to skill in the art. In some embodiments, a chromatography chamber can be used to measure displacement of a gas within the chamber, enabling the calculation of an average porosity of a given intrasaccular device or portion thereof. Other methods and systems can be used to measure porosity of portions of or the entirety of an expandable component.

In some embodiments, a composite structure of the intrasaccular device can comprise three materials having different porosities. Further, the composite structure of the intrasaccular device can comprise for, five, six, or more different materials having different porosities.

According to some embodiments, one or more of intrasaccular devices can be released into a target aneurysm and, in some embodiments, specifically oriented relative to the aneurysm ostium or neck and/or one or more perforating vessels (e.g., perforating arteries or arterioles) adjacent to the aneurysm.

In some embodiments, the intrasaccular device can be repositioned within the aneurysm as the device is expanding. The repositioning of the device can allow a clinician to position a lower porosity section of the device adjacent to the neck of the aneurysm. The repositioning of the device can also allow a clinician to position a higher average porosity section of the device adjacent to one or more perforating vessels (e.g., perforating arteries or arterials) adjacent to the aneurysm. The repositioning of the device can also allow a clinician to position a lower porosity portion of the device adjacent to a bifurcation. The repositioning of the device can also allow a clinician to position a higher average porosity portion of the device toward or in the fundus of the aneurysm.

Intrasaccular implant devices and procedures for treating aneurysms disclosed herein can also comprise manipulating a shape or size of the intrasaccular device. According to some embodiments, a single expandable component having a specific or selected shape or size, which can be tailored to the shape or size of the aneurysm, can be implanted into an aneurysm. Further, multiple expandable components, each having such a specific or selected shape or size can also be implanted into an aneurysm. The shape or size of the expandable component(s) can be selected from a variety of spherical or non-spherical shapes. Each shape can be solid or hollow.

According to some embodiments, a composite intrasaccular device can be provided that comprises at least two mating expandable components (e.g., a plurality of interconnectable or engageable expandable components). Each of the expandable components can comprise one or more engagement structures configured to interact with a corresponding engagement structure of another mating expandable component.

For example, the mating expandable components can each comprise an engagement structure configured to interact with a corresponding engagement structure of another mating expandable component. The mating expandable components can be delivered into the aneurysm and arranged in situ such that the engagement structures are aligned and interconnected appropriately such that the expandable components are mated. In some embodiments, the mating of the expandable components can interlock the components as a unit. For example, expansion of a portion of a component within a recess of another component can cause the components to be interlocked with each other. Further, in some embodiments, the mating components can restrict at least one degree of freedom of movement of another component.

According to some embodiments in which a plurality of expandable components is used, the expandable components (whether interconnected by wires or filaments, or not interconnected, thereby moving independently of each other) can be arranged in a pattern to provide a composite component. The composite component can provide desired characteristics that may be difficult to achieve in a single component formed from a single, continuous piece of material.

A variety of delivery systems and procedures can be implemented to deliver an intrasaccular device having a specific size or shape and, in some embodiments, having a plurality of expandable components. Examples of these systems and procedures are discussed further herein.

In accordance with some embodiments of the delivery procedure, the target aneurysm can be imaged and analyzed in order to determine a three-dimensional shape of the aneurysm. Based on the shape of the target aneurysm, one or more expandable components can be selected, having a unique porosity, composition, material, shape, size, interconnectedness, inter-engagement, or coating, etc. Imaging devices can include 3-D CTA or MRI (MRA) imaging, through which the size and shape of the aneurysm can be ascertained. Such imaging can provide a basis for selection of one or more correspondingly shaped intrasaccular device(s) for insertion within the aneurysm. Different combinations of expandable components or their characteristics can be used.

Optionally, in some embodiments, the intrasaccular device can have a predetermined configuration, whether or not the intrasaccular device has only a single or multiple expandable components. The predetermined configuration can be based on typical aneurysm shapes, thereby allowing selection of a specific intrasaccular device. However, individual components of an intrasaccular device can also be arranged based on their properties. Accordingly, the clinician can determine the shape of the aneurysm and create a desired intrasaccular device configuration for treating the aneurysm.

In some embodiments, an expandable component of an intrasaccular device may be molded or manufactured into a variety of geometrical or partial geometrical shapes.

For example, in order to accommodate a variety of aneurysm configurations, the shape or size of the expandable component(s) can be selected from a variety of spherical or non-spherical shapes, including, cylinders, hemispheres, noodles, polyhedrons (e.g., cuboids (types), tetrahedrons (e.g. pyramids), octahedrons, prisms), coils, prolate spheroids, oblate spheroids, plates (e.g., discs, polygonal plates), bowls (e.g, an open container, such as a hollow, hemispherical container or other open, hollow containers, whether hemispherical, rounded, or otherwise), hollow structures (e.g., a container of any shape with an inner cavity or void, which can be, for example, greater in size than a width of any of the walls of the structure), clover shapes (a plurality of radially extending protrusions, having rounded or smooth corners), non-spherical surfaces of revolution (e.g., toruses, cones, cylinders, or other shapes rotated about a center point or a coplanar axis), and combinations thereof. Each shape(s) can be solid or hollow.

In accordance with some embodiments, at least a portion of the intrasaccular device can comprise a coating or material for enhancing therapeutic, expansive, or imaging properties or characteristics of at least one or every expandable component of the intrasaccular device.

In some embodiments, the intrasaccular device can be configured such that an expandable component thereof is coated with a biocompatible material to promote endothelialization or provide a therapeutic effect.

Optionally, the expandable component can also comprise an expansion-limiting coating that slows expansion of the component from its natural rate of expansion to a slower rate of expansion such that in the process of expanding, the position of the component can be adjusted within the aneurysm or the component can be removed from the aneurysm, if necessary. Examples of polymers that can be used as expansion-limiting coatings can include hydrophobic polymers, organic non-polar polymers, PTFE, polyethylene, polyphenylene sulfide, oils, and other similar materials.

Various delivery systems and procedures can be implemented for delivering an intrasaccular device comprising one or more expandable components, as discussed herein. Further, a system and method are provided for delivery of an intrasaccular device to an aneurysm and/or recapturing the device for removal or repositioning.

Intrasaccular implant devices and procedures for treating aneurysms can comprise interconnecting individual components of the intrasaccular device. According to some embodiments, a plurality of expandable components can be interconnected along a wire, filament, or other disconnectable or breakable material. The expandable components can be connected in a linear configuration, a planar matrix, or in a three-dimensional matrix. The expandable components of such interconnected linear, planar, or three-dimensional matrices can be sized and configured in accordance with desired porosity, size, shape, radiopacity, or other characteristics disclosed herein.

In some embodiments, methods are provided by which interconnected expandable components can be released into an aneurysm. The interconnected components can be preconfigured (e.g., a plurality of components can be joined together to form a single, unitary device, or a select plurality of components can be removed from a larger strand or array of components) prior to implantation and later inserted into a delivery catheter. Thereafter, the entire strand or assembly of interconnected expandable components of the intrasaccular device can be ejected or released into the aneurysm and allowed to expand within the aneurysm.

However, in accordance with some embodiments, an entire strand or array of components can be loaded into a delivery catheter, and while implanting and observing the packing behavior, a clinician can determine that a select portion of the interconnected expandable components is sufficient for a given aneurysm. Thereafter, the select portion of the interconnected expandable components can be broken or cut in situ so as to be released into the aneurysm.

Additionally, although in some embodiments, a single expandable component can be used alone to fill the aneurysm and provide a desired packing density, a plurality of expandable components can also be used to fill the aneurysm and provide a desired packing density. Optionally, a liquid embolic and/or a framing component can be used in combination with one or more expandable components to facilitate delivery, engagement with the aneurysm, or increase of the packing density. Any of these embodiments can allow increased packing density to avoid recanalization of the aneurysm.

Referring now to the drawings, FIG. 1 illustrates an embodiment of an intrasaccular device 10 positioned within an aneurysm 12 in a blood vessel 14. The intrasaccular device 10 can be particularly adapted for use in the tortuous neurovasculature of a subject for at least partial deployment in a cerebral aneurysm.

A cerebral aneurysm may present itself in the shape of a berry, i.e., a so-called berry or saccular aneurysm, which is a bulge in the neurovascular vessel. Berry aneurysms may be located at bifurcations or other branched vessels. Other types of aneurysms, including fusiform aneurysms, can also be treated using embodiments of the intrasaccular devices disclosed herein.

The intrasaccular device 10 can comprise at least one expandable component. In some embodiments, the intrasaccular device 10 can comprise a plurality of expandable components. Further, a given expandable component of the intrasaccular device 10 can have one or more different characteristics than another of the expandable components of the intrasaccular device 10.

An expandable component can be formed from a material that can be highly compressed and later expanded when released into the aneurysm and contacted by a fluid, such as a fluid within the aneurysm. In some embodiments, the expandable component can be formed at least in part of biocompatible, solid foam. As disclosed herein, "foam" can include a solid or semisolid gel, a swellable material (whether swellable upon hydration or swellable/self-expanding without hydration), a material having pores and interstices. "Foam" can include hydrophobic or hydrophilic materials. "Foam" can also include materials that can be highly compressed and configured to expand upon contact with a fluid, upon exposure to a thermal agent, upon exposure to a chemical agent, or self-expanding, upon release from engagement with the delivery mechanism. In some embodiments, the foam material can be configured to expand by about two, three, four, five, six, seven, eight, nine, ten, eleven, twelve, thirteen, fourteen, fifteen, sixteen, seventeen, eighteen, nineteen, twenty, or more times its collapsed size when expanding to its expanded size.

Figure 2:
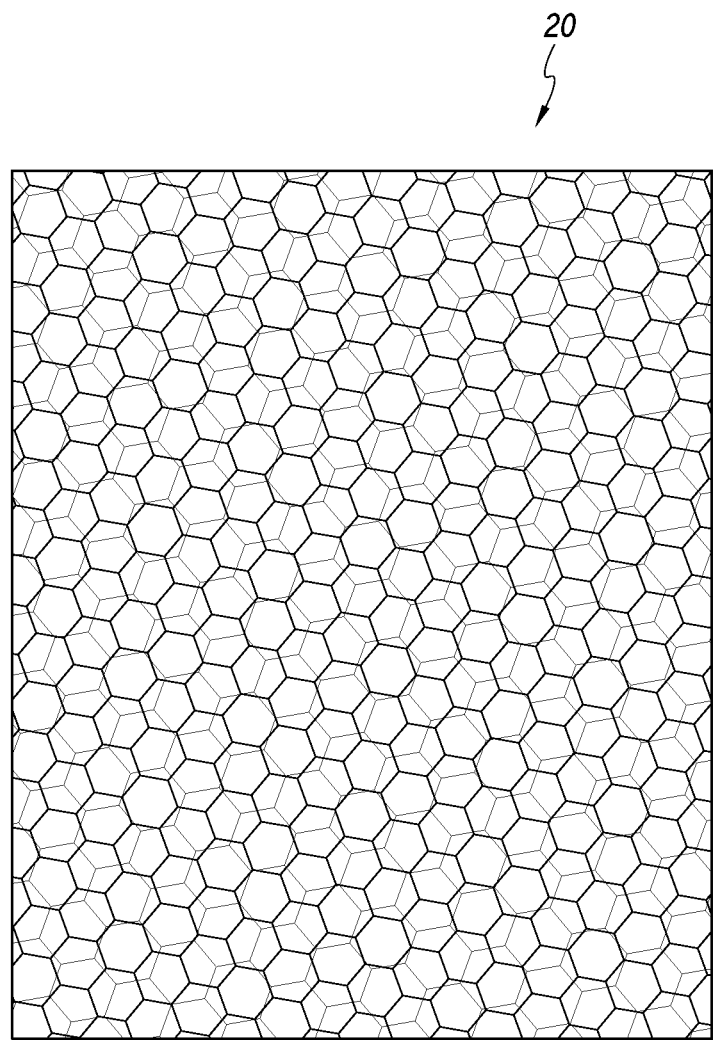
FIG. 2 is a schematic view of reticulated foam, which can be used in the intrasaccular device accordance with some embodiments.

For example, FIG. 2 illustrates a schematic view of a foam material 20. Suitable foam materials can comprise biocompatible foams such as a PVA (polyvinyl alcohol). Further, suitable foam materials can comprise reticulated foam. "Reticulated" foam can, in some embodiments, comprise a random arrangement of holes that has irregular shapes and sizes or a nonrandom arrangement of holes that has regular, patterned shapes and sizes. Suitable foam is also known under the trade name PacFoam, made available through UFP Technologies of Costa Mesa, Calif. In some embodiments, the foam material from which the expandable component is formed can be configured to include at least about 20 pores per inch ("PPI"), at least about 30 PPI, at least about 40 PPI, at least about 50 PPI, at least about 60 PPI, at least about 70 PPI, or at least about 80 PPI, or combinations thereof.

Other materials can also be used to form one or more portions of an intrasaccular device or an expandable component thereof. Such materials can include, but are not limited to polyvinyl alcohol (PVA) materials, water-soluble synthetic polymers, such as poly ethylene glycol (PEG), polyvinyl pyrrolidone (PVP), and other similar materials.

The porosity of the expandable component may vary along any portion(s) thereof, including any combination of pore sizes of 1 micron or greater. Further, the pore sizes can range from about 1 µm to about 400 from about 5 µm to about 300 from about 8 µm to about 200 from about 10 µm to about 150 from about 15 µm to about 80 or in some embodiments, from about 20 µm to about 50 Further, at least a portion or section of the device can comprise an average porosity of between about 1 µm and about 150 Further, at least a portion or section can comprise an average porosity of between about 100 µm and about 200 Furthermore, at least a portion or section can comprise an average porosity of between about 200 and about 300 When a composite expandable component is formed using multiple sections or portions, each section or portion can have an average porosity within any of the ranges discussed above.

According to some embodiments, in a compressed state, an expandable component of the intrasaccular device may be compressed down to 50%, 40%, 30%, 20%, 10% or less of its expanded state (which can be measured by its maximum diameter or cross-sectional dimension) for delivery through a standard microcatheter. In some embodiments, the foam material can be configured to expand by about two to twenty times its collapsed size when expanding to its expanded size.

In the event the intrasaccular device is not self-expandable, but expandable through a chemical reaction, a chemical may be introduced within the lumen of the delivery catheter for delivery to the intrasaccular device. In the alternative, the delivery catheter may include a separate lumen for introduction of the catalyst. Thermally expansive foam may be activated through introduction of heated saline or some other suitable biocompatible fluid through any of the aforementioned lumens of the delivery catheter. In the alternative, a heating element may be incorporated within the delivery catheter to deliver heat to the foam structure to cause corresponding expansion. A suitable heating element, identified schematically as reference numeral, may include resistive element(s), a microwave antenna, radio-frequency means, ultrasonic means or the like.

As noted above, some embodiments of the expandable component can be configured to provide a specific porosity profile. The porosity profile can comprise a single, consistent average porosity throughout the entire expandable component, or multiple average porosity zones, portions, or materials having different average porosities that are joined to form a composite expandable component.

For example, the embodiment illustrated in FIG. 3 can be configured to have a low average porosity structure. For purposes of illustration, low porosity structures are illustrated in the figures using hexagonal patterns with larger spaces compared to hexagonal patterns with smaller spaces, which are used to illustrate medium and high porosity structures. Low porosity structures can provide higher packing densities, which can facilitate thrombogenesis by providing higher resistance to flow therethrough. When such low porosity structures are implanted into an aneurysm, such structures can substantially pack the aneurysm with a relatively high packing density, thereby isolating the aneurysm from the parent vessel and minimizing blood flow velocity within the aneurysm while supporting the aneurysm wall.

Conversely, as porosity increases, the packing density decreases, which compared to low porosity structures, provides less support for thrombogenesis due to lower resistance to flow therethrough. Nevertheless, the realization of some embodiments disclosed herein is that high porosity structures can also support the aneurysm wall, beneficially aid in healing and thrombogenesis for select aneurysm morphologies, permit flow to other vessels (e.g., branch vessels, perforating arteries, or arterioles), and/or permit the introduction of other materials, such as a liquid embolic, etc.

Further, in some embodiments, composite, variable, or multi-porosity expandable components (whether using a single expandable component having multiple porosities or using multiple expandable components each having different porosities) can advantageously allow the intrasaccular device to mimic natural function of the vasculature while promoting healing through thrombogenesis, pressure moderation or reduction, or aneurysm deflation. Further, in embodiments using a single expandable component, the single expandable component can be configured to advantageously secure the intrasaccular device within a wide-neck aneurysm by facilitating engagement with a sufficient amount of the aneurysm wall, thereby avoiding dislodgement or herniation of the device from the aneurysm into the parent vessel.

FIG. 3 illustrates an expandable component 50 having a relatively less dense or high porosity due to a larger pore size. As noted above, the foam component 50 can permit some blood flow therethrough to maintain branch vessels while still providing support for the aneurysm wall. Further, in accordance with some embodiments, the expandable component 50 or a portion of the expandable component 50 can be packed with a liquid embolic during or subsequent to placement of the intrasaccular device. The injection of a liquid embolic can increase the overall packing density within the expandable component 50.

One suitable liquid embolic is the Onyx™ liquid embolic system manufactured by Covidien LP, Irvine, Calif. Onyx™ liquid embolic system is a non-adhesive liquid used in the treatment of brain arteriovenous malformations. Onyx™ liquid embolic system is comprised of an EVOH (ethylene vinyl alcohol) copolymer dissolved in DMSO (dimethyl sulfoxide), and suspended micronized tantalum powder to provide contrast for visualization under fluoroscopy. Other liquid embolic solutions are also envisioned.

FIGS. 4-9 illustrate additional embodiments of expandable components. For example, FIG. 4 illustrates an expandable component 60 having first and second portions 62, 64. The first and second portions 62, 64 can be formed from different materials. For example, the first portion 62 can comprise a higher average porosity first material, and the second portion 64 can comprise a lower average porosity second material. The first and second portions 62, 64 can be coupled to each other by any chemical, thermal, or mechanical bonding methods known in the art or arising hereafter. The first and second portions 62, 64 can be permanently attached to each other or releasably, upon expansion, attached to each other.

FIGS. 5-6 illustrate enlarged views of a transition zone 66 of the expandable component 60 of FIG. 4. In accordance with some embodiments, FIG. 5 illustrates that a transition zone 66a can comprise an immediate, abrupt transition between the porosities of the first and second portions 62, 64. The transition zone 66a provides an open flow pathway between the first and second portions 62, 64. Thus, the transition zone 66a may not act as a barrier to fluid flow. However, in some embodiments, the transition zone 66a can provide at least a partial or full barrier to fluid flow between the first and second portions 62, 64. In such embodiments, the composite structure of the expandable component 60 may incorporate individual, separately formed segments or sections of material that are later joined together to create a composite unit or whole. The individual segments or first and second portions 62, 64 may comprise the same material (such as any of those mentioned herein), or incorporate a combination of different materials. The first and second portions 62, 64 may be bonded by any chemical, thermal, or mechanical methods known in the art.

FIG. 6 illustrates that a transition zone 66b can comprise an intermediate portion 68 having an average porosity that is higher than the average porosity of the second section 64, but lower than the average porosity of the first section 62. The transition zone 66b provides an open flow pathway between the first, second, and/or intermediate portions 62, 64, 68. Thus, similar to the transition zone 66a, the transition zone 66b may not act as a barrier to fluid flow. However, in some embodiments, the transition zone 66b can provide at least a partial or full barrier to fluid flow between the first, second, and/or intermediate portions 62, 64, 68. In such embodiments, the intermediate portion 68 can have a porosity that gradually transitions spatially from a low porosity to a high porosity, or vice versa. The transition zone 66b can be formed by varying the gas used in the fabrication of the variable porosity structure. Further, during manufacturing of the expandable component 60, regions within the blank can be identified based on an average porosity and the expandable component can be trimmed therefrom. In some embodiments, certain regions can be identified that have a porosity that varies spatially from one end of the region to another, opposite end.

Figure 7:
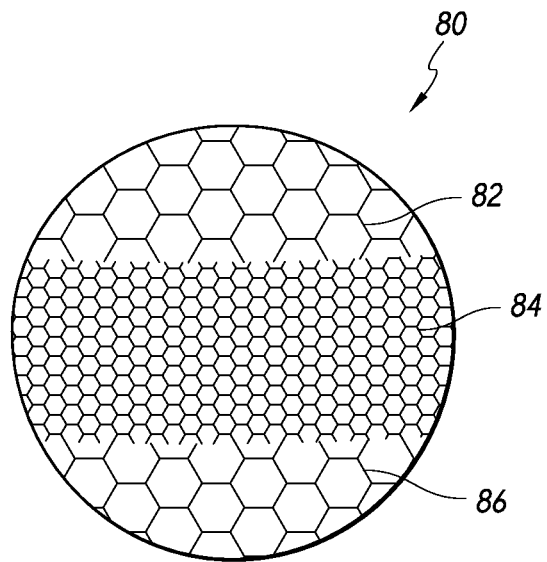
FIG. 7 is a schematic view of an intrasaccular device comprising three portions arranged in a specific porosity profile, according to some embodiments.
Figure 8:
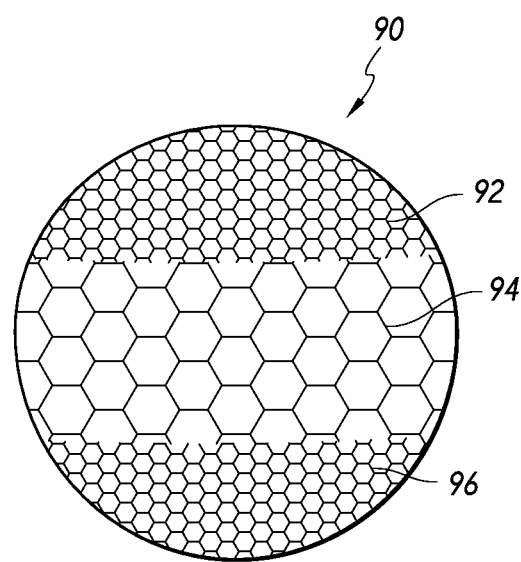
FIG. 8 is a schematic view of an intrasaccular device comprising three portions arranged in a specific porosity profile, according to some embodiments.
Figure 9:
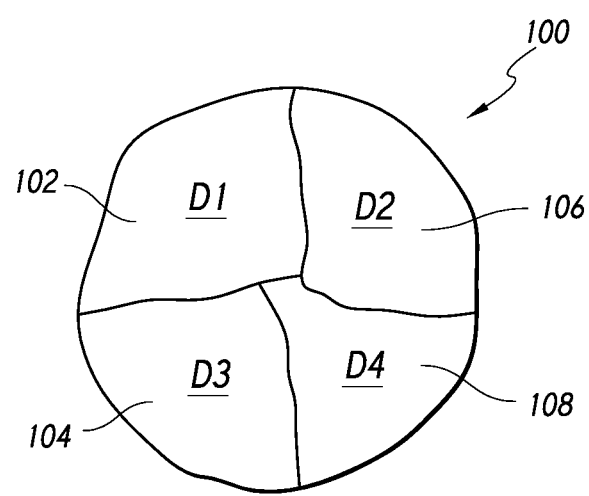
FIG. 9 is a schematic view of an intrasaccular device comprising four portions having different porosities, according to some embodiments.

FIGS. 7-9 illustrate schematic views of additional embodiments of expandable components shown in FIGS. 1-4. These figures illustrate expandable components that each include a composite structure having two or more foam segments with different respective porosities (or pore densities), sizes, and/or shapes.

For example, FIG. 7 illustrates an expandable component 80 having first, second, and third portions 82, 84, 86. The second portion 84 can comprise a lower porosity than the first and third portions 82, 86. In some embodiments, the first and third portions 82, 86 can comprise the same porosity (e.g., the first and third portions 82, 86 can comprise the same material or be formed or cut from the same material). However, in some embodiments, the first and third portions 82, 86 can comprise different porosities (e.g., the first and third portions 82, 86 can comprise different materials or be formed or cut from different materials). Additionally, the first, second, and third portions 82, 84, 86 can comprise different sizes and/or shapes or have substantially identical sizes and/or shapes. Size and shape characteristics can be configured as discussed below, in accordance with some embodiments.

FIG. 8 similarly illustrates an expandable component 90 having first, second, and third portions 92, 94, 96. In general, the second portion 94 comprises a higher porosity than the first and third sections 92, 96. Additionally, FIG. 9 also illustrates expandable component 100 having first, second, third, and fourth sections 102, 104, 106, 108, which can each have distinct porosities, shapes, and/or sizes. The porosity, size, or shape of the portions of the expandable components 90, 100 can be configured as similarly discussed above with respect to FIG. 7. Accordingly, the discussion of such characteristics will not be repeated except to indicate that FIGS. 8-9 illustrate that some embodiments can incorporate varied porosities, sizes, and shapes different from those illustrated FIG. 7.

The foam composites may be formed to provide different support and/or flow profiles. As addressed herein, a material, such as bismuth or tantalum, can be blended with the foam to provide radiopacity. Also, radiopaque markers can be attached to the foam by bonding or mechanically crimping them to the foam.

As noted above, in some embodiments, only a single expandable component would be required for introduction into an aneurysm. In some embodiments, this may prove advantageous over conventional methodologies such as the insertion of, for example, multiple embolic coils, by significantly reducing time for performance of the embolization procedure.

Additionally, in some embodiments, multiple expandable components can be provided for insertion into an aneurysm. For example, a plurality of expandable components, having different average porosities, can be implanted into an aneurysm and have a composite or cumulative porosity profile spatially across the aneurysm, which can allow the plurality of expandable components to operate as a unit in much the same way as a single expandable component, if packing the same aneurysm itself, would operate. Such embodiments are discussed in greater detail below in FIGS. 36-42. The expandable components can be arranged and positioned within a lumen of the catheter or otherwise arrange for delivery into the aneurysm. The size of each expandable component can be compressed to a fraction of its normal, expanded size and delivered into the target aneurysm.

Further, in some embodiments, the expandable component(s) can include one or more flow regions. The flow region can be used alone or combination with any of the variable porosity profiles disclosed herein, including those illustrated in FIGS. 4-9.

Figure 10:
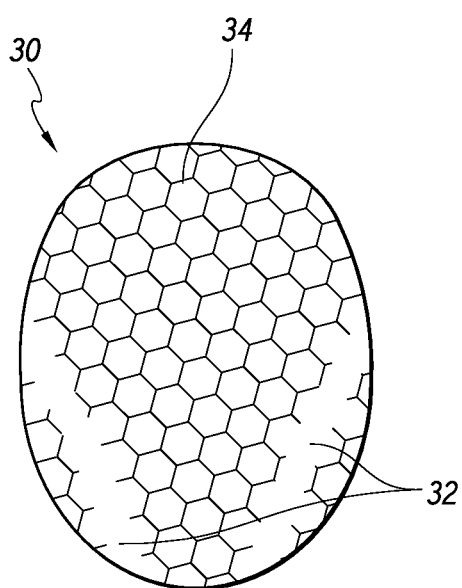
FIG. 10 is a schematic view of an intrasaccular device having channels extending therethrough, according to some embodiments.
Figure 11:
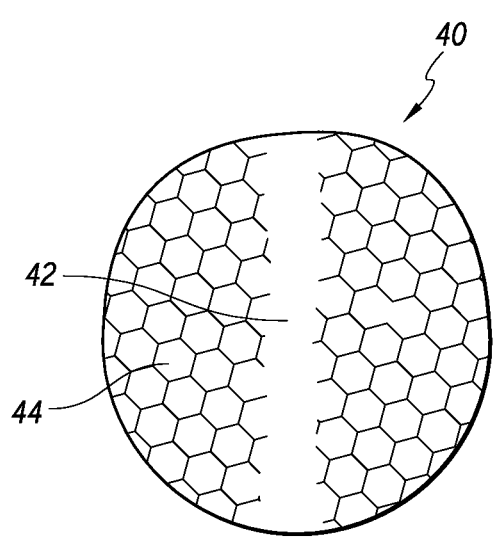
FIG. 11 is a schematic view of an intrasaccular device having a channel extending therethrough, according to some embodiments.

For example, FIGS. 10-11 illustrate expandable components having at least one flow region. FIG. 10 illustrates an expandable component 30 having a pair of flow regions 32 formed in a body 34. FIG. 11 similarly illustrates another embodiment of an expandable component 40 having a single flow region 42 formed in a body 44. While the body 34, 44 can have a substantially constant porosity that impedes fluid flow and generally promotes thrombogenesis, the flow regions 32, 42 can be configured such that fluid flow through the flow regions is possible. For example, the flow regions 32, 42 of the expandable components 30, 40 can provide a flow path for blood or enable performance of a secondary procedure, such as the introduction of an embolic, anti-inflammatory, antibiotic, or thrombogenic agent and/or permit deployment of embolic coils within the expandable components 30, 40. Either of these components 30, 40 may allow blood to communicate to a side branch vessel through areas of the expandable component with large porosity while still providing stasis in the aneurysm.

According to some embodiments, the flow regions 32, 42 can comprise a passage, channel, or elongate void within the body 34, 44. Further, in embodiments wherein the flow regions 32, 42 comprise a material, the material of the flow regions 32, 42 can have a much higher porosity than that of the surrounding areas within the body 34, 44. Although FIGS. 10-11 illustrate only single or dual flow regions, some embodiments can be configured to comprise three, four, or more flow regions formed therein.

In some embodiments, the flow region can be separated from other portions of the body by a partial or full barrier. For example, the flow region can comprise a lumen formed through the body and the lumen can comprise an inner wall (not shown) extending therealong. The inner wall can comprise a continuous surface. However, the inner wall can also comprise one or more perforations extending through the wall, by which the lumen of the flow region is in fluid communication with the surrounding areas of the body. Thus, the flow region can provide isolated flow through the body or a flow that is in communication with other areas of the body of the expandable component.

Figure 12A:
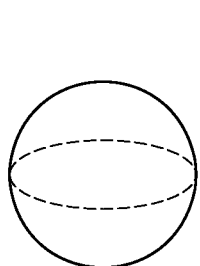
FIGS. 12A-12R are views illustrating alternate configurations for the foam structures of the intrasaccular device.
Figure 12B:
Figure 12C:
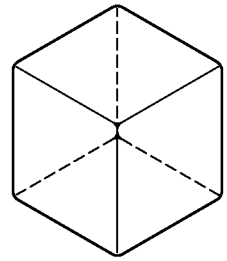
Figure 12D:
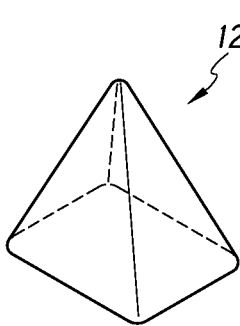
Figure 12E:
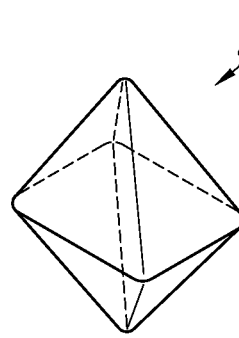
Figure 12F:
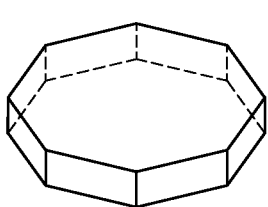
Figure 12G:
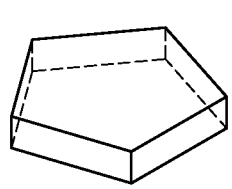
Figure 12H:
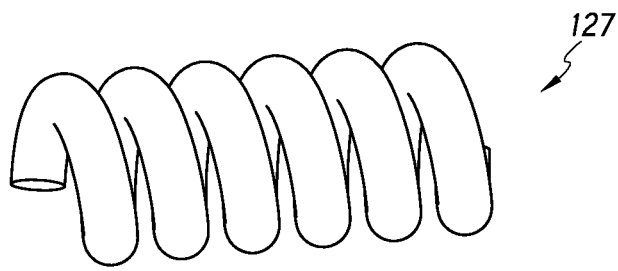
Figure 12I:
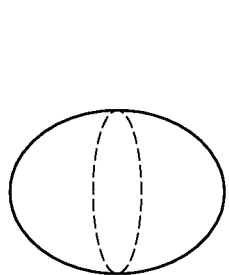
Figure 12J:
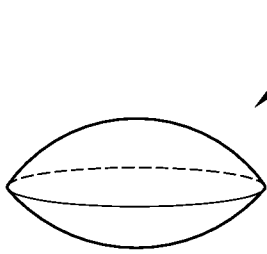
Figure 12K:
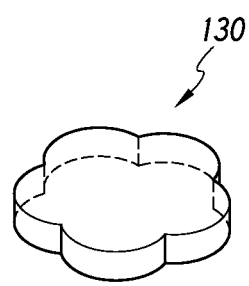
Figure 12L:
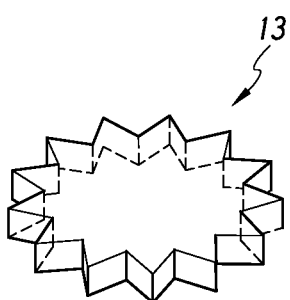
Figure 12M:
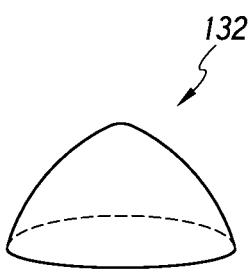
Figure 12N:
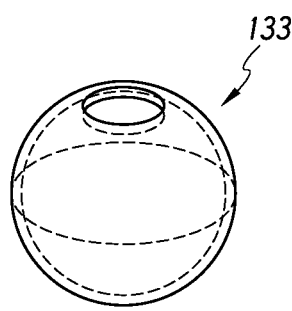
Figure 12O:
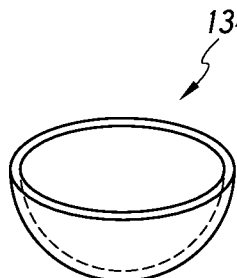
Figure 12P:
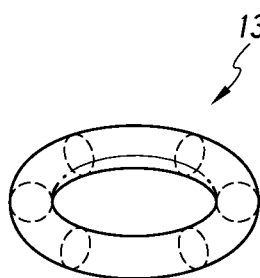
Figure 12Q:
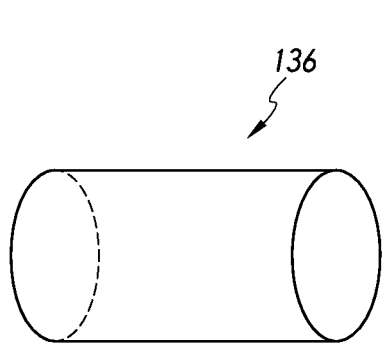
Figure 12R:
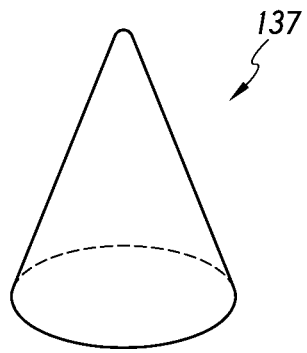

FIGS. 12A-12R illustrate various examples of shapes that can be used in accordance with some embodiments. Variations, whether by proportions, combinations, or other modifications of the disclosed shapes can be made, as taught herein. Without limitation, the shapes illustrated in FIGS. 12A-12R can comprise a sphere 120, a hemisphere 121, a cuboid 122, a pyramid 123, an octahedron 124, an octagonal prism 125, a pentagonal prism 126, a coil 127, a prolate spheroid 128, an oblate spheroid 129, a clover plate 130, a star plate 131, a paraboloid of revolution 132, a hollow sphere 133, a bowl 134, a torus 135, a cylinder 136, a cone 137, or combinations thereof.

In particular, in some embodiments, an intrasaccular device can be provided that comprises first and second expandable components of which at least one has a shape selected from the group consisting of cylinders, hemispheres, polyhedrons, prolate spheroids, oblate spheroids, plates, bowls, hollow structures, clover shapes, non-spherical surface of revolution, and combinations thereof. Additional expandable components can be provided that have substantially spherical shapes.

In accordance with some embodiments, an intrasaccular device can comprise first and second expandable components having different shapes. Further, the first and second expandable components can have different sizes. A third expandable component can be used, which can have the same or different sizes or shapes compared to either or both of the first and second expandable components. Thus, the first, second, and third expandable components can each have a different size and/or shape compared to each other. Such principles can apply to additional components, such as fourth, fifth, sixth components, and so forth.

Further, the shapes mentioned above can be solid or at least partially hollow (e.g., having a cavity or void therewithin). Hollow expandable components can comprise braided structures (e.g., braided spheres), foam structures, and the like. A hollow expandable component can be released into the aneurysm by itself or in combination with other occlusive material, such as a liquid embolic, additional expandable components, or coils.

Figure 13:
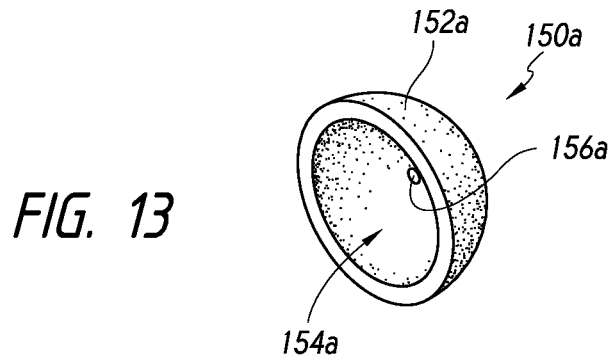
FIGS. 13-15 illustrate hollow structures of an intrasaccular device, according to some embodiments.
Figure 14:
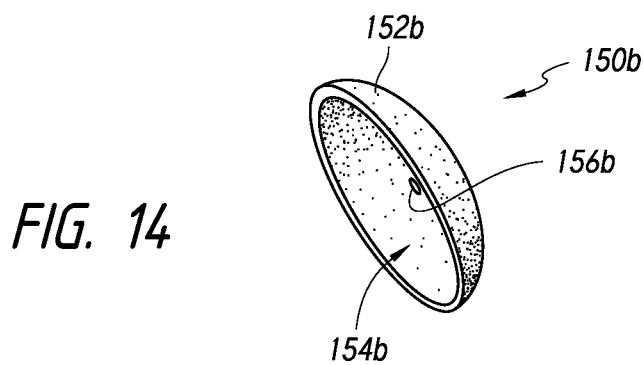
Figure 15:
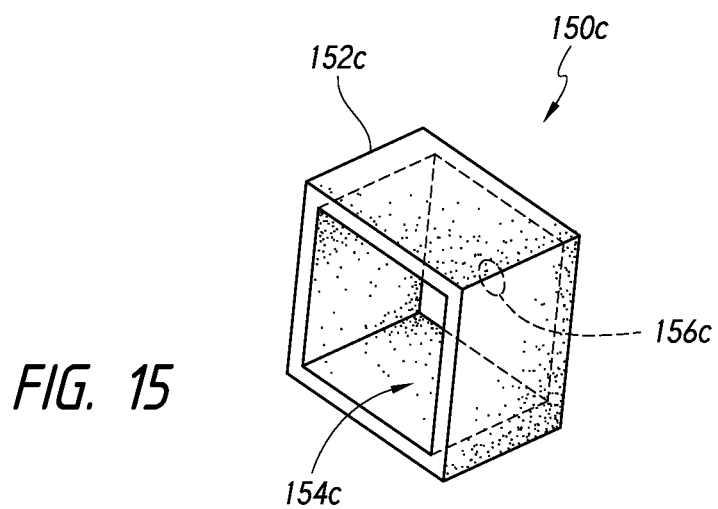

For example, FIGS. 13-15 illustrate hollow structures that can be used in accordance with embodiments of an intrasaccular device. FIGS. 13-15 each illustrates an intrasaccular device 150*a*, 150*b*, 150*c*. Each device 150*a*, 150*b*, 150*c* can comprise a shape having a hollow body 152*a*, 152*b*, 152*c*, which can in turn define a cavity 154*a*, 154*b*, 154*c*. The hollow body 152*a*, 152*b*, 152*c* can be advantageous at least because it can enable the intrasaccular devices 150*a*, 150*b*, 150*c* to have a more compact compressed state than a corresponding intrasaccular device (having an equivalent size when expanded) that is not hollow. Further, because the body 152*a*, 152*b*, 152*c* is hollow, the intrasaccular devices 150*a*, 150*b*, 150*c* can provide greater packing volumes within the aneurysm while using less material. Furthermore, because the intrasaccular device 150*a*, 150*b*, 150*c* can be compressed, comparatively, to a smaller size in its compressed state, the intrasaccular device 150*a*, 150*b*, 150*c* can be delivered through a smaller microcatheter.

Additionally, in some embodiments, the intrasaccular device 150*a*, 150*b*, 150*c* can be configured to comprise an aperture 156*a*, 156*b*, 156*c* in communication with the cavity 154*a*, 154*b*, 154*c* to permit introduction of, e.g., at least one additional expandable component, a liquid embolic, or embolic coils to further pack and/or support the aneurysm. In lieu of an aperture 156*a*, 156*b*, 156*c*, the clinician may perforate the intrasaccular device 150*a*, 150*b*, 150*c* before or during the procedure. In such a capacity or procedure, the intrasaccular device 150*a*, 150*b*, 150*c* can function as an intrasaccular framing device.

Figure 40:
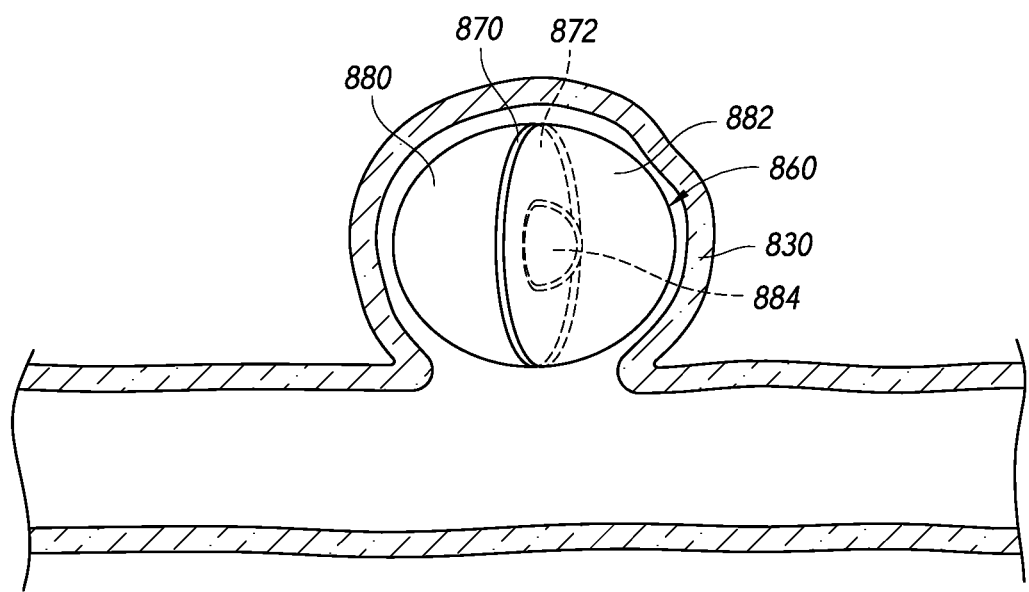
FIG. 40 illustrates an intrasaccular device comprising a plurality of interlocking expandable components positioned within a saccular aneurysm, according to some embodiments.
Figure 44:
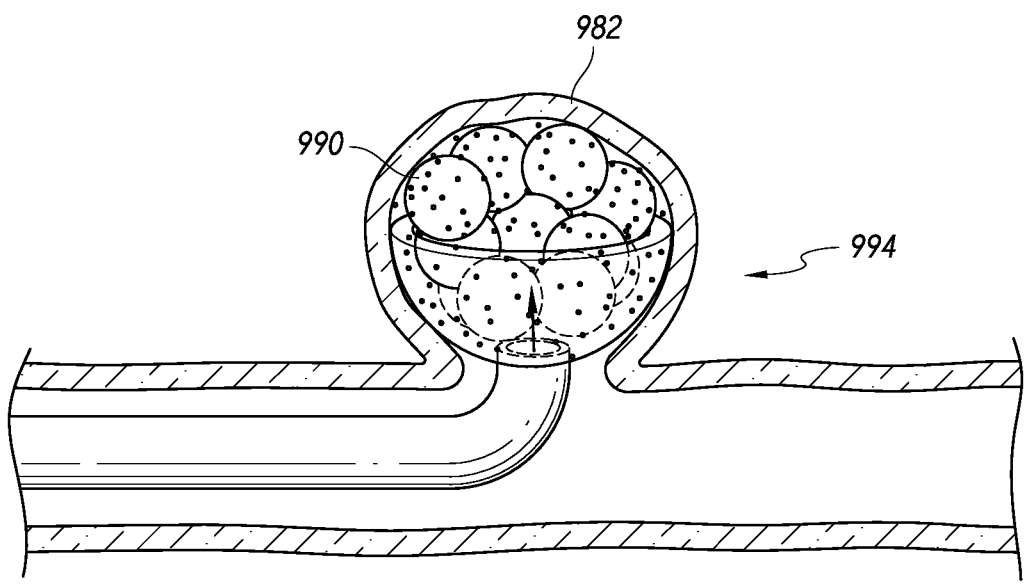
FIG. 44 illustrates a schematic view of a procedure in which an embolic liquid and an intrasaccular device comprising a plurality of expandable components are inserted into an aneurysm, according to some embodiments.

For example, the intrasaccular device 150*a*, 150*b*, 150*c* can be expanded within the aneurysm such that the intrasaccular device 150*a*, 150*b*, 150*c* extends across the neck of the aneurysm with the aperture 156*a*, 156*b*, 156*c* being accessible through the neck (see e.g., FIGS. 40 and 44). According to some embodiments, although the intrasaccular device extends across the neck, it may not touch or contact the neck of the aneurysm. Further, in embodiments that comprise an open end, the intrasaccular device 150*a*, 150*b*, 150*c* can be oriented such that the open end faces the fundus of the aneurysm and the closed end (including the aperture 156*a*, 156*b*, 156*c*) extends across the neck of the aneurysm.

Alternately, the aperture 156*a*, 156*b*, 156*c* may permit the introduction of a second smaller expandable component having a hollow interior. A third expandable component, smaller than the second expandable component, may then be introduced into the hollow interior of the second expandable component. Additional smaller foam structures may be added in a similar manner. FIGS. 13, 14, and 15 illustrate spheroid, ellipsoid and prism-shaped foam structures 402, respectively.

In alternate embodiments, the intrasaccular device 150*a*, 150*b*, 150*c* may receive any of the aforedescribed solid foam structures of the prior embodiments until the cavity 154*a*, 154*b*, 154*c* is packed to the desired capacity.

Figure 16:
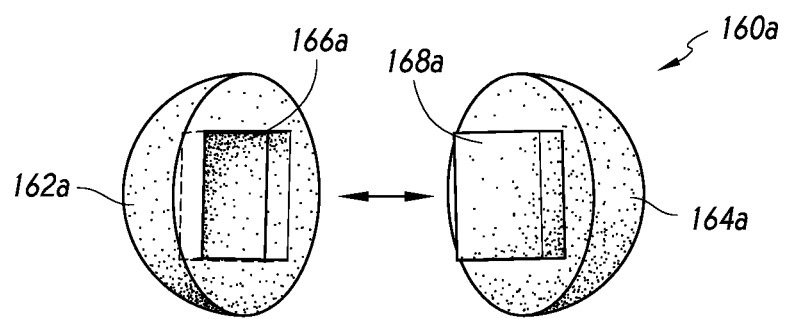
FIGS. 16-18 illustrate interlocking structures of an intrasaccular device, according to some embodiments.
Figure 17:
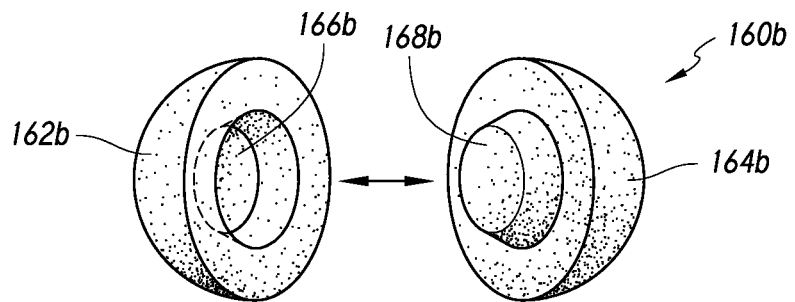
Figure 18:
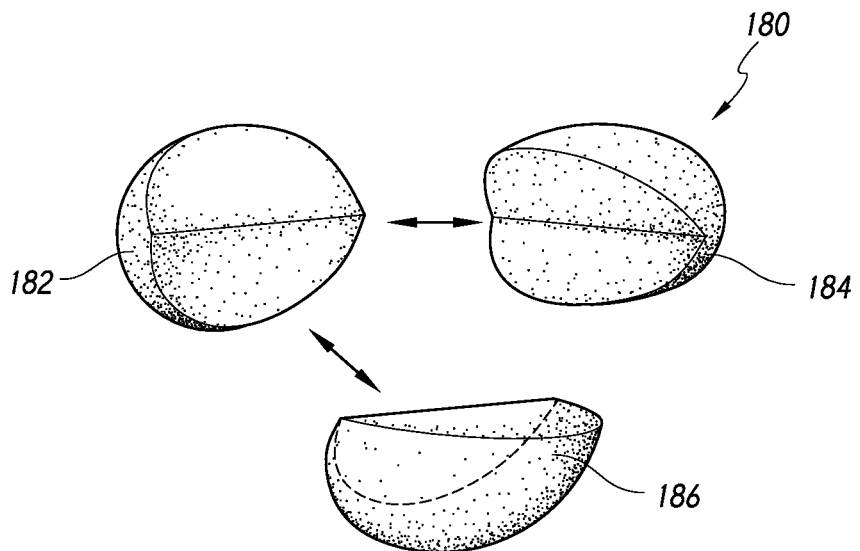

FIGS. 16-18 illustrate interlocking structures of an intrasaccular device, according to some embodiments. For example, FIGS. 16-17 illustrate a composite intrasaccular device 160*a*, 160*b* having first and second portions or components 162*a*, 162*b*, 164*a*, 164*b*. The first and second portions 162*a*, 162*b*, 164*a*, 164*b* can comprise respective engagement structures 166*a*, 166*b*, 168*a*, 168*b*.

The intrasaccular devices 160*a*, 160*b* shown in FIGS. 16-17 can be configured such that the respective engagement structures 166*a*, 166*b*, 168*a*, 168*b* provide a loose fit with each other when the first and second portions 162*a*, 162*b*, 164*a*, 164*b* are in their expanded states. However, according to some embodiments, the protrusions of the respective engagement structures 166*a*, 166*b*, 168*a*, 168*b* can be oversized relative to the recess of the respective engagement structures 166*a*, 166*b*, 168*a*, 168*b*, such that the protrusion expands to create an interference fit inside the recess, thereby securing the first portion 162*a*, 162*b* relative to the second portion 164*a*, 164*b* in the expanded states. In such embodiments, the protrusion and recess can be guided towards each other as the first and second portions 162*a*, 162*b*, 164*a*, 164*b* expand within the aneurysm. In addition to the engagement structures shown, other engagement structures can be provided, such as a ball and socket, slots, pins, etc.

Further, in embodiments having only two interconnecting portions, such interconnecting portions can be configured to restrict at least two degrees of freedom of motion of the opposing portion. Motion can be restricted in two or more of the following directions: up-and-down translation, forward and backward translation, left and right translation, side to side pivoting or rolling, left and right rotating or yawing, and forward and backwards tilting or pitching. Further, in some embodiments, such as those illustrated in FIGS. 16-17, at least three degrees of the freedom of motion of a portion can be restricted. For example, the interconnection between portions of such embodiments can restrict four, five, or all six degrees of freedom of motion of a given portion.

FIG. 18 illustrates an intrasaccular device 180 having a plurality of interconnecting portions 182, 184, 186. These interconnecting portions 182, 184, 186 can be configured to abut each other in a complementary configuration, such as to provide a composite structure. In some embodiments, the interconnecting portions 182, 184, 186 can be configured to restrict at least two, three, four, five, or six degrees of freedom of motion of another component.

The mating expandable components, such as those embodiments illustrated in FIGS. 16-18 can be delivered into the aneurysm and arranged in situ such that the engagement structures are aligned and interconnected appropriately such that the expandable components are mated. In some embodiments, the mating of the expandable components can interlock the components as a composite structure or unit, as in FIG. 16.

As noted above, in accordance with some embodiments, at least a portion of the intrasaccular device can comprise a coating or material for enhancing therapeutic, expansive, or imaging properties or characteristics of at least one or every expandable component of the intrasaccular device.

The intrasaccular device can be configured such that an expandable component thereof is coated with a biocompatible material to promote endothelialization or provide a therapeutic effect.

Figure 19:
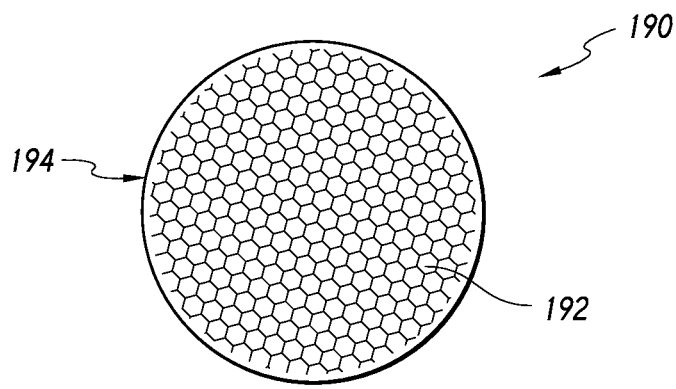
FIGS. 19-21 illustrate alternate embodiments of the intrasaccular device incorporating coated foam structures.

For example, FIG. 19 illustrates an alternate embodiment of the present disclosure. In accordance with this embodiment, the intrasaccular device 190 comprising an expandable component 192 that can be coated and/or embedded with at least one coating 194, such as a bioactive material or agent.

The coating 194 may include thrombogenic coatings such as fibrin, fibrinogen or the like, anti-thrombogenic coatings such as heparin (and derivatives thereof), urukinase or t-PA, and endothelial promoting coatings or facilitators such as, e.g., VEGF and RGD peptide, and/or combinations thereof. Drug eluting coatings and a drug eluting foam composite, such as anti-inflammatory or antibiotic, coatings are also envisioned. These drug eluting components may include nutrients, antibiotics, anti-inflammatory agents, antiplatelet agents, anesthetic agents such as lidocaine, and anti-proliferative agents, e.g. taxol derivatives such as paclitaxel. Hydrophilic, hygroscopic, and hydrophobic materials/agents are also envisioned.

As also noted above, in some embodiments, the expandable component can also comprise an expansion-limiting coating that slows expansion of the component from its natural rate of expansion to a slower rate of expansion such that in the process of expanding, the position of the component can be adjusted within the aneurysm or the component can be removed from the aneurysm, if necessary. Examples of polymers that can be used as expansion-limiting coatings can include hydrophobic polymers, organic non-polar polymers, PTFE, polyethylene, polyphenylene sulfide, oils, and other similar materials.

Figure 20:
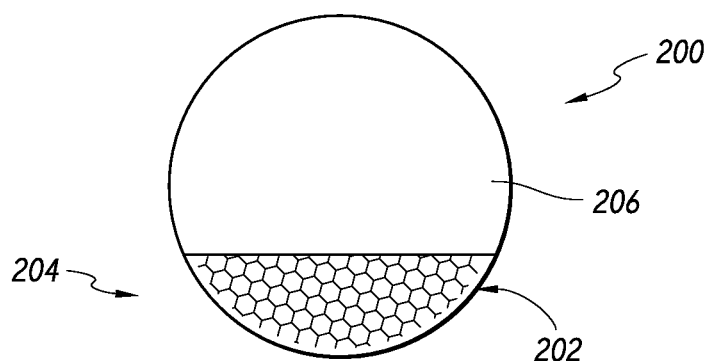

In embodiments, only specific segments of the intrasaccular device may be embedded or coated with an agent to provide desired characteristics to the expandable component(s). For example, as depicted in FIG. 20, an intrasaccular device 200 can comprise a non-thrombogenic coating 202 may be applied to a lower half 204 of the expandable component 206 to minimize clotting at this location. Such coatings may be desirable in aneurysms located at a bifurcation such that blood flow to branch arteries is permitted through the segment of the foam structure having the non-thrombogenic coating. The coated area 202 may be a different color than the remaining portion of the expandable component 206 to assist the surgeon in identifying this area.

Optionally, the coated area 202 can also comprise radiopaque material to assist the surgeon in visualization and placement of the expandable component 206 in a desired orientation relative to the aneurysm. The expandable component 206 can have radiopacity characteristics either by adding radiopaque filler to the material (which in some embodiments comprises a foam material), such as bismuth, or attaching radiopaque markers. Alternatively, a radiopaque material can be attached to the expandable component 206, such as by dipping, spraying, or otherwise mechanically, chemically, or thermally attached, injected into, or blended into to the expandable component 206.

Figure 21:
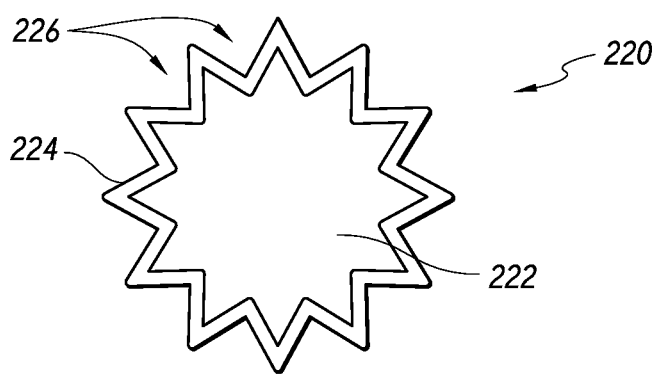

FIG. 21 illustrates another embodiment of the intrasaccular devices illustrated in FIGS. 19-20. In FIG. 21, an intrasaccular device 220 is shown that comprises has a star-shaped expandable component 222 which may be partially or fully coated and/or embedded with a material 224, such as any of the aforedescribed agents. The star shape can provide increased surface area due to the presence of the undulations 226 in the outer surface of the expandable component 222.

Once the expandable component is delivered into the aneurysm, it can expand back to its full size or expanded state, confined within the neck of the aneurysm with minimal herniation within the parent vessel. The foam could be self-expandable, chemically expandable, thermally expandable, or expandable in response to pH changes or to light. Shape memory foams such as polyurethane foam can be used.

Various delivery systems and procedures can be implemented for delivering an intrasaccular device comprising one or more expandable components, as discussed herein. Further, a system and method are provided for delivery of an intrasaccular device to an aneurysm and/or recapturing the device for removal or repositioning.

For example, in accordance with some embodiments, FIGS. 22-25 illustrate a delivery system and a procedure for implanting an intrasaccular device. In the illustrated embodiment, a delivery catheter 300 is advanced within a vessel 302 until a distal end 304 of the delivery catheter 300 is positioned adjacent to a target site, such as an aneurysm 306.

A carrier assembly 320 can be configured to engage an intrasaccular device 330 and deliver the intrasaccular device 330 into the aneurysm 306. The carrier assembly 320 can comprise a core member 322 and an engagement member 324. The core member 322 can be interconnected with the engagement member 324. The engagement member 324 can comprise at least two arm members 340 having a closed position (see FIG. 22) and an open position (see FIG. 23). In the closed position, the arm members 340 can be engaged with at least a portion of the intrasaccular device 330 to facilitate distal advancement and retention of the intrasaccular device 330 within the lumen of the catheter 300.

Figure 23:
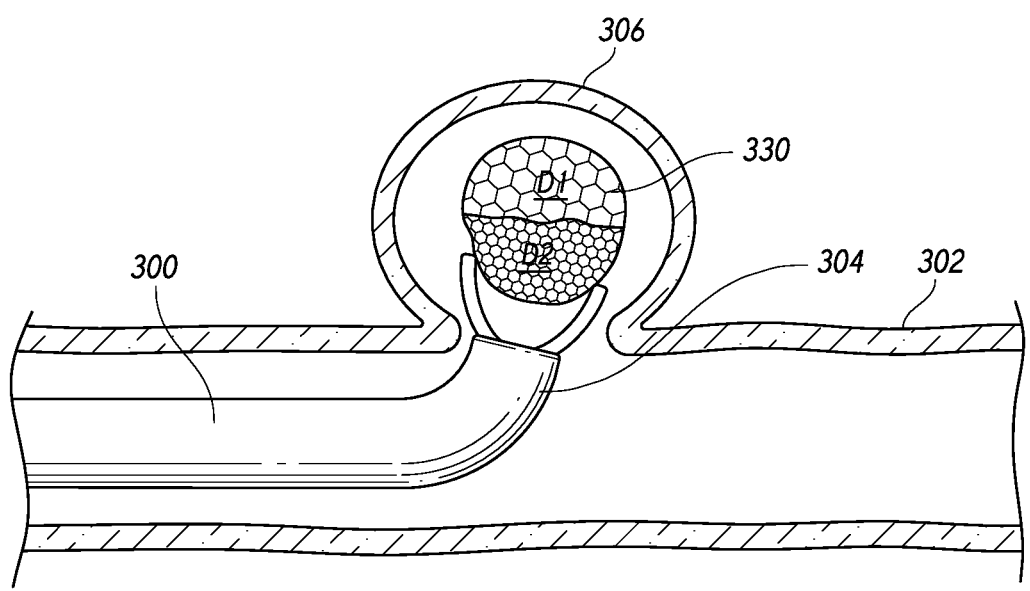

The carrier assembly 320, disposed within a lumen of the delivery catheter 300, can be advanced distally through the catheter 300 until reaching the distal end 304 of the catheter 300. Upon reaching the distal end 304, the carrier assembly 320 can be actuated to release an intrasaccular device 330 into the aneurysm 306, as shown in FIG. 23.

The arm members 340 can be spring-loaded or configured to spring open from the closed position upon being advanced out of or distally beyond the distal end 304 of the catheter 300. However, the arm members 340 can also be manually actuated using a proximal control mechanism, thereby allowing the arm members 340 to continue engaging the intrasaccular device 330 even after the arm members 340 have moved out of the lumen of the catheter 300. For example, such a proximal control mechanism can comprise a proximally extending wire coupled to a first of the arm members 340, the proximal retraction of which causes the first arm member 342 retract into the catheter 300, thus releasing the intrasaccular device 330. Various other control mechanisms, such as those disclosed herein, can also be implemented in accordance with some embodiments.

After the intrasaccular device 330 has been released into the aneurysm 306, the intrasaccular device 330 can begin to expand. The clinician can carefully monitor the orientation of the intrasaccular device 330 relative to the neck or surrounding the vasculature of the aneurysm 306.

Figure 24:
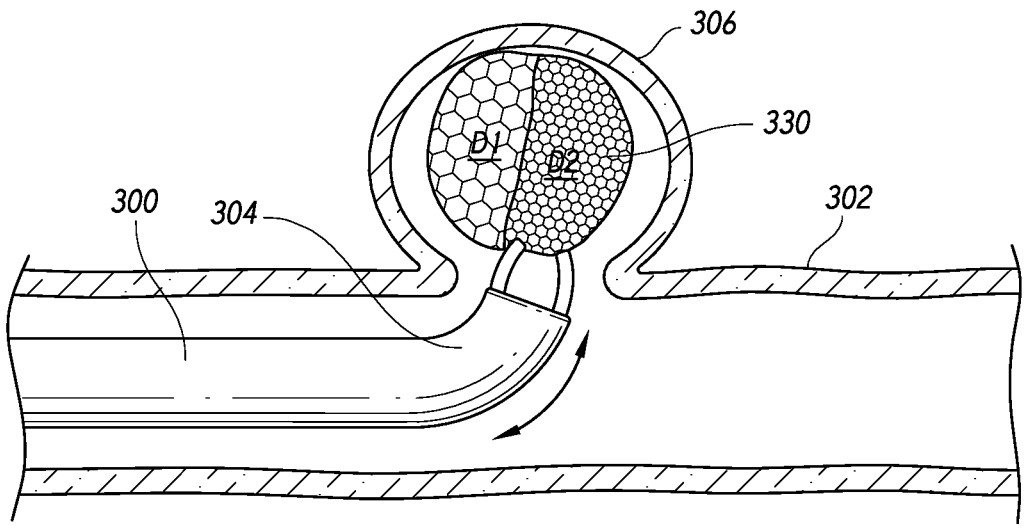
Figure 25:
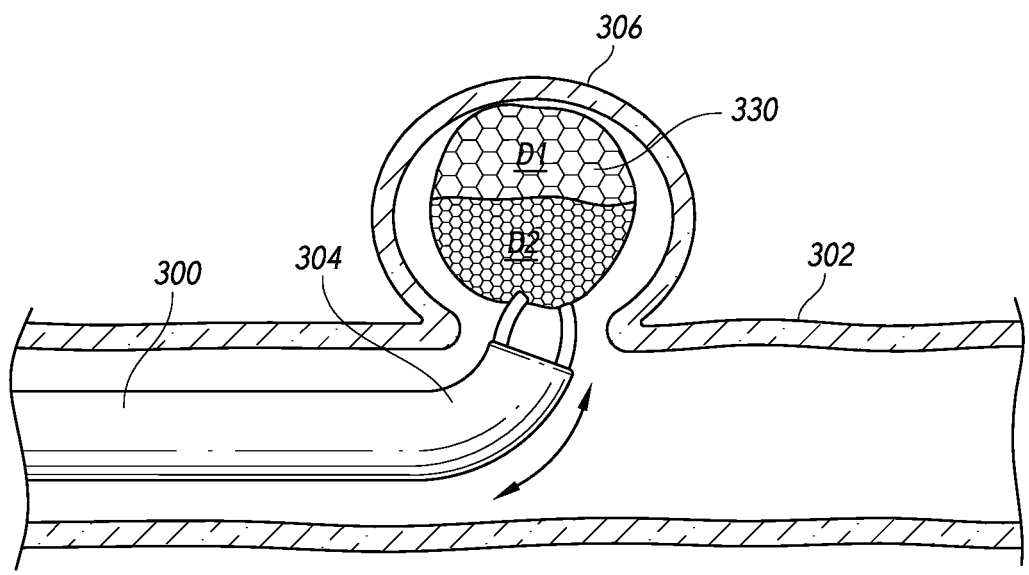

According to some embodiments, if the intrasaccular device 330 has a specific characteristic, such as a porosity profile, coating, shape, etc., intended for placement in a certain location of the aneurysm 306, the clinician can position the intrasaccular device 330 by manually rotating, moving, maintaining the position of, or otherwise adjusting the position of the intrasaccular device 330 within the aneurysm 306 as the intrasaccular device 330 expands. This procedure is illustrated in FIGS. 24-25. Thus, by gently manipulating at least one of the arm members 340, the clinician can contact the intrasaccular device 330 to ensure proper orientation of the intrasaccular device 330 within the aneurysm 306. Although the manipulation of the position of the expandable device is shown in the context of the carrier assembly 320 in FIGS. 22-25, the position of the expandable device can be manipulated using various other deployment or delivery devices, such as those shown in FIGS. 31A-37 or FIGS. 61-63.

In the performance of such procedures, the intrasaccular device 330 can beneficially be coated with an expansion-limiting coating, such as those discussed above. In such embodiments, the expansion-limiting coating can allow the intrasaccular device 332 slowly expand, thus providing the clinician with a greater, and in some cases, a specified or expected period of time after releasing the intrasaccular device 330 to adjust the position of the intrasaccular device 330 within the aneurysm 306.

Figure 26:
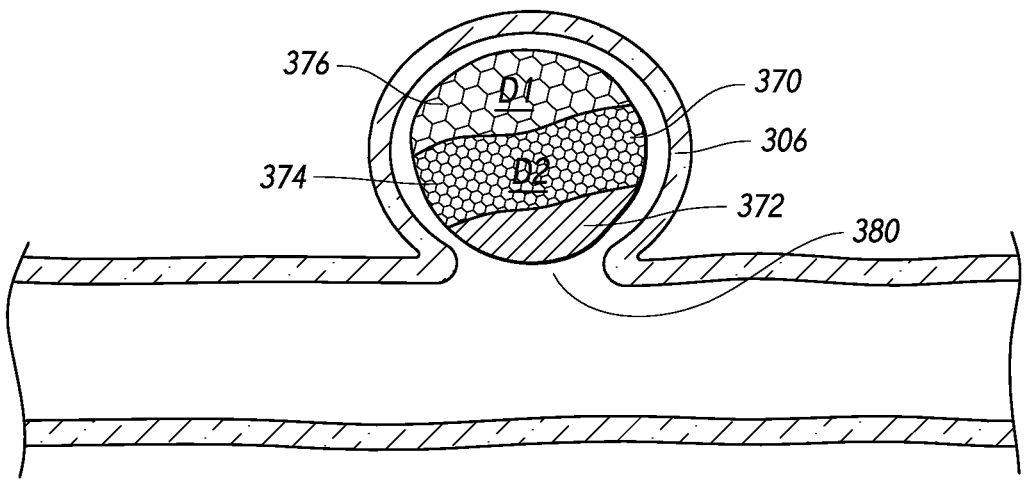
FIG. 26 illustrates an intrasaccular device having a radiopaque material and positioned within an aneurysm, according to some embodiments.

FIG. 26 illustrates the placement of an intrasaccular device 370 within an aneurysm 306. The intrasaccular device 370 can comprise a radiopaque material 372. The radiopaque material 372 can be located at a specific end of the intrasaccular device 370 (in this case, on a first portion 374 of the intrasaccular device 370, which has a lower porosity than a second portion 376 thereof). In the illustration of FIG. 26, the intrasaccular device 370 is in an intermediate expanded state (i.e., it has not yet fully expanded), and as the device 370 expands, the clinician can adjust its position based on a visualization of the radiopaque material 372. The clinician can visualize the orientation of different sections or portions of an intrasaccular device relative to the neck or surrounding vasculature of an aneurysm, and here, align the radiopaque material 372 with the neck 380 of the aneurysm 306 (or in some embodiments, a fundus of the aneurysm 306) in order to maintain the lower porosity first portion 374 of the intrasaccular device 370 adjacent to or extending across the aneurysm neck 380.

FIGS. 27-30 illustrate different aneurysm configurations and surrounding vasculature that may be treated best by achieving a specific orientation of an intrasaccular device within the aneurysm.

Figure 27:
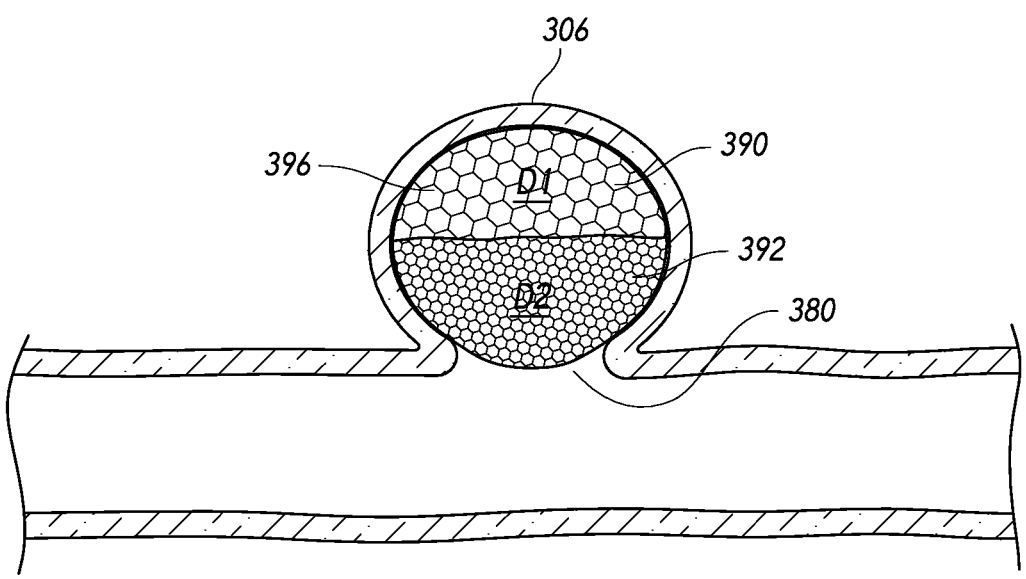
FIGS. 27-30 illustrate intrasaccular devices positioned within an aneurysm based on a porosity profile, according to some embodiments.

For example, FIG. 27 illustrates an intrasaccular device 390 oriented such that a low porosity section 392 thereof is positioned or extends across the neck 380 of the aneurysm 306, with a higher porosity section 396 positioned in the fundus of the aneurysm 306. FIG. 27 also provides an illustration of the final result of the process described above with respect to FIGS. 22-25. Thus, after continued expansion, the intrasaccular device 330 shown in FIGS. 22-25 can achieve the position or state of expansion illustrated in FIG. 27.

Figure 28:
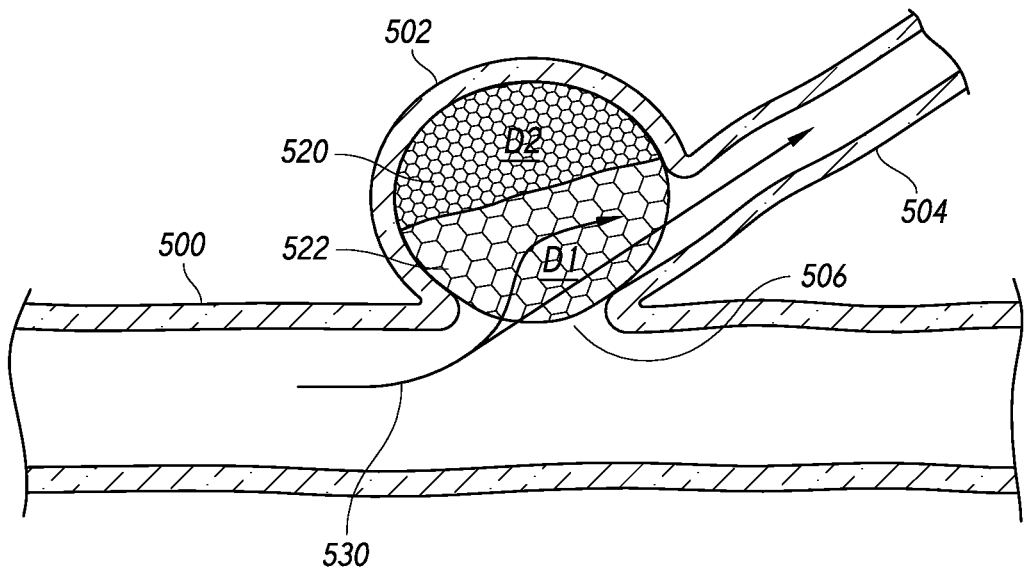

FIG. 28 illustrates an artery 500 having an aneurysm 502 and a perforating vessel 504 extending through the aneurysm 502 adjacent to a neck 506 of the aneurysm 502. In such circumstances, an intrasaccular device 520 can be positioned within the aneurysm 502 such that a high porosity section 522 extends across the neck 506 of the aneurysm 502 in order to permit blood flow into the perforating vessel 504, as illustrated with arrows 530.

Figure 29:
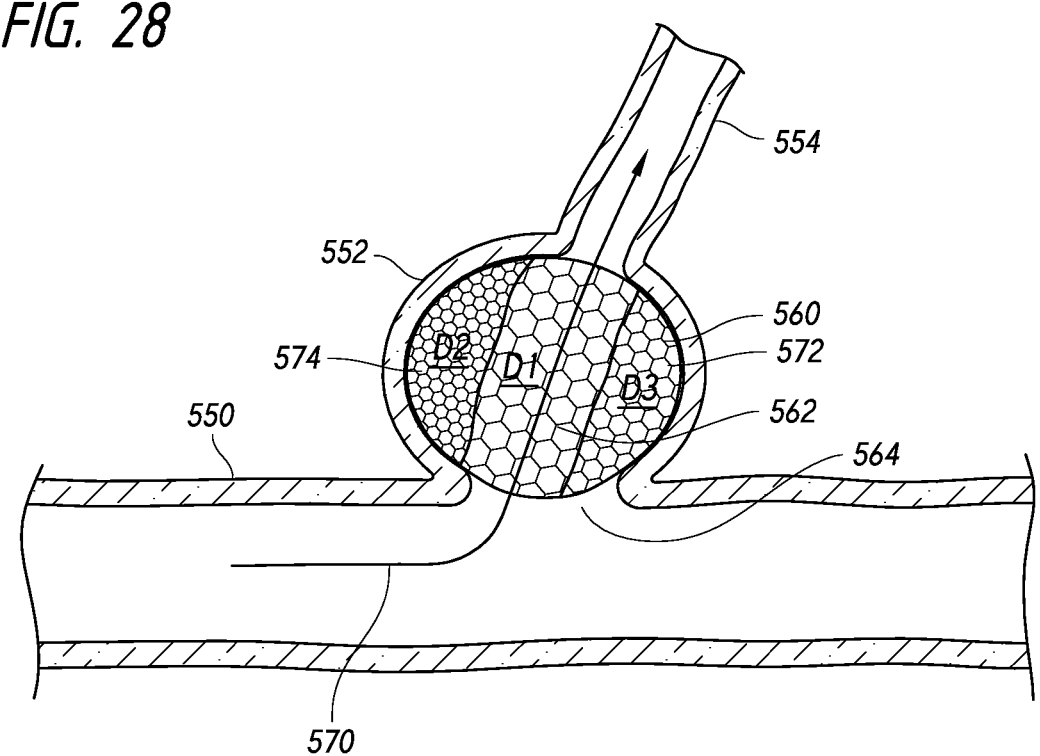

FIG. 29 illustrates an artery 550 having an aneurysm 552 and a perforating vessel 554 extending from the fundus of the aneurysm 552. In such situations, an intrasaccular device 560 can be positioned within the aneurysm 552 such that a first, high porosity section or channel 562 of the intrasaccular device 560 provides a fluid pathway for blood to flow through the neck 564 of the aneurysm 552 toward and into the perforator vessel 554, as shown by arrow 570. Additionally, the intrasaccular device 560 can be configured to comprise one or more low porosity sections 572, 574 that can tend to induce thrombosis and protect the aneurysm wall.

Figure 30:
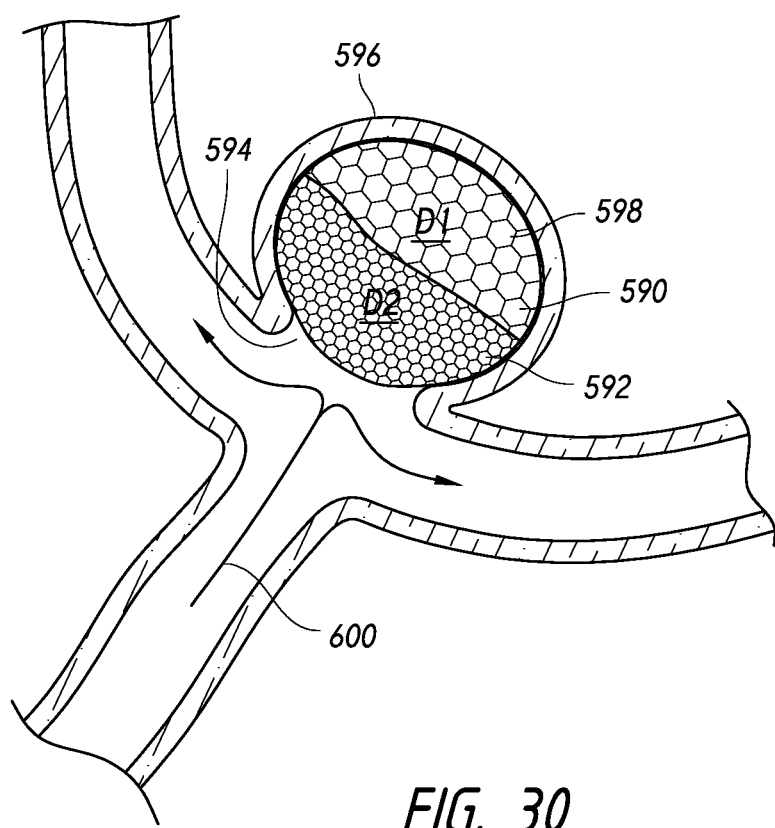

FIG. 30 illustrates an intrasaccular device 590 oriented such that a low porosity section 592 thereof is positioned or extends across the neck 594 of an aneurysm 596 located at a vessel bifurcation. As illustrated, a higher porosity section 598 can be positioned in the fundus of the aneurysm 596. Thus, flow through the bifurcation, as shown by arrows 600 can be diverted using the low porosity section 592, thereby relieving pressure on the aneurysm 596.

Figure 22:
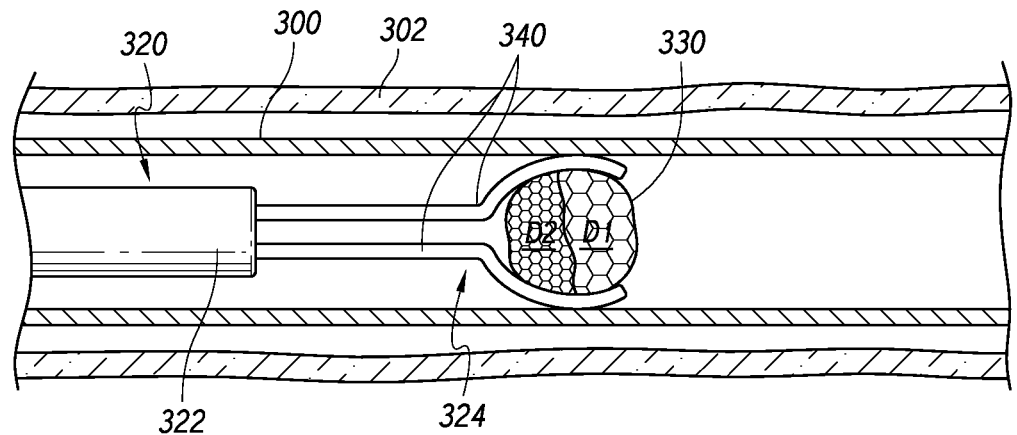
FIG. 22-25 illustrate a delivery system and a procedure for delivering an intrasaccular device, according to some embodiments.

Referring now to FIGS. 31A-34, engagement mechanisms for a delivery and recapture system, as shown in FIG. 22, are provided. These engagement mechanisms can provide secure engagement and release of one or more expandable components. Further, the system can recapture the device for removal or repositioning.

As discussed above with respect to the engagement mechanism of FIG. 22, the engagement mechanisms illustrated in FIGS. 31A-34 can move between closed and open positions in order to facilitate engagement with and delivery of an intrasaccular device into an aneurysm.

Figure 31A:
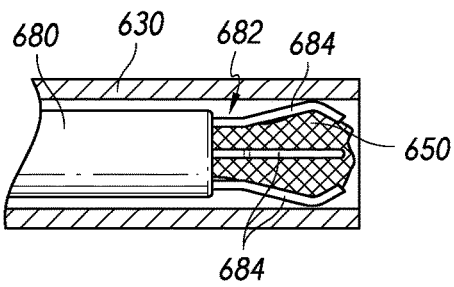
FIGS. 31A-34 illustrate alternative engagement mechanisms for the delivery system shown in FIG. 22, for engaging one or more expandable components, according to some embodiments.
Figure 31B:
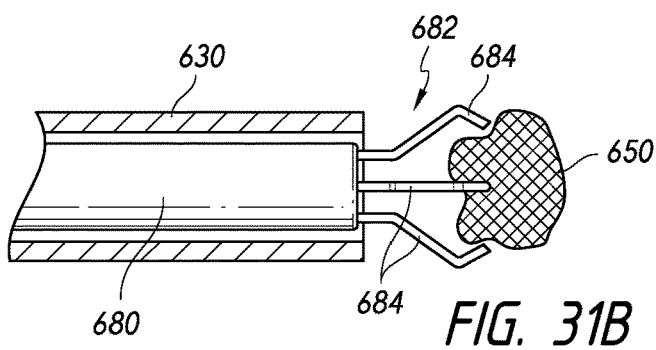

FIGS. 31A-31B illustrate a system and method for delivery an intrasaccular device to an aneurysm and/or recapturing the device for removal or repositioning. In one embodiment, the delivery system may include an introducer catheter or sheath 630. A delivery/retrieval member 680 can be disposed within a lumen of the catheter 630. The delivery/retrieval member 680 may include an elongated element 682 having a plurality of gripping elements 684 at one end. The delivery/retrieval member 680 can be dimensioned to traverse the longitudinal lumen of the introducer sheath 630. The gripping elements 684 can be adapted to open and close about the intrasaccular device 650. In some embodiments, the gripping elements 684 can be normally biased to an open position.

In some embodiments, the delivery/retrieval member 680 can comprise the Alligator Retrieval Device, manufactured by Covidien LP, generally represented in FIGS. 31A-31B. The Alligator Retrieval Device can include a flexible wire having a plurality of gripping arms or elements, e.g., four arms, at the distal end of the flexible wire. Other embodiments for the gripping elements 58 include a clover leaf design, fish hook design, or dissolvable coupling, as shown in FIGS. 31A-34, respectively.

In use, an access catheter is advanced within the neurovasculature as is conventional in the art. A suitable microcatheter adaptable for navigation through the tortuous neurovascular space to access the treatment site is disclosed in commonly assigned U.S. Pat. No. 7,507,229, the entire contents of which are hereby incorporated herein.

The gripping elements 684 of the delivery/retrieval member 680 are positioned about the intrasaccular device 650 (FIG. 31A), and the delivery/retrieval member 680 is withdrawn into the introducer sheath 630 such that the gripping elements 684 move inwardly during engagement with the inner wall surface of the introducer sheath 630 to compress the foam structure of the intrasaccular device 650 as depicted in FIG. 31B. The intrasaccular device 650 is withdrawn into the introducer sheath 630. The introducer sheath 630 with the delivery/retrieval member 682 and intrasaccular device 650 positioned therein is advanced through the access catheter accessing the aneurysm. The access catheter may be removed if desired, or may be left in place. Thereafter, the introducer sheath 630 is oriented at the desired orientation with respect to the aneurysm. Any of the engagement devices illustrated herein can be used for both delivery and retrieval of expandable components.

The delivery/retrieval member 682 is advanced through the introducer sheath 630 whereby upon clearing the distal end of the introducer sheath 630 the gripping elements 684 of the delivery/retrieval member 682 open to release the intrasaccular device 650. In the event the intrasaccular device 650 is not properly positioned within the aneurysm or is dislodged, the gripping elements 684, in the open configuration, and extended beyond the introducer sheath 630, are positioned to circumscribe the intrasaccular device 650 within the vasculature. The delivery/retrieval member 682 is withdrawn into the introducer sheath 630 whereby the gripping elements 684 compress the foam material of the intrasaccular device 650 to permit reception of the device 650 within the lumen of the introducer sheath 630. Thereafter, the intrasaccular device 650 can be removed from the neurovasculature or repositioned within the aneurysm by deployment of the delivery/retrieval member 682 in the manner discussed herein.

Figure 32A:
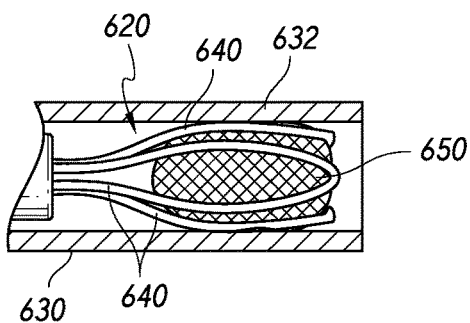
Figure 32B:
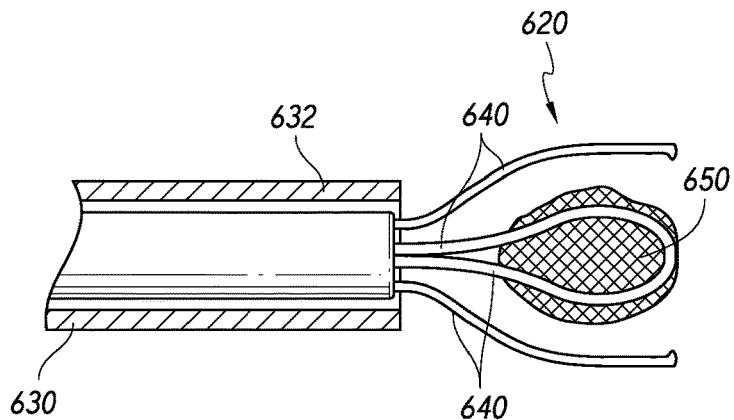

FIGS. 32A-32B similarly illustrate an engagement mechanism 620 in the form of a "clover" pattern. The engagement mechanism 620 can be disposed within a catheter 630 and advanced distally until exiting the lumen of the catheter 630 at the distal end 632. Upon exiting, wire loops 640 of the engagement mechanism 620 can be released from engaging the intrasaccular device 650. As illustrated in FIG. 31B, when released, the intrasaccular device 650 may not tend to snag or stick to the wire loops 640. Accordingly, the engagement mechanism 620 can provide fast and reliable disengagement with the intrasaccular device 650.

Figure 33A:
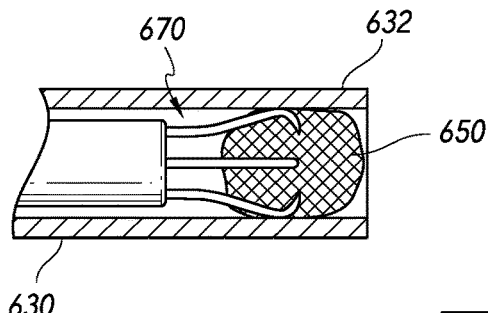
Figure 33B:
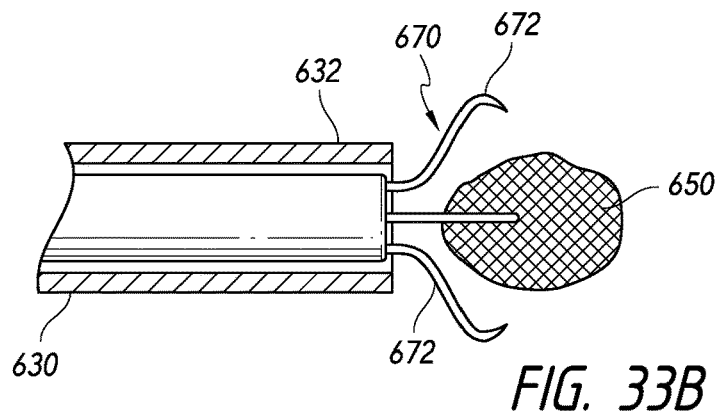

FIGS. 33A-33B illustrate another embodiment of an engagement mechanism 670 having a "fish hook" design, similar to the engagement mechanisms 324, 620 can move between closed and open positions upon exiting a distal end 632 of the catheter 630 the engagement mechanism 670 can comprise a plurality of hooks 672 configured to pierce or otherwise at least partially penetrate the intrasaccular device 650. Upon release, the hooks 672 can disengage from the intrasaccular device 650 in order to release the intrasaccular device 650 into the aneurysm.

Figure 34:
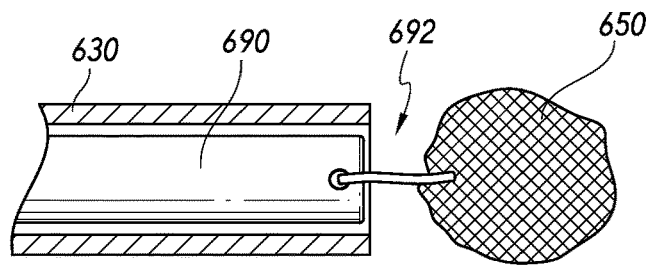

FIG. 34 illustrates an embodiment of a system in which a delivery member 690 is attached to an intrasaccular device 650 using a dissolvable coupling 692. The dissolvable coupling 692 can extend between the intrasaccular device 650 and an aperture or engagement member of the delivery member 690. In accordance with some embodiments, engagement member of the delivery member 690 can engage the dissolvable coupling 692 using a hook, wire loop, or other elongate member, such as those disclosed in other delivery systems above. The dissolvable coupling 692 can be actuated by chemical corrosion (e.g., electrolytic detachment), thermal corrosion, pH changes, light changes, etc. Further, the releasable connection 692 may be effected through an electrical, hydraulic or pneumatic connection where release of the intrasaccular device 650 is achieved through activation of any of these systems. For example, once the intrasaccular device 650 is positioned within the aneurysm, any of the aforementioned means may be actuated to release the intrasaccular device 650 from the delivery member 690.

Figure 35:
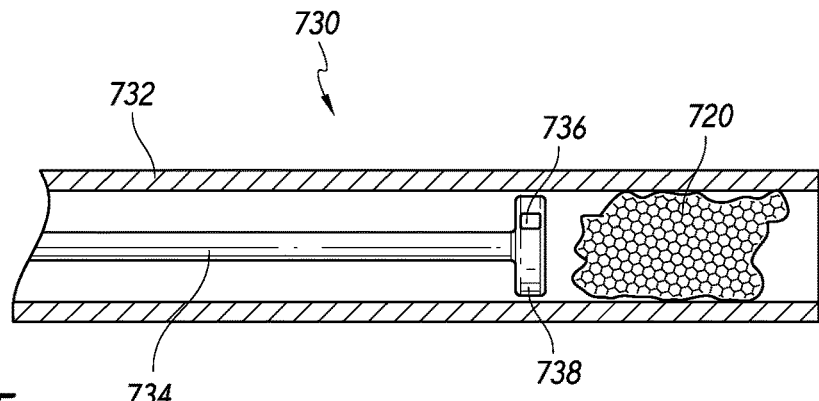
FIG. 35 illustrates a delivery system for delivering an intrasaccular device, according to some embodiments.

FIG. 35 illustrates a microcatheter delivery system for implanting an intrasaccular device 720 within the aneurysm. A delivery system 730 can comprise a delivery catheter 732 and pusher element 734 disposed within the delivery catheter 732. The intrasaccular device 720 in its normal configuration and predetermined geometry can be compressed and positioned within the lumen of the delivery catheter 732.

The delivery catheter 732 may be introduced within the neurovasculature and advanced to the treatment site. Once appropriately oriented with respect to the aneurysm, the pusher element 734 is actuated by, e.g., advancing a handle or actuator operatively connected to the proximal end of the pusher element 734 to cause the distal or remote end of the pusher element 734 to eject the intrasaccular device 720. The intrasaccular device 720 can expand to pack the aneurysm.

Additionally, in accordance with some embodiments, the pusher element 734 can comprise a radiopaque material or component 736 disposed on a contact member 738 of the pusher element 734. As the pusher element 734 is advanced within the lumen of the catheter 732, the radiopaque material 736 can enable the clinician to visualize the location of the intrasaccular device 720 to ensure proper positioning of the pusher element 734 within the lumen of the catheter 732.

Figure 36:
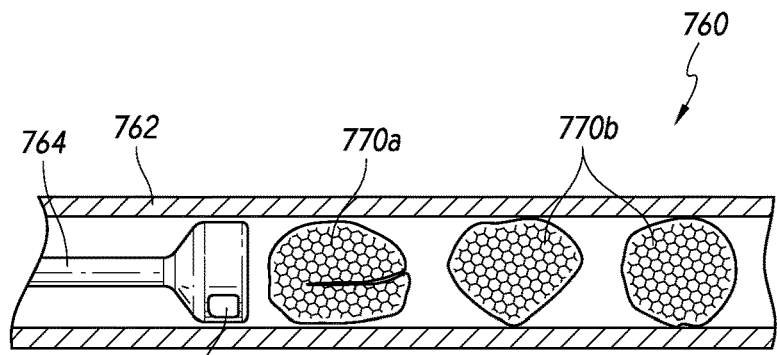
FIG. 36 illustrates a delivery system for delivering an intrasaccular device comprising a plurality of expandable components, according to some embodiments.

FIG. 36 illustrates an alternate embodiment of the delivery system. In accordance with this embodiment, system 760 includes introducer sheath 762 and delivery member 764 disposed within the introducer sheath 762. The delivery member 764 may be a push rod advanceable within the introducer sheath 762. The intrasaccular device of this disclosure includes a plurality of intrasaccular pellets 770a, 770b disposed within the introducer sheath 762 to be ejected in sequence via the delivery member 764. For example, the plurality of pellets can comprise a framing shape, which has been compressed and folded as a framing pellet 770a. The pellet 770a will be the last pellet to enter the aneurysm (after pellets 770b). Thus, the framing pellet 770a can tend to expand so as to extend across a neck of the aneurysm (although not necessarily touching the ostium of the aneurysm.

These intrasaccular devices or pellets 770a, 770b may be smaller in dimension than the aforedescribed intrasaccular devices to enable multiple and strategic deployment within the aneurysm. Any of the embodiments of the aforedescribed intrasaccular devices may be incorporated within the pellets 770a, 770B. Further, the delivery member 764 can incorporate one or more radiopaque materials are components 772 to facilitate visualization of the location of the delivery member 764 within the sheath 762.

Figure 37:
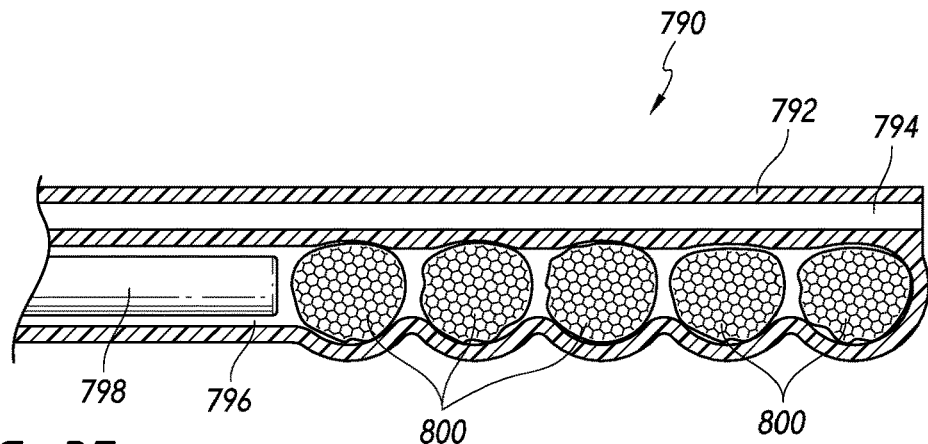
FIG. 37 illustrates a delivery system, advanceable along a guide wire, for delivering an intrasaccular device comprising a plurality of expandable components, according to some embodiments.

FIG. 37 illustrates another delivery system 790, in accordance with some embodiments. The delivery system 790 can comprise an over-the-wire system having a guide member 792 comprising a guide wire lumen 794. The guide member 792 can also comprise a delivery lumen 796 in which a push rod 798 can be disposed for axial movement therewithin an order to deliver an intrasaccular device comprising a plurality of expandable components 800. Such an embodiment can allow the system 790 to define a minimal cross-sectional profile, thereby allowing the system 790 to extend into and through very narrow vessels to treat aneurysms in smaller vessels.

Figure 38:
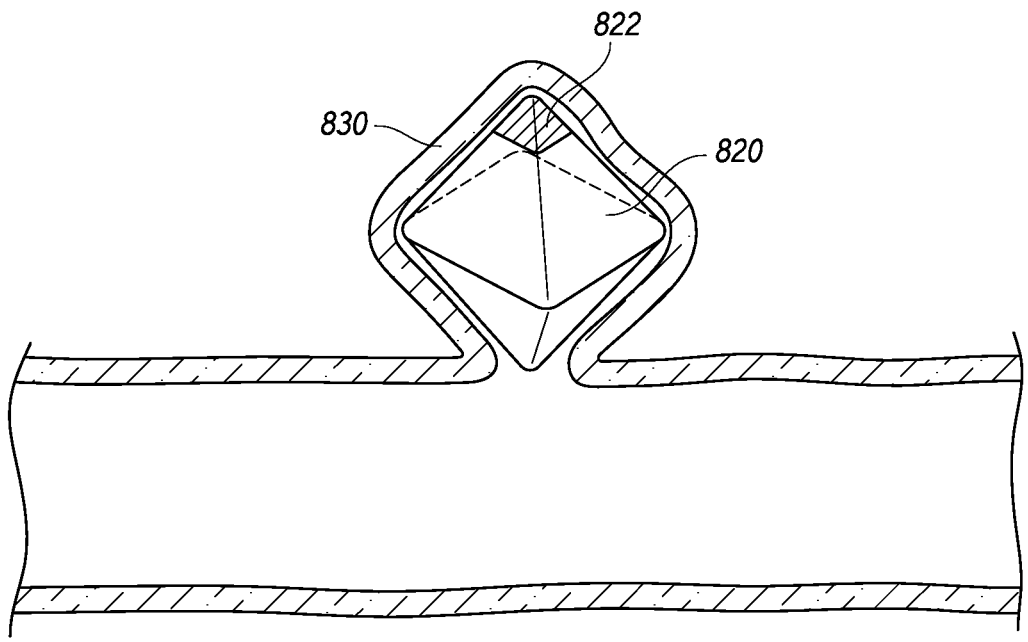
FIG. 38 illustrates an intrasaccular device having a specific shape and a radiopaque material positioned within a saccular aneurysm, according to some embodiments.

FIGS. 38-42 illustrate various implementations of some of the embodiments disclosed herein. For example, FIG. 38 illustrates an intrasaccular component 820 that has been implanted into an aneurysm 830. As shown, the intrasaccular component 820 comprises a shape that is substantially an octahedron. Such a shape can be beneficial for securely anchoring the intrasaccular component 820 within the aneurysm 830 given the expanding waist and tapering ends that permit the intrasaccular component 820 to fit well within a berry or saccular aneurysm. In addition, the intrasaccular component 820 also comprises a radiopaque material or marker 822 for use in locating and positioning the intrasaccular component 820 within the aneurysm 830.

Figure 39:
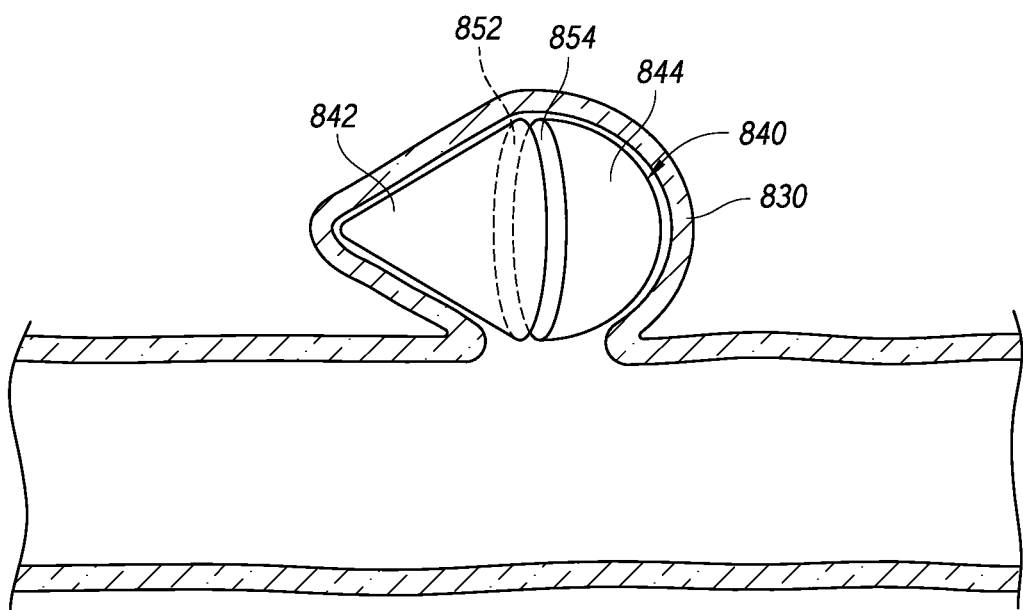
FIG. 39 illustrates an intrasaccular device comprising a plurality of expandable components positioned within a saccular aneurysm, according to some embodiments.

FIG. 39 illustrates an intrasaccular device 840 positioned within an aneurysm 830. The intrasaccular device 840 comprises first and second expandable components 842, 844. The first expandable component 842 comprises a shape that is substantially conical or a paraboloid of revolution. The second expandable component 844 comprises a shape that is substantially hemispherical. The first and second expandable components 842, 844 can comprise respective first and second mating surface 852, 854.

When initially inserted into the aneurysm, prior to expansion, both the first and second expandable components 842, 844 easily fit into the aneurysm 830. Upon expansion, neither the first nor second expandable components 842, 844 entirely packs the aneurysm 830. Thus, if either of the first or second expandable components 842, 844 were positioned by itself in the aneurysm 830, significant movement and potential herniation of the respective component could occur from within the aneurysm 830. However, as the first and second expandable components 842, 844 expand within the aneurysm 830, the first and second mating surfaces 852, 854 can cause the first and second expandable components 842, 844 to become aligned within the aneurysm 830. Such alignment, as illustrated in FIG. 39, can tend to prevent dislocation of either the first or second expandable components 842, 844, thus securing the intrasaccular device 840 within the aneurysm 830.

According to some embodiments, an intrasaccular the first and second mating surfaces 852, 854 can be substantially flat. However, as illustrated in FIG. 40, some embodiments can be configured such that an intrasaccular device 860, positioned within an aneurysm 830, comprises first and second mating surfaces 870, 872 of first and second expandable components 880, 882 can comprise an engagement mechanism 884. The engagement mechanism 884 can comprise engagement structures, such as a recess and a corresponding protrusion, as illustrated. The engagement mechanism 884 can comprise one of a variety of structures, such as one or more recesses and one or more corresponding protrusions, including hemispherical, cylindrical, conical, or other such geometric mating recesses and protrusions. Accordingly, the engagement mechanism 84 can tend to prevent slippage between the first and second mating surfaces 870, 872, thus tending to cause the first and second expandable components 880, 882 to function as a composite unit.

As noted above with respect to FIGS. 13-15, some embodiments of the intrasaccular device can comprise a hollow component that can be implanted into an aneurysm. Although a plurality of hollow components can be implanted into the aneurysm as a system, a single hollow component can also be set in place and later packed with one or more expandable components. Thus, the hollow component can act as a support or framing structure having an enclosed cavity configured to receive additional components therein.

Figure 41:
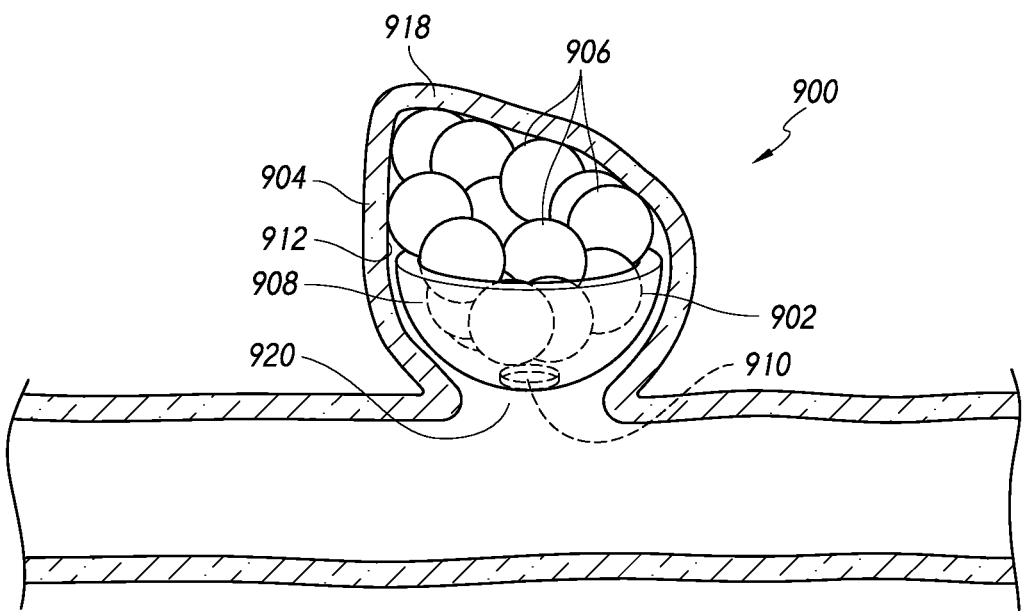
FIG. 41 illustrates an intrasaccular device comprising a plurality of expandable components positioned within a saccular aneurysm, according to some embodiments.

For example, FIG. 41 illustrates an intrasaccular device 900 in the form of a hollow expandable component 902 that is implanted into an aneurysm 904 along with a plurality of expandable components 906. As shown, the hollow component 902 can be in the form of a hollow hemispherical shell that can act as a support or framing structure for the aneurysm and additional expandable components placed therein. The hollow component 902 can have an outer surface 908 that is in contact against an inner wall 912 of the aneurysm 904. As illustrated, the contact between the outer surface 908 and the aneurysm wall 912 can be along a portion of the aneurysm wall 912 that has a cross-sectional profile greater than the size of the opening or passing profile of the neck 920 of the aneurysm 904. Further, contact between the outer surface 908 and the aneurysm wall 912 can be at least along the lower half of the aneurysm 904.

In some embodiments, the outer surface 908 of the hollow component 902 can contact against a first section of the aneurysm wall 912 adjacent to the aneurysm neck 920, as well as against a second section of the aneurysm wall 912 adjacent to the aneurysm dome 918, opposite the aneurysm neck 920. For example, the aneurysm 904 or aneurysm wall 912 can be considered in terms of quadrants, and the outer surface 908 can contact at least three quadrants of the aneurysm wall 912. In some embodiments, the outer surface 908 can be caused to contact at least a portion of each quadrant of the aneurysm wall 912. The contact of the outer surface 908 against the aneurysm wall 912 can tend to secure the hollow component 902 within the aneurysm 904 to avoid dislocation or herniation of any portion of the hollow component 902 from the aneurysm 904.

Referring still to FIG. 41, the expandable components 906 can be inserted or injected into a cavity of the hollow component 902 through an aperture 910 formed in a sidewall of the hollow component 902. The aperture 910 can be sized such that the expandable components 906 can be inserted through the aperture 910 in their compressed state, but upon expansion, the expandable components 906 will be unable to exit through the aperture 910. As also illustrated, the expandable components 906 can position themselves during expansion such that irregular shapes of the dome 918 of the aneurysm 904 can be packed. Additionally, the intrasaccular device 900 can provide a lower porosity adjacent to the neck 920 of the aneurysm 904 while having a relatively higher porosity adjacent to the dome 918.

In accordance with some embodiments, the support or framing component can comprise a stent that extends along a lumen adjacent to an aneurysm. The aneurysm can be a saccular or berry, wide neck, or fusiform aneurysm. For example, a stent can be used in combination with any of the variety of intrasaccular devices illustrated above, such as those shown in FIGS. 22-30 and 38-41, which are shown as treating saccular aneurysms. In some embodiments, the framing component can advantageously secure the intrasaccular device within a wide-neck aneurysm by facilitating engagement with a sufficient amount of the aneurysm wall to avoid dislodgement or herniation of the device from the aneurysm into the parent vessel.

Figure 42:
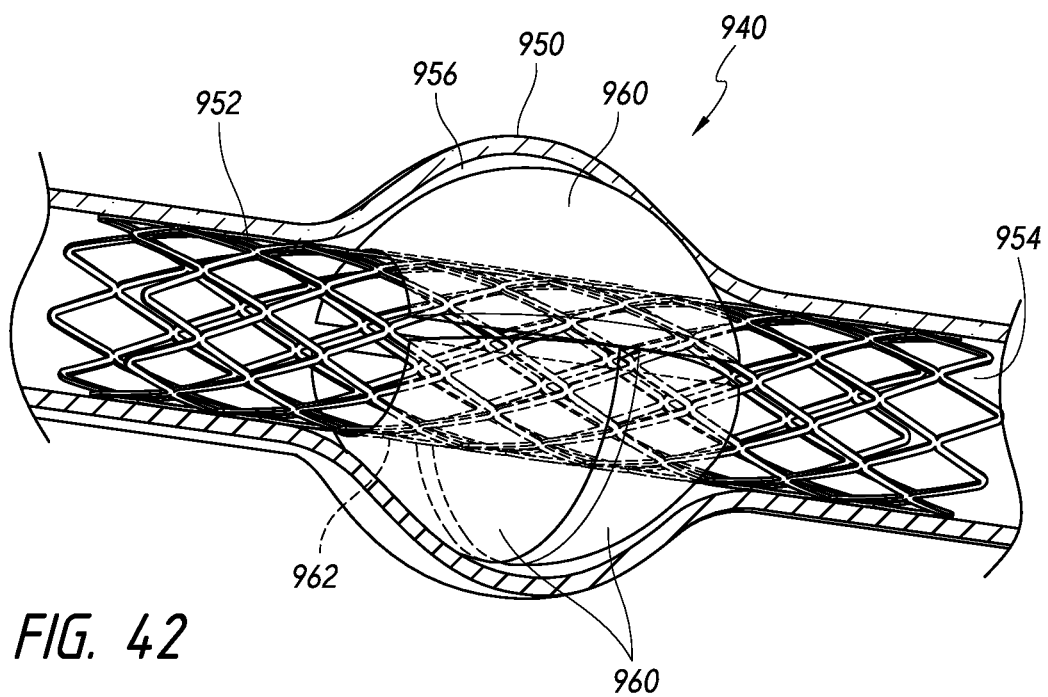
FIG. 42 illustrates an intrasaccular device comprising a plurality of expandable components extending across a fusiform aneurysm, according to some embodiments.

FIG. 42 illustrates an implementation of an intrasaccular device 940 in a method for treating a fusiform aneurysm 950. As illustrated, the intrasaccular device 940 can comprise a stent 952 that extends across the aneurysm 950. The stent 952 can be released at the target location using a catheter and any of a variety of release methods, such as balloon expansion or self-expansion.

When expanded into contact against the inner wall of the lumen 954, the stent 952 can isolate, separate, or divide the inner cavity 956 of the fusiform aneurysm 950 from a central portion of the lumen 954.

When the stent 952 is in place, at least one expandable component 960 can be released into the inner cavity 956 between the inner wall of the aneurysm 950 and an outer surface 962 of the stent 952. The expandable component(s) 960 can be inserted into the cavity 956 through an opening in a wall of the stent 952 (or if the stent 952 is braided, through an interstice of the braid).

As discussed herein, the expandable component(s) 960 can have one or more characteristics that improve the effectiveness of the intrasaccular device 940. Further, the characteristics of the expandable component 960 can be selected based on the shape or configuration of the aneurysm 950, as discussed above. As shown in FIG. 42, the expandable components can have a specific shape to pack the cavity 956 (e.g., a sectioned sphere with a luminal void extending through the sections, thus providing a flatter cylindrically shaped surface that can abut the outer surface of the stent 952). However, any of a variety of other shapes can also be selected and inserted into the cavity 956.

Figure 43:
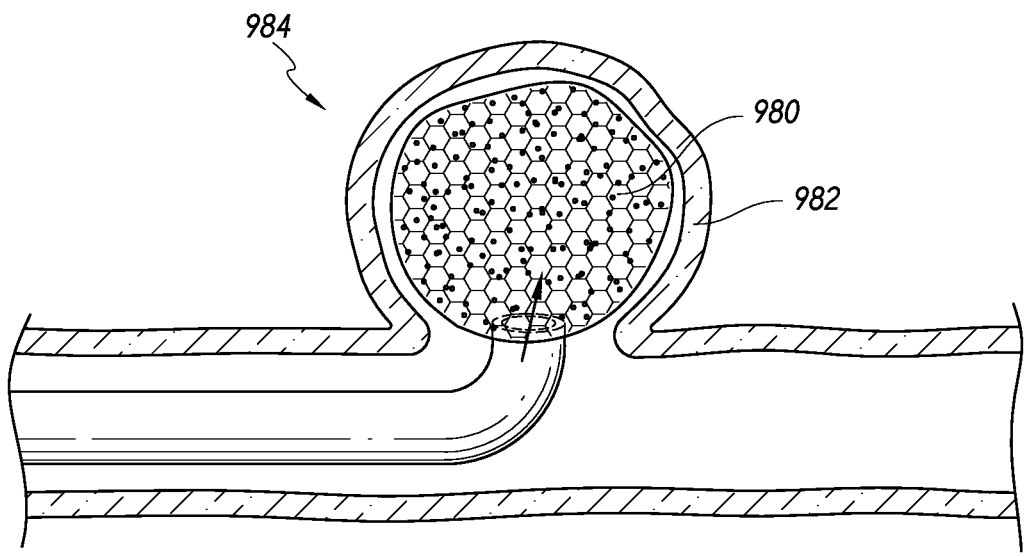
FIG. 43 illustrates a schematic view of a procedure in which an embolic liquid and an intrasaccular device comprising single expandable component are inserted into an aneurysm, according to some embodiments.

In accordance with some embodiments, after an intrasaccular device has been implanted into an aneurysm, a material such as a liquid embolic (as discussed above), a drug, a radiopaque material, a contrast agent, or other agent can be injected or inserted into the aneurysm. The injection or insertion can occur prior to, concurrently with, or after expansion of the intrasaccular device within the aneurysm. As such, the material can be absorbed into at least a portion of the intrasaccular device or pack any remaining voids within the aneurysm around the intrasaccular device. The injection of a liquid embolic can advantageously increase the overall packing density of the device. FIGS. 43 and 44 illustrate embodiments in which a liquid embolic is inserted into the aneurysm in combination with an intrasaccular device.

For example, FIG. 43 illustrates that a material 980 (e.g., a liquid embolic, drug, radiopaque material, contrast agent, or other agent) is being inserted into an aneurysm 982 along with an intrasaccular device 984. The intrasaccular device 984 can have a high porosity, which can allow the material 980 to penetrate the intrasaccular device 984.

FIG. 44 illustrates injection of a material 990 into an aneurysm 992. As shown, the material 990 can flow into the aneurysm 982 into the interstice is formed between expandable components of the intrasaccular device 994. In such an embodiment, the components of the intrasaccular device 994 can have a lower porosity such that the material 998 may not tend to penetrate the components of the intrasaccular device 994 as much as in the embodiment illustrated in FIG. 43.

Thus, various materials can be injected or inserted into the aneurysm to supplement or complement the treatment provided by an intrasaccular device.

FIGS. 45-52 illustrate additional embodiments of an intrasaccular device that uses a support or framing component or structure in combination with secondary expandable components.

Figure 45:
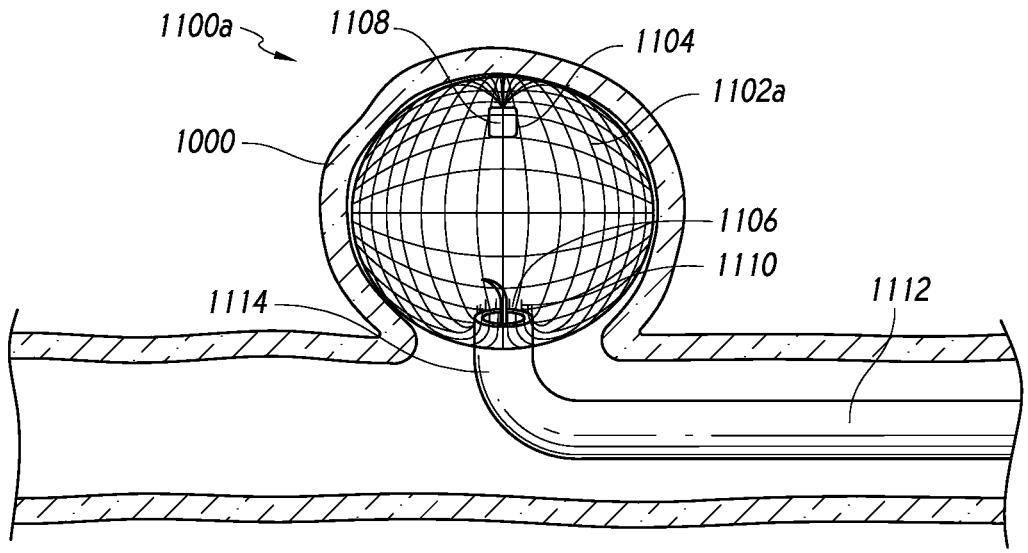
FIG. 45 illustrates a delivery procedure for delivering coils or foam within an interior of an intrasaccular framing device, according to some embodiments.
Figure 46:
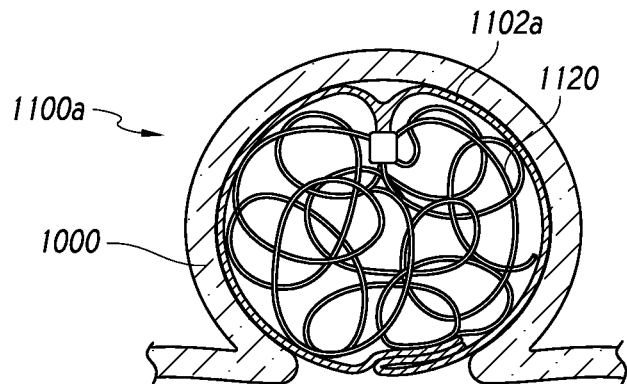
FIG. 46 illustrates a partial cross-sectional view of the intrasaccular framing device as similarly shown in FIG. 45, packed with coils, according to some embodiments.

FIGS. 45-46 illustrates an embodiment in which an aneurysm 1000 is treated using an intrasaccular device 1100a, which comprises a framing structure 1102a having a closed end 1104 and an open end 1106. In some embodiments, the framing structure 1102a can be formed from a braided material.

In one embodiment, the closed end 1104 of the framing structure is sealed via a clamp 1108, an adhesive, or may be heat welded via known techniques. The closed end 1104 may be inverted relative to the remaining framing structure 1102a and depend inwardly within the interior thereof. The open end 1106 of the framing structure 1102a may be in diametrical opposed relation to the closed end 1104. The individual filaments ends 1110 of the framing structure at the open end 1106 also may be inverted and disposed within the interior of the framing structure 1102a.

FIG. 45 depicts the introduction of the coils through the open end 1106 of the framing structure 1102a. Suitable braid materials, structures, and method for manufacturing the framing structure 1102a are disclosed in commonly assigned U.S. Pat. No. 6,168,622 to Mazzocchi, U.S. Pat. No. 8,142,456, issued Mar. 27, 2012, U.S. Patent Application Publication No. 2011/0319926, filed on Nov. 11, 2010, and U.S. Patent Application Publication No. 2012/0330341, filed on Jun. 22, 2011, the entireties of each of which are incorporated herein by reference. Braid materials may include stainless steel, nitinol cobalt chromium or the like.

Figure 47:
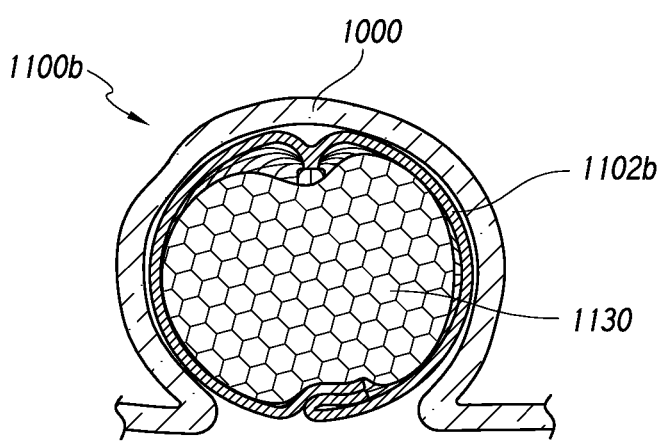
FIG. 47 illustrates a partial cross-sectional view of the intrasaccular framing device as similarly shown in FIG. 45, packed with at least one foam component, according to some embodiments.
Figure 48:
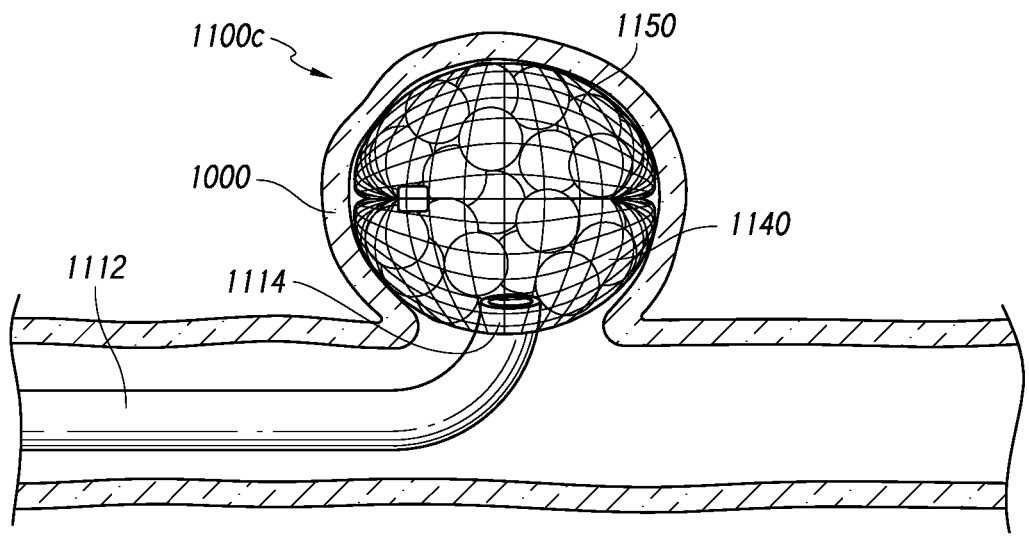
FIG. 48 illustrates another embodiment of an intrasaccular framing device, packed with at least one foam component, according to some embodiments.
Figure 49:
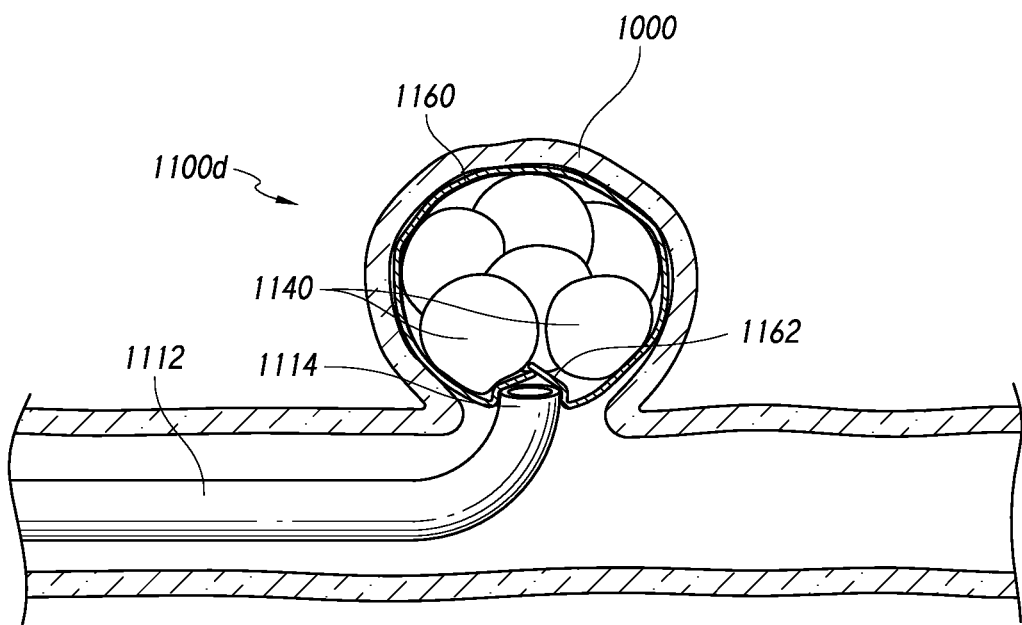
FIG. 49 illustrates yet another embodiment of an intrasaccular framing device, packed with at least one foam component, according to some embodiments.

As shown in the embodiment of FIGS. 45-46, the framing structure 1102a can be deployed in the aneurysm 1000 and packed with coils 1120. However, as shown in FIG. 47-49, an intrasaccular device 1100b, 1100c, 1100d can comprise a framing structure 1102b, 1150, 1160 that can be packed with at least one expandable component 1130, 1140 (e.g., a foam component). The configuration, selection, and use of the expandable components 1130, 1140 are discussed above and will not be repeated here for brevity. However, any of the embodiments disclosed herein can be used in conjunction with the framing structure 1102a. Further, in embodiments using an expandable component, such as a foam component, the foam can advantageously provide a higher packing density compared to traditional coil packing and accomplish this in a single device.

The framing structure 1102a, combined with coils, an expandable component, or other materials, can also provide the benefit of providing good neck coverage while preventing embolic devices from herniating into the parent artery. Additionally, the use of such a system can also increase packing volume efficiency and achieve stasis.

As illustrated, the framing structure 1102a may provide a support or scaffold for the supplemental intrasaccular components or materials, including coils, expandable components, or other materials (e.g., a liquid embolic, drug, radiopaque material, contrast agent, or other agent). The coils 1120 or expandable component 1130 may contain or be coated with bioactive coating that promotes specific clinical theory such as endothelialization, thrombosis, etc.

Figure 50:
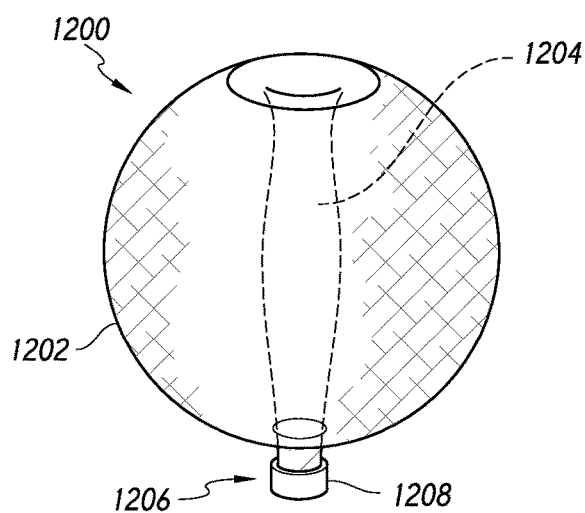
FIGS. 50-52 are schematic views of different intrasaccular framing devices, according to some embodiments.
Figure 51:
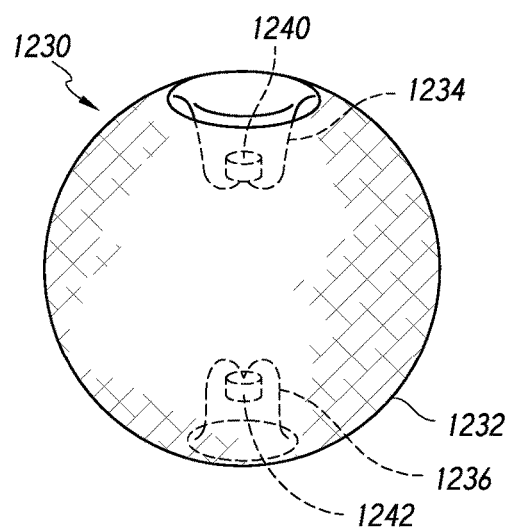
Figure 52:
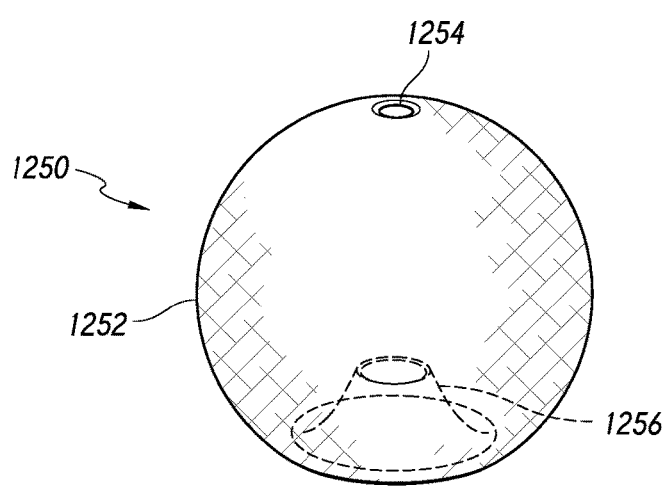

Referring briefly to FIGS. 50-52, these figures illustrate examples of framing structures that can be used as support or framing components, according to some embodiments. In FIG. 50, a braided device 1200 can comprise a single-layer outer portion 1202 that is formed by inverting a tubular braid such that an inner portion 1204 of the braid extends through a center portion of the device 1200. Ends of the inner and outer portions 1202, 1204 meet at a first end 1206. Although the filament ends of the inner and outer portions 1202, 1204 can remain free (as tufts) or unbundled, the first end 1206 can comprise a hub or coupling device 1208 that bundles the inner and outer portions 1202, 1204 together. In some embodiments, the hub or coupling device 1208 can be recessed within an interior of the device 1200, although it is shown protruding in FIG. 50.

FIG. 51 illustrates another embodiment of a framing structure in which a braided device 1230 comprises at least one layer 1232 extending around the periphery of the device 1230. In some embodiments, a single layer can be used, but multiple braided layers are also possible. The device 1230 can comprise first and second ends 1234, 1236 that can be inverted or recessed into the device 1232 formed a smooth outer surface for the device 1230. The first and second ends 134, 136 can be open or closed. As shown, the first and second ends 1234, 1236 can comprise coupling devices 1240, 1242, which close both ends 1234, 1236. However, one or both of the first and second ends 1234, 1236 can also be open, such that the filaments ends thereof are free and unbundled.

FIG. 52 illustrates yet another embodiment of the framing structure in which a braided device 1250 comprises a dual layer shell 1252 having a substantially closed end 1254 and an open end 1256. The open end 1256 can be inverted or recessed into the device 1250.

Referring again to FIGS. 45-46 and 48-49, after a framing structure 1102a, 1150, 1160 has been released an expanded into contact against an inner wall of the aneurysm 1000, the procedure of implanting coils, an expandable component, or other materials into the framing structure 1102a, 1150, 1160 can be performed by either inserting a catheter 1112, such as a distal end 1114 thereof, between filaments of the framing structure (see FIG. 48) or into an open end of the framing structure (see FIGS. 45 and 49).

In implementing a method for placing a framing structure within an aneurysm and injecting coils, expandable component(s), or other materials into the framing structure, the open end or widest interstices of the framing structure can be positioned at the neck of the aneurysm so as to facilitate insertion of the distal end 1114 of the catheter 1112 into the open end or between the filaments (i.e., into an interstice) of the framing structure. In embodiments having a braided material for the framing structure, the braid pattern can be properly aligned to facilitate entry of the materials into the framing structure. As in other embodiments disclosed herein, the framing structure can comprise a radiopaque material or component that facilitates visualization and enables the clinician to align the framing structure as needed within the aneurysm.

As illustrated in FIGS. 46-47 and 49, after the coils, expandable component, or other materials have been inserted into the interior of the braided device through its open end, the open end can collapse onto itself or onto an inner surface of the framing structure as the coils, expandable component, or other materials settle or expand within the cavity of the framing structure. As shown in FIG. 49, the distal end 1114 of the catheter 1112 can be withdrawn, thus allowing the open tube portion 1162 to close onto itself in response to expansive forces from the expanding component(s) or materials. Further, in some embodiments, as illustrated in FIG. 52, an open end 1256 can define a generally tubular portion that can be deflected into contact with the inner wall of the framing structure when at least one expandable component is released into and expand within the cavity of the framing structure. As such, the open end can tend to self-seal, thus preventing herniation of the coils, expandable component, or other materials disposed within the framing structure.

The composite effect of the coils, expandable component, and/or other materials inserted into the framing structure can provide the advantages and benefits discussed above with respect to various other expandable components. As such, the clinician can determine and control various intrasaccular implant characteristics, including porosity, composition, material, shape, size, interconnectedness, inter-engagement, coating, etc.

According to some embodiments, systems or kits having a framing structure and at least one coil, expandable component, and/or other material can be provided.

Intrasaccular implant devices and procedures for treating aneurysms can be improved by interconnecting individual components of the intrasaccular device. According to some embodiments, a plurality of expandable components can be interconnected along a wire, filament, or other disconnectable or breakable material. The expandable components can be connected in a linear configuration (see FIGS. 53-58C), a planar matrix (see FIGS. 59A-60B), or in a three-dimensional matrix (see FIGS. 61A-61B). The expandable components of such interconnected linear, planar, or three-dimensional matrices can be sized and configured in accordance with desired porosity, size, shape, radiopacity, or other characteristics disclosed herein, which will not be repeated here for brevity.

In some embodiments, methods are provided by which interconnected expandable components can be released into an aneurysm. The interconnected components can be pre-configured (e.g., a select number of components can be removed from a larger strand or array of components) prior to implantation and later inserted into a delivery catheter. Thereafter, the entire strand or assembly of interconnected expandable components of the intrasaccular device can be released into the aneurysm.

However, in accordance with some embodiments, an entire strand or array of components (which would, in their expanded state, exceed the available space in the aneurysm) can be loaded into a delivery catheter, and while implanting and observing the packing behavior, a clinician can determine that a select portion of the interconnected expandable components is sufficient for a given aneurysm. Thereafter, the select portion of the interconnected expandable components can be broken or cut in situ so as to be released into the aneurysm.

Referring now to FIGS. 53-57C, various embodiments of linearly interconnected expandable components are shown. As illustrated in these figures, an intrasaccular device 1300a, 1300b, 1300c, 1300d can comprise a strip of expandable components 1302a, 1302b, 1302c, 1302d. The strip 1302a, 1302b, 1302c, 1302d may include spaces or breaks separating adjacent expandable components to facilitate selective detachment of expandable components. The configuration of the strip 1302a, 1302b, 1302c, 1302d permits the clinician to either detach a desired number of expandable components needed for the procedure before initiating the procedure or detaching a desired number of components in situ. Intrasaccular devices having interconnected expandable components can be delivered with or without a supporting or framing structure.

Figure 53:
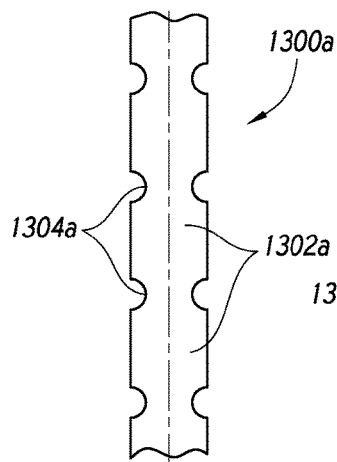
FIGS. 53-56 illustrate embodiments of the intrasaccular device incorporating a strip of foam structures.
Figure 54:
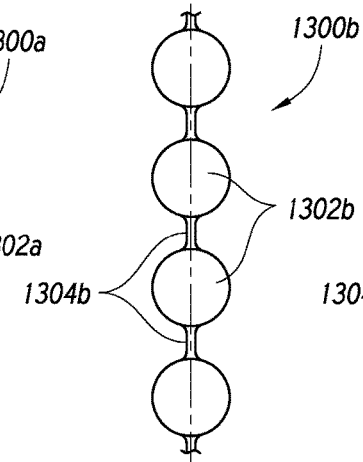
Figure 55:
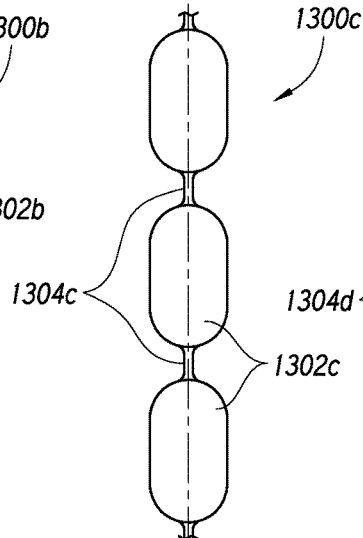
Figure 56:
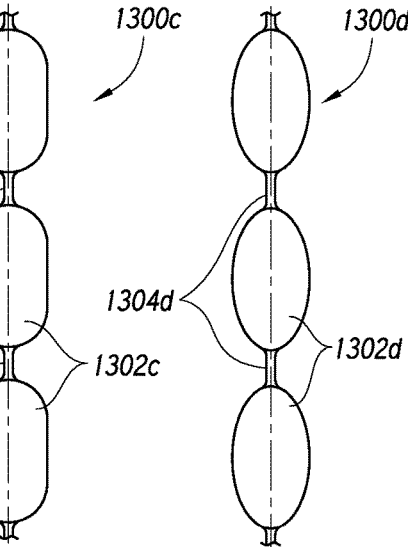

The expandable components 1302a, 1302b, 1302c, 1302d may be interconnected along one or more strings, filaments, carriers, indentations, reduced size sections, or perforation lines (which may include or be devoid of a filament or string) 1304a, 1304b, 1304c, 1304d. For example, FIG. 53 illustrates an intrasaccular device 1300a having a plurality of indentations or 1304a (which can also include or be substituted by perforation lines) that separate adjacent expandable components. FIG. 54 illustrates an intrasaccular device 1300b having a plurality of expandable components that are formed or molded along a filament or string 1304b. Further, FIGS. 55-56 can include filaments or reduced diameter expandable portions 1304c, 1304d that interconnect adjacent expandable components.

In accordance with some embodiments, the strings, filaments, carriers, indentations, reduced size sections, or perforation lines extending between adjacent expandable components can enhance pushability of the intrasaccular device 1300a, 1300b, 1300c, 1300d into the aneurysm.

Figure 57A:
FIGS. 57A-57C illustrate cross-sectional shapes that can be employed, alone or in combination with each other, in the intrasaccular structures shown in FIGS. 53-56.
Figure 57B:
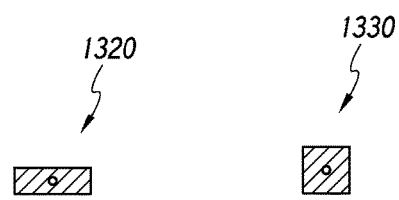
Figure 57C:
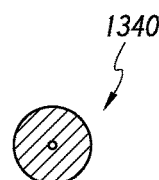

Further, as illustrated in FIGS. 57A-57C, the expandable components of the intrasaccular device 1300a, 1300b, 1300c, 1300d can comprise one or more cross-sectional profiles, such as a rectangle shape 1320 (see FIG. 57A), a square shape 1330 (see FIG. 57B), or a round, e.g., circular, shape 1340 (see FIG. 57C). Various other cross-sectional profiles can be provided, such as polygons having three, five, six, seven or eight sides, star shapes, clover shapes, and the like. Additionally, a single intrasaccular device can comprise expandable components that have different cross-sectional shapes or that have identical cross-sectional shapes, according to some embodiments.

Further, in accordance with some embodiments, consecutive expandable components of an intrasaccular device

1300a, 1300b, 1300c, 1300d can descend in size, which can allow selection of a subset of the expandable components of the intrasaccular device 1300a, 1300b, 1300c, 1300d based on a specific target aneurysm size or shape.

Figure 58A:
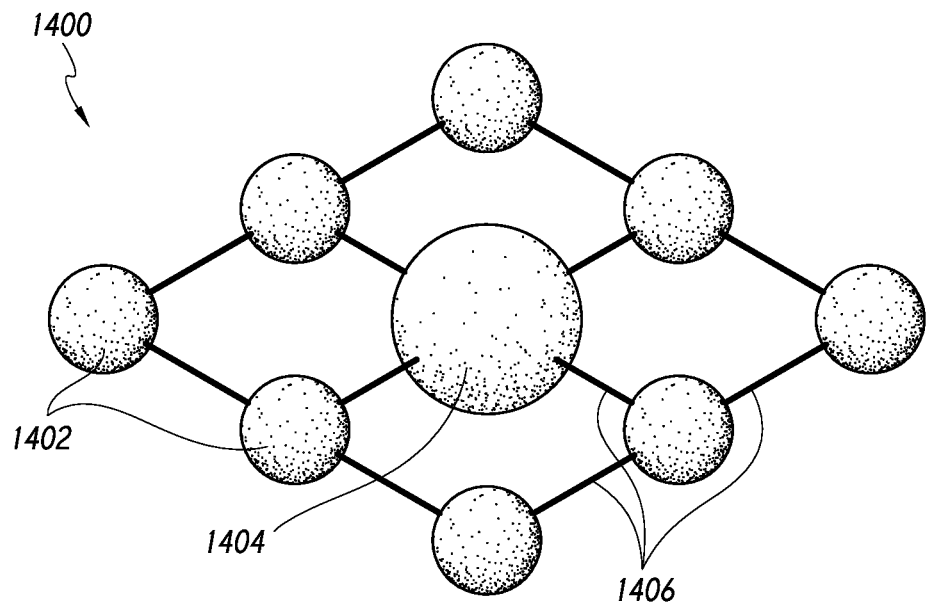
FIG. 58A illustrates an embodiment of an intrasaccular device comprising a plurality of interconnected expandable components in a compressed state, according to some embodiments.

FIGS. 58A-60B illustrate additional embodiments of intrasaccular devices that can have nonlinear configurations. For example, FIG. 58A illustrates an embodiment of an intrasaccular device 1400 comprising a layer or planar array of a plurality of interconnected expandable components 1402 in a compressed state, according to some embodiments. The expandable components 1402 can be interconnected by one or more strings, filaments, carriers, indentations, reduced size sections, or perforation lines (which may include or be devoid of a filament or string) 1406. The expandable components 1402 can have the same or different shapes, sizes, or material properties as each other. For example, as illustrated in FIGS. 58A-58B, the intrasaccular device 1400 can comprise a central expandable component 1404 having an expanded size that is much greater than the expanded sizes of surrounding expandable components 1402. Thus, as shown in FIG. 58B, when released into an aneurysm, the intrasaccular device 1400 can expand into a configuration in which the central component 1404 is anchored in the aneurysm 1420 by the surrounding expandable components 1402.

Figure 58B:
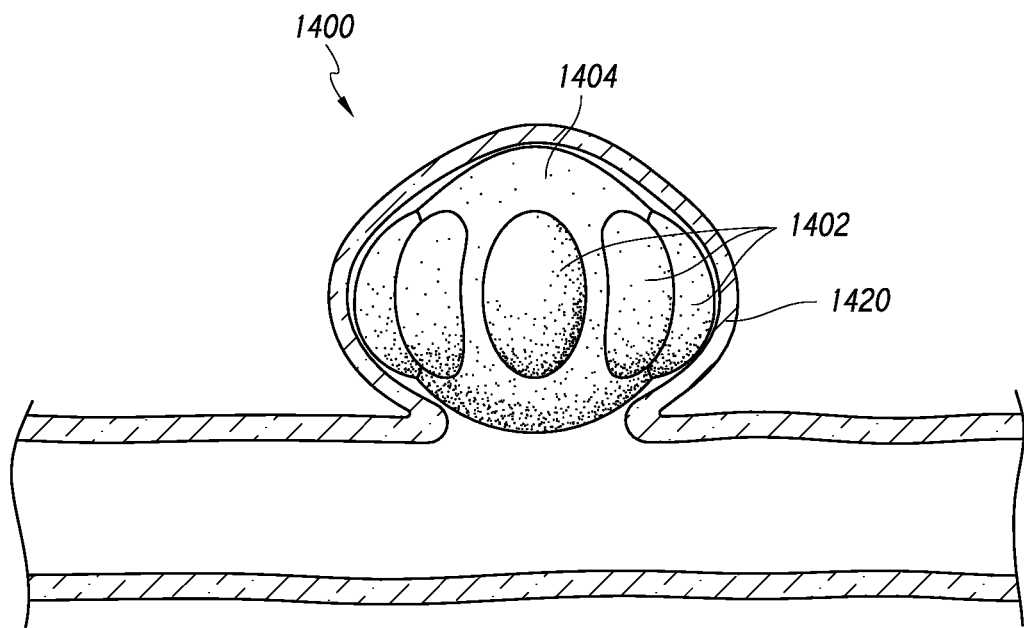
FIG. 58B illustrates the intrasaccular device of FIG. 58A comprising a plurality of interconnected expandable components in an expanded state, according to some embodiments.

Similar to the embodiment illustrated in FIGS. 58A-58B, various embodiments can be provided in which surrounding or anchoring expandable components can be interconnected with other components in a matrix to enhance the fit or engagement of the intrasaccular device within an aneurysm. Further, such surrounding expandable components can have characteristics different from those of the central expandable component, such as having coatings or other properties that beneficially affect the efficacy of the intrasaccular device within the aneurysm.

Figure 59A:
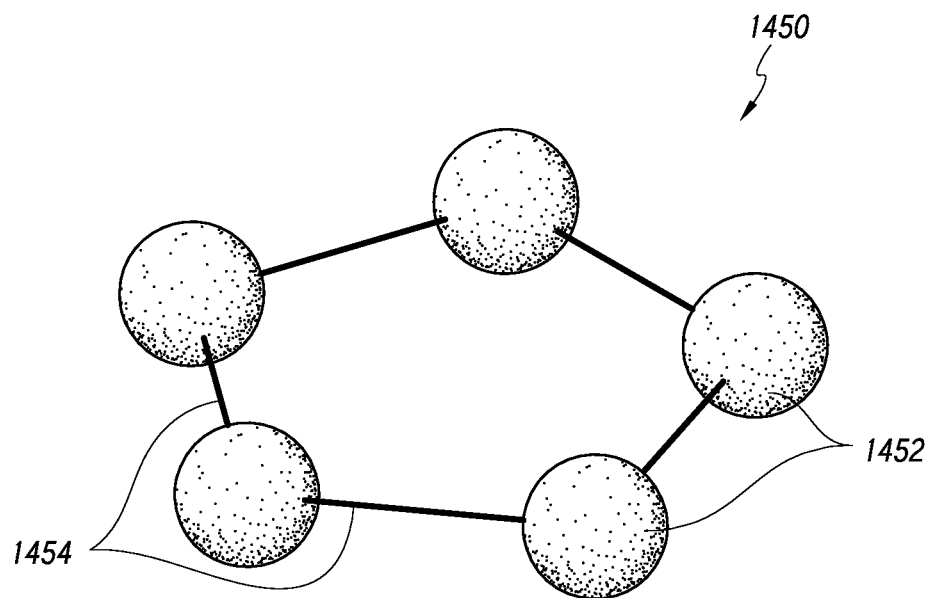
FIG. 59A illustrates an embodiment of an intrasaccular device comprising a layer of interconnected expandable components in a compressed state, according to some embodiments.
Figure 59B:
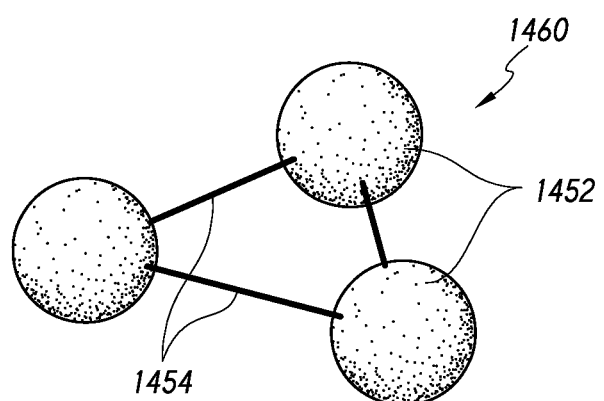
FIG. 59B illustrates another embodiment of an intrasaccular device comprising a layer of interconnected expandable components in a compressed state, according to some embodiments.

FIG. 59A-59B illustrate embodiments of intrasaccular devices 1450, 1460 comprising a layer, ring, or planar array of interconnected expandable components 1452, 1462 in a compressed state. The expandable components 1452, 1462 can be interconnected by one or more strings, filaments, carriers, indentations, reduced size sections, or perforation lines (which may include or be devoid of a filament or string) 1454, 1464. For example, each of the expandable components 1452, 1462 can be connected to at least two other expandable components 1452, 1462.

Figure 60A:
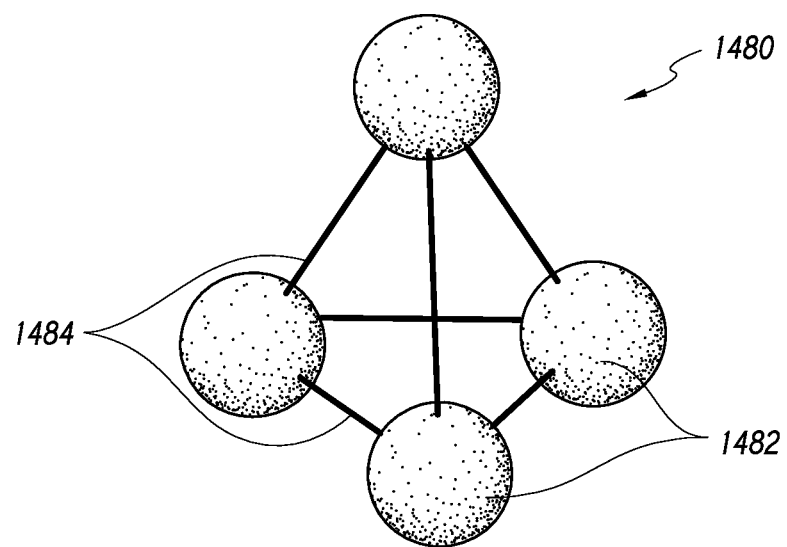
FIG. 60A illustrates an embodiment of an intrasaccular device comprising a three-dimensional array of interconnected expandable components in a compressed state, according to some embodiments.
Figure 60B:
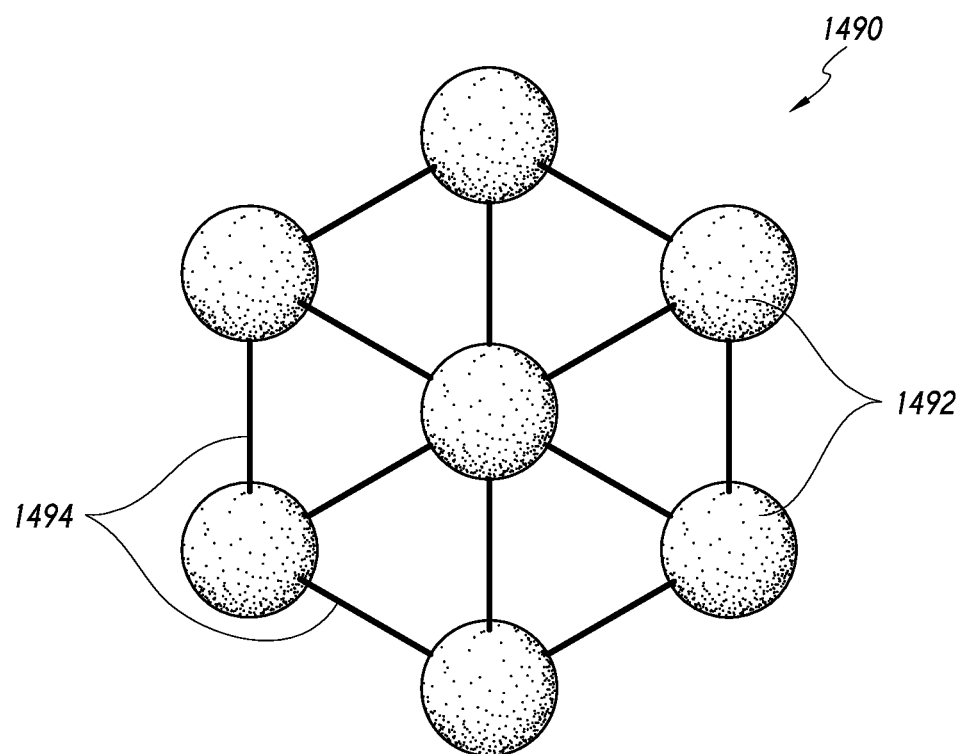
FIG. 60B illustrates another embodiment of an intrasaccular device comprising a three-dimensional array of interconnected expandable components in a compressed state, according to some embodiments.

FIG. 60A-60B illustrate embodiments of intrasaccular devices 1480, 1490 comprising a three-dimensional or multi-planar array of interconnected expandable components 1482, 1492 in a compressed state. The expandable components 1482, 1492 can be interconnected by one or more strings, filaments, carriers, indentations, reduced size sections, or perforation lines (which may include or be devoid of a filament or string) 1484, 1494. For example, each of the expandable components 1482, 1492 can be connected to at least two other expandable components 1482, 1492 to create a three-dimensional array. Similar to the layer or planar array shown in FIGS. 58A-59B, a three-dimensional array can have expandable components that each have characteristics different from those of other components, such as having coatings or other properties that beneficially affect the efficacy of the intrasaccular device within the aneurysm.

The advantageous features of intrasaccular devices having strip configurations can allow a clinician to quickly and readily assess a target aneurysm and tailor an intrasaccular device specifically for the procedure. The customization of an intrasaccular device strip can be done before implantation or in situ. Further, the interconnectedness of the components tends to ensure that no component is lost.

Figure 61:
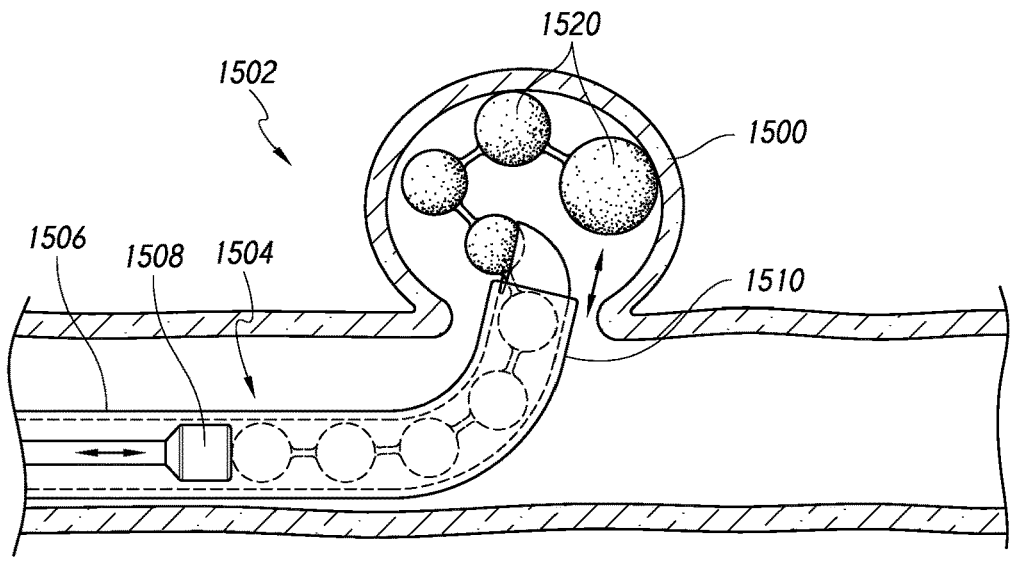
FIG. 61-63 illustrate a delivery system and procedure for delivering a plurality of interconnected expandable components, according to some embodiments.
Figure 62:
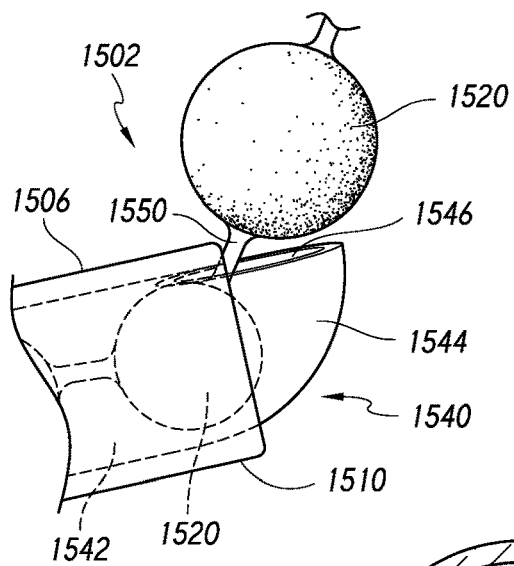
Figure 63:
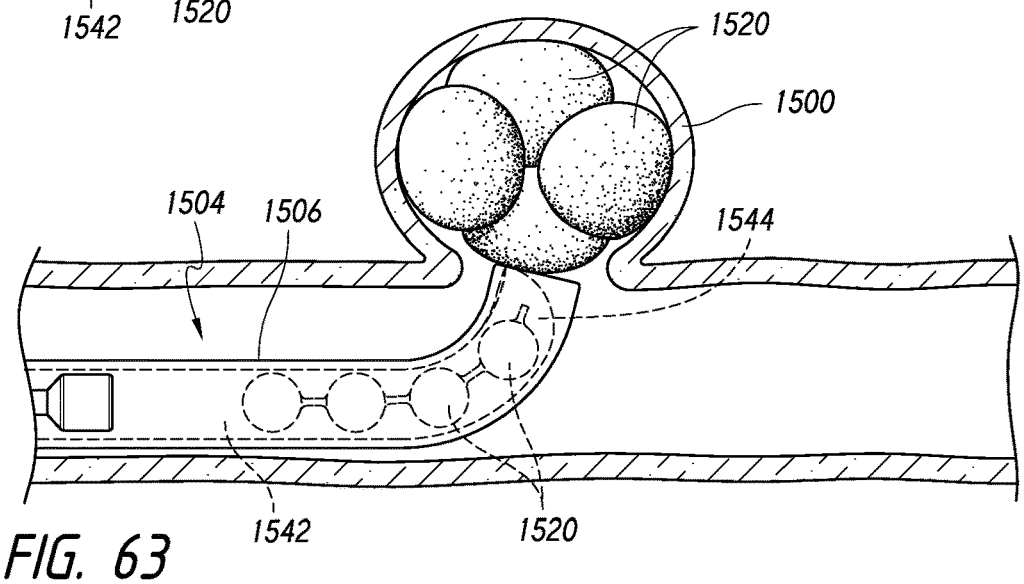

FIGS. 61-63 illustrate a delivery system and procedure for delivering a strip of interconnected expandable components, according to some embodiments. As discussed, the configuration of the strip 1302a, 1302b, 1302c, 1302d permits the clinician to detach a desired number of expandable components needed for the procedure.

Prior to initiating the implantation of an strip of interconnected intrasaccular device, a clinician, through imaging means, can determine the size and dimension of an aneurysm 1500. Once the dimensioning is determined, the clinician can determine decide upon a configuration for the intrasaccular device or strip 1502 of interconnected expandable components to be implanted. As shown in FIG. 61, the strip 1502 can be delivered using an implant delivery assembly 1504, which can comprise a catheter 1506 and a pusher component 1508.

In some embodiments of the delivery procedure, after determining the configuration for the strip 1502, the clinician can prepare the strip 1502 by separating any unnecessary expandable components there from prior to inserting the strip 1502 into the delivery assembly 1504. Thereafter, the strip 1502 is then introduced within the aneurysm in accordance with any of the aforedescribed methodologies.

However, in some embodiments of the delivery procedure, the clinician can load a strip 1502 into the catheter 1506 before trimming any expandable components from the strip 1502. The clinician can then push the strip 1502 out through a distal end 1510 of the catheter 1506, which causes the individual expandable components 1520 to begin to expand within the aneurysm 1500. As the expansion is taking place, the clinician can determine whether additional expandable components 1520 should be deployed into the aneurysm 1500. If needed, the pusher component 1508 can be moved distally to urge one or more additional expandable components 1520 out of the catheter 1506. When it is determined that a sufficient number of expandable components 1520 are inserted into the aneurysm 1500, the clinician can break or separate the strip 1502 by separating the respective expandable components 1520 via trimming or tearing along the breaks, indentations or score lines and separating the expandable components 1520.

The breaking or separating of adjacent expandable components can be performed by actuating the cutting device 1540. In some embodiments, the cutting device 1540 can comprise a second catheter 1542 that is nested within the catheter 1506. The second catheter 1542 can comprise a distal portion 1544 having an opening 1546 that extends from a side of the second catheter 1542. The distal portion 1544 can have a rounded shape that can guide the expandable components 1520 out through the opening 1546. In order to trim the strip 1502, the second catheter 1542 can be retracted proximally relative to the catheter 1506, thus causing the opening 1546 to close against the distal end 1510 of the catheter 1506, thereby severing a tie or filament extending between adjacent expandable components 1520.

Thereafter, the distal portion 1544 of the second catheter 1542 can be further withdrawn into the catheter 1506 and the delivery assembly 1504 can be removed from the target site.

Many of the features discussed herein can be used with any of the disclosed embodiments. For example, any of the embodiments can comprise an average porosity that varies spatially, any of the variety of disclosed shapes, any of the various disclosed materials or coatings, any of the disclosed 2-D or 3-D interconnected configurations, any of the disclosed inter-engagement configurations or structures, any of the disclosed delivery systems, etc.

The apparatus and methods discussed herein are not limited to the deployment and use of a medical device or stent within the vascular system but may include any number of further treatment applications. Other treatment sites may include areas or regions of the body including any hollow anatomical structures.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

We claim:

1. A method for treatment of an aneurysm, comprising:
   intravascularly delivering a framing device through a catheter in a compressed configuration to a cavity of the aneurysm, wherein the framing device comprises a proximal end portion, a distal end portion, and a sidewall extending between the proximal end portion and the distal end portion, the sidewall comprising multiple braided layers extending along an entire length of the sidewall in the compressed configuration;
   releasing the framing device from the delivery catheter to expand the framing device to an expanded configuration in the aneurysm cavity such that at least a portion of the framing device contacts an inner surface of the aneurysm wall, wherein the sidewall of the framing device comprises multiple braided layers extending along the entire length of the sidewall in the expanded configuration, and wherein the framing device encloses an interior volume; and
   positioning a liquid embolic between the framing device and the aneurysm wall.

2. The method of claim 1, further comprising positioning an aperture of the framing device at the neck of the aneurysm.

3. The method of claim 1, wherein the catheter is a first catheter and the method further comprises inserting a second catheter into an aperture of the framing device.

4. The method of claim 1, wherein the framing device assumes a substantially spherical shape when released from the catheter.

5. The method of claim 1, wherein the framing device comprises a hollow, braided structure.

6. The method of claim 1, wherein the framing device is a braided device comprising a dual layer shell.

7. The method of claim 1, wherein the framing device has a first, closed end and a second end opposite the first end, the second end having an opening, and wherein the method comprises aligning the opening with a neck of the aneurysm.

8. The method of claim 1, wherein the framing device has a porosity such that the liquid embolic does not penetrate the framing device.

9. The method of claim 1, wherein the framing device includes stainless steel, nitinol, and/or cobalt chromium.

10. The method of claim 1, wherein a distalmost end of the framing device in the compressed configuration is also a distalmost end of the framing device in the expanded configuration.

11. The method of claim 1, wherein the sidewall is inverted inwardly into the interior volume defined by the sidewall at the distal end portion of the framing device.

12. The method of claim 1, wherein, after releasing the framing device from the delivery catheter to expand the framing device to an expanded configuration in the aneurysm cavity, wherein the framing device is positioned entirely within the aneurysm cavity.

13. A method for treatment of an aneurysm, comprising:
advancing an expandable framing device through a catheter to a cavity of the aneurysm, the expandable framing device comprising a proximal end portion, a distal end portion, and a dual-layered shell extending from the proximal end portion to the distal end portion along an entire length of the framing device while advancing the expandable framing device through the catheter;
positioning the expandable framing device in the cavity of an aneurysm, the framing device having an expanded state in which the framing device encloses a cavity and includes an aperture in communication with the cavity;
expanding the framing device in the aneurysm cavity such that (a) at least a portion of the framing device contacts an inner surface of the aneurysm wall, (b) the aperture is accessible through a neck of the aneurysm, and (c) the expandable framing device comprises a dual-layered shell extending along the entire length of the framing device once expanded in the aneurysm cavity;
advancing a liquid embolic through the aperture in the framing device; and positioning the liquid embolic between the framing device and the aneurysm wall.

14. The method of claim 13, wherein the framing device includes stainless steel, nitinol, and/or cobalt chromium.

15. The method of claim 13, wherein the framing device assumes a substantially spherical shape in an expanded state.

16. The method of claim 13, wherein the framing device comprises a hollow, braided structure.

17. The method of claim 13, wherein the framing device comprises multiple braided layers.

18. The method of claim 13, wherein the framing device has a first, closed end and a second end opposite the first end, the second end having an opening, and wherein the method comprises aligning the opening with a neck of the aneurysm.

19. The method of claim 13, wherein the framing device has a porosity such that the liquid embolic does not penetrate the framing device.

20. The method of claim 13, wherein a distalmost end of the framing device while advancing the framing device through the catheter is also a distalmost end of the framing device once the framing device is expanded in the aneurysm cavity.

21. The method of claim 13, wherein the dual-layered shell is inverted inwardly into the cavity of the framing device at the distal end portion of the framing device.

22. The method of claim 13, wherein, after releasing the framing device from the delivery catheter to expand the framing device to an expanded configuration in the aneurysm cavity, wherein the framing device is positioned entirely within the aneurysm cavity.

\* \* \* \* \*